United States Patent [19]

Watthey

[11] Patent Number: 4,473,575

[45] Date of Patent: * Sep. 25, 1984

[54] 3-AMINO-(1)-BENZAZEPIN-2-ONE-1-ALKANOIC ACIDS

[75] Inventor: Jeffrey W. H. Watthey, Chappaqua, N.Y.

[73] Assignee: Ciba-Geigy Corporation, Ardsley, N.Y.

[ * ] Notice: The portion of the term of this patent subsequent to Oct. 18, 2000 has been disclaimed.

[21] Appl. No.: 465,695

[22] Filed: Feb. 10, 1983

Related U.S. Application Data

[63] Continuation-in-part of Ser. No. 398,241, Jul. 19, 1982, Pat. No. 4,410,520, which is a continuation-in-part of Ser. No. 319,863, Nov. 9, 1981, abandoned, which is a continuation-in-part of Ser. No. 291,907, Aug. 11, 1981, abandoned.

[51] Int. Cl.$^3$ .................. C07D 223/16; A61K 31/55
[52] U.S. Cl. ........................ 424/263; 260/239.3 B; 260/239.3 T; 424/244; 424/267; 424/274
[58] Field of Search ............... 260/239.3 B; 424/244, 424/267, 274, 263

[56] References Cited

U.S. PATENT DOCUMENTS

| | | | |
|---|---|---|---|
| 3,748,321 | 7/1973 | Krapcho | 260/239 BB |
| 4,409,146 | 10/1983 | Thersett et al. | 260/239.3 R |
| 4,410,520 | 10/1983 | Watthey | 260/239.3 B |
| 4,415,496 | 11/1983 | Harris et al. | 260/239.3 B |

FOREIGN PATENT DOCUMENTS

| | | | |
|---|---|---|---|
| 673856 | 6/1966 | Belgium | 260/239.3 B |
| 12401 | 1/1980 | European Pat. Off. | 564/194 |
| 26640 | 4/1981 | European Pat. Off. | 260/239.3 B |
| 46291 | 2/1982 | European Pat. Off. | 260/239.3 B |
| 2714442 | 10/1977 | Fed. Rep. of Germany | 260/239.8 B |
| 49-28753 | 7/1974 | Japan | 260/239.3 B |
| 49-28754 | 7/1974 | Japan | 260/239.3 B |
| 1305278 | 1/1973 | United Kingdom | 260/239.3 B |
| 2095252 | 9/1982 | United Kingdom | 546/147 |

OTHER PUBLICATIONS

Stewart "Australian J. of Chemistry", vol. 33, (1980), pp. 633–640.
Friedinger et al., "J. Org. Chem.", vol. 47, (1962), pp. 104–109.
Paquette et al., "J. Org. Chem.", vol. 34, (1969), pp. 2879–2880.
Smith, "J. Medicinal Chem.", vol. 24, (1981), pp. 104–109.
Patchett et al., "Nature", vol. 288, pp. 280–283, (1980).
PTO Official Gazette, Abstract of U.S. Pat. No. 4,409,146, issued Nov. 13, 1983.
PTO Official Gazette, Abstract of U.S. Pat. No. 4,409,149, issued Oct. 11, 1983.

*Primary Examiner*—Robert T. Bond
*Attorney, Agent, or Firm*—Norbert Gruenfeld

[57] ABSTRACT

Variously substituted 1-carboxymethyl-3-(carboxymethylamino)-2,3,4,5-tetrahydro-1H-[1]benzazepin-2-ones and functional derivatives are angiotensin converting enzyme inhibitors and are useful as antihypertensive agents. Synthesis of, compositions and methods of treatment utilizing such compounds are included.

22 Claims, No Drawings

3-AMINO-(1)-BENZAZEPIN-2-ONE-1-ALKANOIC ACIDS

CROSS-REFERENCE TO RELATED APPLICATIONS

This is a continuation-in-part of application Ser. No. 398,241 filed July 19, 1982, now U.S. Pat. No. 4,410,520, issued Oct. 18, 1983, which is a continuation-in-part of application Ser. No. 319,863 filed Nov. 9, 1981, now abandoned, which in turn is a continuation-in-part of application Ser. No. 291,907 filed Aug. 11, 1981, now abandoned.

BACKGROUND OF THE INVENTION

F. H. C. Stewart, Australian J. Chemistry 33, 633 (1980) and Japanese patent 74-28753 [Chem. Abstr. 82, 139978m (1975)] described 3-amino-1-unsubstituted-2,3,4,5-tetrahydro-1H-[1]benzazepin-2,5-dione derivatives, and Japanese patent 74-28754 [Chem. Abstr. 82, 139981g (1975)] describes similar 2,5-dihydro-1H-[1]benzazepin-2,5-diones. The substances described in Japanese patent 74-28753 are claimed to have bactericidal activity.

L. A. Paquette et al, J. Organic Chemistry 34, 2879 (1969), describes 1-methyl-2,3,4,5-tetrahydro-1H-[1]benzazepin-2-one. The available literature does not show [1]-benzazepin-2-one-1-alkanoic acids, 3-amino[1-]benzazepin-2-one-1-alkanoic acids or derivatives thereof.

Carboxyalkyl dipeptides and derivatives according to European Patent Application No. 12401 are known as angiotensin-converting enzyme inhibitors and antihypertensives.

SUMMARY OF THE INVENTION

The present invention is based upon the discovery that certain substituted 3-amino-[1]benzazepin-2-one-1-alkanoic acids and derivatives represent a new class of potent angiotensin-converting enzyme (ACE) inhibitors.

The foregoing attributes render the 3-amino-[1]-benzazepin-2-ones of this invention particularly useful when administered, alone or in combination, to mammals, e.g. for the treatment or prevention of diseases responsive to inhibition of angiotensin converting enzyme e.g., cardiovascular disorders such as hypertension and cardiac conditions such as congestive heart failure.

DETAILED DISCLOSURE

This invention relates to novel 3-amino-[1]benzazepin-2-one-1-alkanoic acids, and derivatives useful as angiotensin-converting enzyme inhibitors, processes for preparing same, pharmaceutical compositions comprising said compounds, and methods of treating diseases responsive to inhibition of angiotensin-converting enzyme by administration of said compounds and compositions to mammals.

The compounds of the invention are characterized by the general formula $$\text{(I)}$$

[Structure: benzazepinone with positions 5a, 6, 7, 8, 9, 9a, 1, 2, 3, 4, 5 labeled; substituents $R_4$ at 6, $R_3$ at 9, $R_B$ on N-1, X= at 5, $R_5$ and $R_A$ on N at 3; carbonyl at 2]

wherein $R_A$ and $R_B$ are radicals of the formula $$-CH\begin{matrix}R_1\\R_0\end{matrix} \quad \text{and} \quad -CH\begin{matrix}R_2\\R_0\end{matrix},$$

respectively, in which $R_0$ is carboxy or a functionally modified carboxy;

$R_1$ is hydrogen, lower alkyl, amino(lower)alkyl, aryl, aryl(lower)alkyl, cycloalkyl, cycloalkyl(lower)alkyl, acylamino(lower)alkyl, mono- or di-(lower)alkylamino(lower)alkyl, lower alkylthio(lower)alkyl, carboxy(lower)alkyl, esterified carboxy(lower)alkyl, carbamoyl(lower)alkyl, N-substituted carbamoyl(lower)alkyl, hydroxy(lower)alkyl, etherified or acylated hydroxy(lower)alkyl, aryloxy(lower)alkyl, aryl-(thio-, sulfinyl-, or sulfonyl-)lower alkyl, aryl-N-(lower)alkylamino(lower)alkyl, or arylamino(lower)alkyl;

$R_2$ is hydrogen or lower alkyl;

$R_3$ and $R_4$, each independently, represent hydrogen, lower alkyl, lower alkoxy, lower alkanoyloxy, hydroxy, halogen, trifluoromethyl, or $R_3$ and $R_4$ taken together represent lower alkylenedioxy;

$R_5$ is hydrogen or lower alkyl, and

X represents oxo, two hydrogens, or one hydroxy or acylated hydroxy together with one hydrogen; and wherein the carbocyclic ring may also be hexahydro or 6,7,8,9-tetrahydro; and salts and complexes thereof.

The functionally modified carboxyl group in the meaning of the symbol $R_0$ is e.g. an esterified carboxyl group or a carbamoyl group optionally substituted on the nitrogen atom.

More specifically one or both of $R_0$ represented by $COR_6$ in radical $R_A$ and represented by $COR_7$ in radical $R_B$ independently represent carboxy, esterified carboxy, carbamoyl or substituted carbamoyl.

The salts and complexes of the compounds of formula I are derived from those compounds which have salt forming properties and are preferably pharmaceutically acceptable salts and complexes.

A carboxyl group $R_0$ is represented by $COR_6$ (in radical $R_A$) wherein $R_6$ is hydroxy or $COR_7$ (in radical $R_B$) wherein $R_7$ is hydroxy.

An esterified carboxyl group $R_0$ is especially one in which the esterifying radical represents optionally substituted lower alkyl or optionally substituted phthalidyl and is represented by the partial formula —$COR_6$ (in radical $R_A$) or the partial formula —$COR_7$ (in radical $R_B$)

wherein one or both of $R_6$ and $R_7$ represent lower alkoxy; (amino, mono- or di-lower alkylamino)-substituted lower alkoxy; carboxy-substituted lower alkoxy, e.g. α-carboxy-substituted lower alkoxy; lower alkoxycarbonyl-substituted lower alkoxy, e.g. α-lower alkoxycarbonyl-substituted lower alkoxy; aryl-substituted lower alkoxy, e.g. optionally substituted benzyloxy or pyridylmethoxy; (hydroxy, lower alkanoyloxy or lower alkoxy)-substituted lower alkoxy, e.g. pivaloyloxymethoxy; (hydroxy, lower alkanoyloxy or lower alkoxy)-substituted lower alkoxymethoxy; bicycloalkoxycarbonyl-substituted lower alkoxy, e.g. bicyclo[2,2,1]heptyloxycarbonyl-substituted lower alkoxy, especially bicyclo[2,2,1]heptyloxycarbonyl-substituted methoxy; 3-phthalidoxy; (lower alkyl, lower alkoxy, halo)-substituted 3-phthalidoxy.

An optionally N-substituted carbamoyl group $R_o$ is especially one which is represented by the partial formula —$COR_6$ (in radical $R_A$) or the partial formula —$COR_7$ (in radical $R_B$)

wherein one or both of $R_6$ and $R_7$ represent amino; lower alkylamino; di-lower alkylamino; di-lower alkylamino in which both alkyl groups are linked by a carbon to carbon bond and together with the amino nitrogen form a 5-, 6- or 7-membered heterocyclic ring, e.g. pyrrolidino, piperidino, or perhydroazepino; (amino or acylamino)-substituted lower alkylamino; α-(carboxy or lower alkoxycarbonyl)-substituted lower alkylamino; aryl substituted lower alkylamino in which aryl is preferably phenyl or indolyl and which can be substituted on the α-carbon by carboxy or lower alkoxycarbonyl.

Furthermore, the terms esterified carboxy and N-substituted carbamoyl, as such appear in esterified carboxy(lower)alkyl and N-substituted carbamoyl(lower)alkyl within the definition of $R_1$, may have any of the meanings cited above for said terms.

Any prodrug derivatives of compounds of this invention e.g. any pharmaceutically acceptable esters and amides of the mono- or di-carboxylic acids of this invention that may be convertible by solvolysis or under physiological conditions to the said carboxylic acids e.g. esters and amides cited above, represent a particular object of the invention.

Said esters are preferably, e.g., the straight chain or branched lower alkyl esters unsubstituted or suitably substituted such as the pivaloyloxymethyl, bornyloxycarbonylmethyl, benzyl, pyridylmethyl, α-carboxyethyl or suitably esterified α-carboxyethyl esters, and the like.

Said amides are preferably e.g. simple primary and secondary amides and amides derived from the amino acids or derivatives thereof, such as the amides derived from alanine, phenylalanine and the like.

More particularly, the invention relates to compounds of formula IA

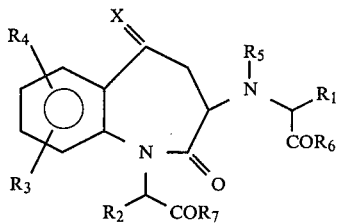

(IA)

wherein the carbocyclic ring may also be hexahydro;

$R_1$ is hydrogen, lower alkyl, amino(lower)alkyl, aryl, aryl(lower)alkyl, cycloalkyl, cycloalkyl(lower)alkyl, acylamino(lower)alkyl, mono- or di-(lower)alkylamino(lower)alkyl, lower alkylthio(lower)alkyl, carboxy(lower)alkyl, esterified carboxy(lower)alkyl, carbamoyl(lower)alkyl, N-substituted carbamoyl(lower)alkyl, hydroxy(lower)alkyl, etherified or acylated hydroxy(lower)alkyl, aryloxy(lower)alkyl, arylthio(lower)alkyl, aryl-N-(lower)alkylamino(lower)alkyl, or arylamino(lower)alkyl;

$R_2$ and $R_5$ represent hydrogen or lower alkyl;

$R_3$ and $R_4$ represent hydrogen, lower alkyl, lower alkoxy, lower alkanoyloxy, hydroxy, halogen, trifluoromethyl; or $R_3$ and $R_4$ taken together represent lower alkylenedioxy;

X represents oxo, two hydrogens, or one hydroxy or acylated hydroxy group and one hydrogen;

$R_6$ and $R_7$ independently represent hydroxy, amino, mono- or di-(lower)alkylamino, lower alkoxy, aryl(lower)alkoxy, lower alkanoyloxymethoxy, (amino, mono- or di-lower alkylamino, carboxy, or lower alkoxycarbonyl)-lower alkoxy; or the pharmaceutically acceptable salts or complexes thereof.

A more specific embodiment of this invention relates to compounds of formula IA wherein $R_1$ is hydrogen, lower alkyl, amino(lower)alkyl, aryl, aryl(lower)alkyl, cycloalkyl(lower)alkyl; and wherein within the above definitions aryl represents phenyl unsubstituted or mono- or di-substituted by lower alkyl, lower alkoxy, lower alkylenedioxy, lower alkanoyloxy, hydroxy, halogen or trifluoromethyl; and cycloalkyl contains 3 to 8 carbons; X and $R_2$ to $R_7$ are as defined above; or the pharmaceutically acceptable salts or complexes thereof; or said compounds wherein the carbocyclic ring is hexahydro.

A further embodiment of this invention relates to compounds of formula IA wherein $R_1$ is aryl(lower)alkyl where aryl represents indolyl, carboxy(lower)alkyl, lower alkoxycarbonyl(lower)alkyl, hydroxy(lower)alkyl, lower alkylthio(lower)alkyl, acylamino(lower)alkyl; aryloxy(lower)alkyl or arylthio(lower)alkyl; X and $R_2$ to $R_7$ are as defined above; or the pharmaceutically acceptable salts or complexes thereof; or said compounds wherein the carboxylic ring is hexahydro.

Preferred embodiments of this invention relate to compounds of formula IA wherein the carbocyclic ring may also be hexahydro; $R_1$ is hydrogen, lower alkyl, amino(lower)alkyl, acylamino(lower)alkyl, aryl(lower)alkyl where aryl represents phenyl unsubstituted or mono- or disubstituted by lower alkyl, hydroxy, lower alkoxy, lower alkylenedioxy, lower alkanoyloxy, halogen or trifluoromethyl;

$R_2$ and $R_5$ are hydrogen or lower alkyl;

$R_3$ and $R_4$ are hydrogen, lower alkoxy, lower alkyl, halogen or trifluoromethyl; or $R_3$ and $R_4$ taken together represent alkylenedioxy;

X represents oxo, one hydroxy or acylated hydroxy and one hydrogen, or 2 hydrogens;

$R_6$ and $R_7$ independently represent hydroxy, amino, lower alkoxy, phenyl(lower)alkoxy, lower alkoxycarbonyl(lower)alkoxy;

or pharmaceutically acceptable salts thereof.

Very useful as angiotensin-converting enzyme inhibitors are compounds of formula IA, wherein $R_1$ is hydrogen, lower alkyl, amino(lower)alkyl, aryl(lower)alkoxycarbonylamino(lower)alkyl, or aryl(lower)alkyl where aryl represents phenyl unsubstituted or monosubstituted by lower alkyl, hydroxy, lower alkoxy, lower alkanoyloxy, halogen or trifluoromethyl;

$R_2$ and $R_5$ are hydrogen or lower alkyl;

$R_3$ and $R_4$ are hydrogen, lower alkoxy, lower alkyl, halogen, or trifluoromethyl; or $R_3$ and $R_4$ taken together represent lower alkylenedioxy;

X represents oxo, one hydroxy or lower alkanoyloxy and one hydrogen, or 2 hydrogens;

$R_6$ and $R_7$ independently represent hydroxy, amino, lower alkoxy, phenyl(lower)alkoxy, lower alkoxycarbonyl(lower)alkoxy;

or pharmaceutically acceptable salts thereof; or said compounds wherein the carbocyclic ring is hexahydro.

Particularly useful are compounds of formula IA wherein $R_1$ is hydrogen, lower alkyl, ω-amino(lower)alkyl, ω-arylmethoxycarbonylamino-(lower)alkyl, aryl(-lower)alkyl where aryl represents phenyl unsubstituted or mono-substituted by lower alkyl, hydroxy, lower alkoxy, lower alkanoyloxy, halogen or trifluoromethyl;

$R_2$ and $R_5$ are hydrogen or lower alkyl;

$R_3$ is hydrogen;

$R_4$ is hydrogen, lower alkoxy, lower alkyl, halogen, or trifluoromethyl;

X represents oxo, one hydroxy or lower alkanoyloxy and one hydrogen, or 2 hydrogens;

$R_6$ and $R_7$ independently represent hydroxy, amino, lower alkoxy, phenyl(lower)alkoxy, lower alkoxycarbonyl(lower)alkoxy;

or pharmaceutically acceptable salts thereof; or said compounds wherein the carbocyclic ring is hexahydro.

Especially useful are compounds of formula IA wherein $R_1$ is hydrogen, methyl, ethyl, isopropyl, ω-aminopropyl, ω-aminobutyl, ω-(benzyloxycarbonylamino)propyl, ω-(benzyloxycarbonylamino)butyl, aryl-(methyl, ethyl, propyl) where aryl represents phenyl unsubstituted or substituted by one methyl, hydroxy, methoxy, methylenedioxy, acetoxy, chloro or trifluoromethyl group;

$R_2$ and $R_5$ are hydrogen or methyl;

$R_3$ and $R_4$ represent hydrogen, methoxy, methyl, chloro or trifluoromethyl;

X represents oxo, one hydroxy or one acetoxy and one hydrogen, or 2 hydrogens;

$R_6$ and $R_7$ independently represent hydroxy, amino, ethoxy, methoxy, benzyloxy, ethoxycarbonylmethoxy or pivaloyloxymethoxy;

or pharmaceutically acceptable salts thereof; or said compounds wherein the carbocyclic ring is hexahydro.

Exceedingly useful are compounds of formula IB (IB)

wherein the carboxylic ring may also be hexahydro;

n represents an integer from 1 to 4;

$R_8$ is hydrogen, amino, benzyloxycarbonylamino, phenyl unsubstituted or monosubstituted by lower alkyl, lower alkoxy, lower alkanoyloxy, halogen, hydroxy, or trifluoromethyl;

$R_6$ and $R_7$ independently represent hydroxy, lower alkoxy of up to 4 carbon atoms, benzyloxy, amino; or pharmaceutically acceptable salts thereof.

Especially valuable are compounds of formula IB wherein $C_nH_{2n}$ represents ethylene; $R_8$ represents phenyl or phenyl monosubstituted by lower alkoxy with up to 4 carbon atoms, lower alkyl with up to 4 carbon atoms, halogen or trifluoromethyl;

$R_6$ and $R_7$ independently represent hydroxy or lower alkoxy with up to 4 carbon atoms;

or pharmaceutically acceptable salts thereof; or said compounds wherein the carbocyclic ring is hexahydro.

Also preferred are compounds of formula IB wherein $C_nH_{2n}$ represents n-propylene or n-butylene; $R_8$ represents amino or benzyloxycarbonylamino; $R_6$ and $R_7$ independently represent hydroxy or lower alkoxy with up to 4 carbon atoms; or pharmaceutically acceptable salts thereof; or said compounds wherein the carboxyclic ring is hexahydro.

The present invention also relates to the stereoisomers of compounds of formula I. A number of racemates are obtainable when, e.g. in formula IA at least one of $R_1$ and $R_2$ is not hydrogen and/or X represents H(OH) or H(acylated OH). Furthermore, the compounds of the invention in which the carbocyclic ring is hexahydro may also exist as the isomers with either a cis or trans ring junction.

The individual enantiomers of said racemates may in turn be obtained. Certain specific said isomers are preferred as angiotensin-converting enzyme inhibitors.

Preferred are said compounds in which the asymmetric ring carbon (position 3) bearing the substituted amino group is of the (S)-configuration. Further preferred are said compounds in which the side chain asymmetric carbon atom bearing the $COR_6$ group is of the (S)-configuration.

Outstanding are compounds of formula IC (IC)

wherein S represents the chirality, n represents an integer from 1 to 4;

$R_8$ is hydrogen, amino, benzyloxycarbonylamino, phenyl unsubstituted or monosubstituted by lower alkyl, lower alkoxy, lower alkanoyloxy, halogen, hydroxy, or trifluoromethyl;

$R_6$ and $R_7$ independently represent hydroxy, lower alkoxy of up to 4 carbon atoms, benzyloxy, amino; or pharmaceutically acceptable salts thereof.

The general definitions used herein have the following meanings within the scope of the present invention.

Aryl represents a carbocyclic or heterocyclic aromatic radical preferably being phenyl, unsubstituted or mono- or di-substituted by lower alkyl, lower alkoxy, lower alkylenedioxy, lower alkanoyloxy, hydroxy, halogen or trifluoromethyl; indolyl, advantageously 3-indolyl; or indolyl, advantageously 3-indolyl, substituted by lower alkyl, lower alkoxy, lower alkylenedioxy, lower alkanoyloxy, hydroxy, halogen or trifluoromethyl respectively.

The term cycloalkyl represents a cyclic hydrocarbon radical which preferably contains 3 to 8 carbons and is, for example, cyclopentyl or cyclohexyl.

The term aryl(lower)alkyl represents preferably benzyl, 1- or 2-phenylethyl, 1-, 2- or 3-phenylpropyl, 1-, 2-, 3- or 4-phenylbutyl, wherein the phenyl ring is unsubstituted or mono- or disubstituted by lower alkyl, hydroxy, lower alkoxy, lower alkylenedioxy, lower alkanoyloxy, halogen or trifluoromethyl; also indolylmethyl advantageously 3-indolylmethyl, 1- or 2-indolylethyl advantageously 2-indolylethyl.

The term cycloalkyl(lower)alkyl represents preferably 1 or 2-(cyclopentyl or cyclohexyl)ethyl, 1-, 2- or 3-(cyclopentyl or cyclohexyl)propyl, or 1-, 2-, 3- or 4-(cyclopentyl or cyclohexyl)-butyl.

The term "lower" referred to above and hereinafter in connection with organic radicals or compounds respectively defines such with up to and including 7, preferably up and including 4 and advantageously one or two carbon atoms.

A lower alkyl group contains 1–7 carbon atoms, preferably 1–4 carbon atoms and represents for example ethyl, propyl, butyl or advantageously methyl.

A lower alkoxy group preferably contains 1–4 carbon atoms and represents for example methoxy, propoxy, isopropoxy or advantageously ethoxy. A mono-(lower)alkylamino group preferably contains 1–4 carbon atoms in the alkyl portion and is for example N-methylamino, N-propylamino or advantageously N-ethylamino. A di-(lower)alkylamino group preferably contains 1–4 carbon atoms in each lower alkyl portion and represents, for example, N,N-dimethylamino, N-methyl-N-ethylamino and advantageously N,N-diethylamino.

Lower alkanoyloxy represents preferably acetoxy, propionoxy or pivaloyloxy.

Alkylenedioxy represents preferably ethylenedioxy, and advantageously methylenedioxy.

Aryl(lower)alkoxy represents advantageously e.g. benzyloxy, benzyloxy substituted by methyl, methoxy or chloro, and pyridylmethoxy.

Carboxy(lower)alkoxy represents advantageously e.g. 1-carboxyethoxy.

Lower alkoxycarbonyl(lower)alkoxy represents advantageously e.g. 1-(ethoxycarbonyl)ethoxy.

Amino(lower)alkoxy, mono-(lower)alkylamino(lower)alkoxy, di-(lower)alkylamino(lower)alkoxy advantageously represent respectively e.g. aminoethoxy, ethylaminoethoxy, diethylaminoethoxy.

Lower alkanoyloxymethoxy represents advantageously e.g. pivaloyloxymethoxy.

Bicycloalkyloxycarbonyl-(lower)alkoxy preferably represents bicyclo[2,2,1]heptyloxycarbonyl-(lower)alkoxy unsubstituted or substituted by lower alkyl, advantageously bornyloxycarbonylmethoxy.

Amino(lower)alkyl and ω-amino(lower)alkyl represent preferably amino(ethyl,propyl or butyl) and ω-amino(ethyl, propyl or butyl) respectively.

Halogen preferably represents chlorine, but may also be bromine, fluorine or iodine.

Acylated hydroxy represents preferably lower alkanoyloxy e.g. acetyloxy, benzoyloxy, benzoyloxy substituted on the phenyl ring by lower alkyl, halogen or lower alkoxy, e.g. methyl, chloro or methoxy respectively, or nicotinoyloxy.

Etherified hydroxy represents preferably lower alkoxy e.g. methoxy, or benzyloxy.

Aryloxy represents preferably phenoxy or phenoxy substituted by lower alkyl, lower alkoxy or halogen, e.g. methyl, methoxy or chloro respectively.

Arylthio represents preferably phenylthio or phenylthio substituted by lower alkyl, lower alkoxy or halogen, e.g. methyl, methoxy or chloro respectively.

Arylamino represents preferably anilino; aryl-N-(lower)alkylamino represents preferably N-methylanilino.

Acylamino-lower alkyl and ω-acylamino-lower alkyl represent preferably acylamino(ethyl, propyl or butyl) and ω-acylamino(ethyl, propyl or butyl) respectively.

Acylamino represents lower alkanoylamino, lower alkoxycarbonylamino, cycloalkylcarbonylamino, cycloalkyloxycarbonylamino, cycloalkyl(lower)alkoxycarbonylamino; also aryl(lower)alkanoylamino, aryl(lower)alkoxycarbonylamino, arylsulfonamido in which aryl preferably represents phenyl or phenyl substituted by preferably lower alkyl, lower alkoxy or halogen; also aroylamino in which aroyl preferably represents benzoyl, or benzoyl substituted by preferably lower alkyl, lower alkoxy or halogen, or nicotinoyl.

Aryl(lower)alkoxycarbonylamino represents preferably arylmethoxycarbonylamino, advantageously benzyloxycarbonylamino (also called carbobenzyloxyamino), benzyloxycarbonylamino substituted on the phenyl ring by lower alkyl, lower alkoxy or halogen, e.g. methyl, methoxy or chloro respectively, or pyridylmethoxycarbonylamino.

According to the present invention one or both of the carboxyl groups of the dicarboxylic acids, i.e. compounds of formula IA, IB or IC wherein $R_6$ and $R_7$ are hydroxy, may be functionalized as esters or amides. These functional derivatives are preferably the mono or bis lower alkyl esters e.g. methyl, ethyl, n- or i-propyl, butyl or benzyl esters; the mono- or bis-amides, the mono- or di-N-alkylated amides, e.g. mono- or diethylamides; the mono or di-substituted lower alkyl esters, e.g. the ω-(amino, mono- or dimethylamino, carboxy or carbethoxy) -(ethyl, propyl or butyl)esters. Highly preferred functional derivatives are the mono esters of formula IA, e.g. wherein one of $R_6$ and $R_7$ represents hydroxy and the other represents lower alkoxy.

Pharmaceutically acceptable salts are preferably metal or ammonium salts of said compounds of formula I wherein $R_o$ represents carboxy or of formula IA wherein $COR_6$ and/or $COR_7$ represent carboxy, more particularly alkali or alkaline earth metal salts, e.g., the sodium, potassium, magnesium or calcium salt; or advantageously easily crystallizing ammonium salts derived from ammonia or organic amines, such as mono-, di- or tri-lower(alkyl, cycloalkyl or hydroxyalkyl)amines, lower alkylenediamines or lower hydroxyalkyl or aralkyl)alkylammonium bases, e.g., methylamine, diethylamine, triethylamine, dicyclohexylamine, triethanolamine, ethylenediamine, tris-(hydroxymethyl)aminomethane or benzyltrimethylammonium hydroxide. Said compounds of Formula I form acid addition salts, which are preferably such of therapeutically acceptable inorganic or organic acids, such as strong mineral acids, for example hydrohalic, e.g. hydrochloric or hydrobromic acid; sulfuric, phosphoric, nitric or perchloric acid; aliphatic or aromatic carboxylic or sulfonic acids, e.g., formic, acetic, propionic, succinic, glycolic, lactic, malic, tartaric, gluconic, citric, ascorbic, maleic, fumaric, hydroxymaleic, pyruvic, phenylacetic, benzoic, 4-aminobenzoic, anthranilic, 4-hydroxybenzoic, salicylic, 4-aminosalicylic, pamoic, nicotinic;

methanesulfonic, ethanesulfonic, hydroxyethanesulfonic, benzenesulfonic, p-toluenesulfonic, naphthalenesulfonic, sulfanilic or cyclohexylsulfamic acid.

The compounds of formula I exhibit valuable pharmacological properties, e.g. cardiovascular effects, by inter alia inhibiting the release of Angiotensin II through selective inhibition of angiotensin-converting enzyme in mammals. The compounds are thus useful for treating diseases responsive to angiotensin-converting enzyme inhibition in mammals including man.

The compounds of this invention exhibit primarily hypotensive/antihypertensive and cardiac effects inter alia due to their angiotensin-converting enzyme inhibitory activity. These properties are demonstrable by in vivo or in vitro tests, using advantageously mammals, e.g., rats, cats, dogs or isolated organs thereof, as test objects. The animals may either be normotensive or hypertensive e.g., genetically spontaneous hypertensive rats, or renal hypertensive rats and dogs, and sodium-depleted dogs. The compounds can be applied to the test animals enterally or parenterally, advantageously orally or intravenously, for example within gelatin capsules or in the form of starchy suspensions or aqueous solutions. The applied dosage may range between about 0.01 and 100 mg/kg/day, preferably between about 0.05 and 50 mg/kg/day, advantageously between about 0.1 and 25 mg/kg/day.

The in vivo lowering effect on the blood pressure is recorded, either directly by means of a catheter, placed in the test animal's femoral artery, or indirectly by sphygmomanometry at the rat's tail or a transducer. The blood pressure is recorded in mm Hg prior to and after dosing.

Thus the antihypertensive effects are demonstrable in spontaneously hypertensive rats by indirect measurement of systolic pressure. Conscious rats are placed individually in restraint cages within a gently warmed chamber. A rubber pulse sensor is placed distal to an inflatable occlusive cuff on each rat's tail. The cuff is periodically inflated to occlude the tail artery, and systolic pressure is recorded as the point where the first discernible pulse emerges along the decaying calibrated pressure curve. After obtaining control values of blood pressure and heart rate, test compounds are administered orally once daily for 4 consecutive days. Additional blood pressure measurements are usually made at 2.0, 4.0 and 23.5 hours after each daily dosing, and responses are compared to those of rats dosed with the treatment vehicle.

Illustrative of the invention, the "higher melting" 1-carboxymethyl-3-(1-ethoxycarbonyl-3-phenyl-propylamino)-2,3,4,5-tetrahydro-1H[1]benzazepin-2-one of example 1 at a dose of 3 mg/kg p.o. lowers blood pressure by 40 mm Hg as the average effect measured at 2 and 4 hours after the last two daily dosings. The corresponding S,S enantiomer of example 12 at a dose of 1 mg/Kg p.o. lowers blood pressure by 30 mm Hg.

The compounds of this invention when administered intravenously or orally also exhibit an inbibitory effect against the Angiotensin I induced pressor response of normotensive rats. Angiotensin I is hydrolyzed by the action of said converting enzyme to the potent pressor substance Angiotensin II. The inhibition of said enzyme prevents the generation of Angiotensin II from I and, therefore, attenuates any pressor response following an Angiotensin I challenge.

The corresponding in vivo test is performed with male, normotensive rats, which are anesthetized with sodium 5-ethyl-5-(1-methylpropyl)-2-thiobarbiturate. A femoral artery and saphenous vein are cannulated respectively for direct blood pressure measurement and the i.v. administration of Angiotensin I and a compound of this invention. After the basal blood pressure is stabilized, pressor responses to 3 challenges of 333 ng/kg angiotensin I i.v., at 5 minute intervals, are obtained. Such pressure responses are usually again obtained at 5, 10, 15, 30 and 60 minutes after i.v. administration or 1, 2, 3 and 4 hours after p.o. administration of the compound to be tested, and compared with the initial response. Any observed decrease of said pressor response is an indication of Angiotensin I converting enzyme inhibition. Illustrative of this invention, the "higher melting" 1-carboxymethyl-3-(1-ethoxycarbonyl-3-phenylpropylamino)-2,3,4,5-tetrahydro-1H[1]benzazepin-2-one of example 1 and the corresponding S,S, enantiomer of example 12 completely inhibit the pressor response following Angiotensin I challenge through 30 minutes after administration of either of the said compounds at a dose of 1 mg/kg i.v.

Further illustrative of the invention, 1-carboxymethyl-3S-(1-ethoxycarbonyl-3-phenylpropylamino)-2,3,4,5,5a,6,7,8,9,9a-decahydro-1H-[1]benzazepin-2-one of example 38, and 5-acetoxy-1-carboxymethyl-3S-(1-ethoxycarbonyl-3-phenylpropylamino)-2,3,4,5-tetrahydro-1H-[1]benzazepin-2-one hydrochloride of example 39 inhibit the pressor response following angiotensin I challenge by about 70% at an oral dose of 1 mg/Kg and 3 mg/Kg, respectively, as measured 2 to 4 hours after administration.

The in vitro inhibition of the angiotensin-converting enzyme by the compounds of this invention can be demonstrated by a method analogous to that given in Biochim. Biophys. Acta 293, 451 (1973). According to this method, said compounds are dissolved at about 1 mM concentration in phosphate buffer. To 100 microliters of solutions of the test compound in phosphate buffer, diluted to the desired concentration, are added 100 microliters of 5 mM hippuryl-histidyl-leucine in phosphate buffer, followed by 50 microliters of the angiotensin-converting enzyme preparation (from lungs of adult male rabbits) in Tris buffer, containing potassium and magnesium chloride, as well as sucrose. Said solutions are incubated at 37° C. for 30 minutes and combined with 0.75 ml of 0.6N aqueous sodium hydroxide to stop further reaction. Then 100 microliters of a 0.2% solution of o-phthalaldehyde in methanol are added at room temperature, and 10 minutes later 100 microliters of 6N hydrochloric acid. These samples are read against water in a spectrophotometer set at 360 nm, and the optical densities thereof estimated. They are corrected for the standard curve via a conversion factor expressing nanomoles of histidyl-leucine formed during said 30 minute incubation period. The results are plotted against drug concentration to determine the $IC_{50}$, i.e., the drug concentration which gives half the activity of the control sample containing no drug. Illustrative of the invention, the "higher melting" 1-carboxymethyl-3-(1-carboxy-3-phenylpropylamino)-2,3,4,5-tetrahydro-1H[1]benzazepin-2-one of example 9 and the corresponding S,S enantiomer of example 19 show an $IC_{50}$ of $5.2 \times 10^{-9}$M and $1.7 \times 10^{-9}$M respectively. The corresponding "lower melting" 1-carboxymethyl-3-(1-carboxy-3-phenylpropylamino)-2,3,4,5-tetrahydro-1H[1]benzazepin-2-one of example 8 shows an $IC_{50}$ of $5.8 \times 10^{-8}$M. 3-[(5-Benzyloxycarbonylamino-1-carboxy)pentylamino]-1-carboxymethyl-2,3,4,5-tetrahydro-1H[1]benzazepin-2-one hydrochloride (Isomer B) of example 41b shows an IC$_{50}$ of $1.2 \times 10^{-8}$M.

Angiotensin-converting enzyme not only participates in the conversion of Angiotensin I to Angiotensin II, but also plays a role in the control of bradykinin and aldosterone levels. The effect of the compounds of this invention on these factors may also contribute to the antihypertensive and cardiac effects of the compounds of this invention.

The aforementioned advantageous properties render the compounds of this invention of great value as specific therapeutic agents for mammals including man.

Accordingly, the compounds of this invention are valuable antihypertensive agents, especially useful for ameliorating hypertension (regardless of etiology) and/or cardiac conditions, such as congestive heart failure, and/or other edemic or ascitic diseases. They are also useful in the preparation of other valuable products, especially of corresponding pharmaceutical compositions.

The compounds of formula I according to the invention can be prepared in a manner which is known per se, in that, e.g.

(a) in a compound of the formula

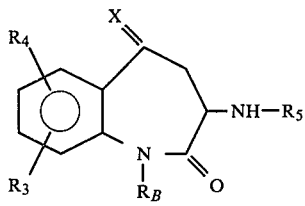

(II)

in which the carbocyclic ring may also be hexahydro or 6,7,8,9-tetrahydro, and wherein X, R$_B$, R$_3$, R$_4$ and R$_5$ have the meanings given hereinabove, R$_A$ is introduced by alkylation with a compound of the formula

(IIIA)

wherein Z is a reactive esterified hydroxyl group and R$_A$ has the meanings given hereinabove or with a compound of the formula

(IV)

wherein R$_1$ and R$_o$ have meanings given hereinabove, in the presence of a reducing agent with temporary protection of any primary and secondary amino groups and/or, optionally, hydroxyl and/or oxo groups, which may be present in any one of the residues X, R$_B$, R$_3$, R$_4$ and R$_5$, and/or in the alkylating agent, or (b) a compound of the formula

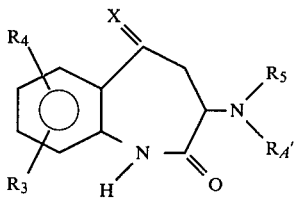

(V)

in which the carboxylic ring may also be hexahydro or 6,7,8,9-tetrahydro, and wherein X, R$_3$, R$_4$ and R$_5$ have the meanings given hereinabove and R$_A'$ is hydrogen or R$_A$ as defined hereinabove, is alkylated with a compound of the formula

(IIIB)

wherein Z is a reactive esterified hydroxyl group and R$_B$ has the meanings given hereinabove, while protecting temporarily any primary and secondary amino groups and/or, optionally, hydroxyl and/or oxo groups which may be present in any one of the residues X, R$_A$, R$_B$, R$_3$, R$_4$ and R$_5$, or (c) a compound of the formula

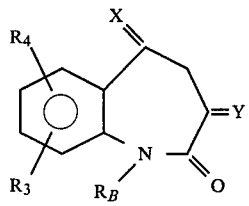

(VI)

in which the carbocyclic ring may also be hexahydro or 6,7,8,9-tetrahydro and wherein Y is oxo or a reactive esterified hydroxyl group Z together with hydrogen, and X, R$_B$, R$_3$ and R$_4$ have the meanings given hereinabove, is condensed with an amine of the formula

(VII)

wherein R$_A$ and R$_5$ have the meanings given hereinabove, with the proviso that when Y is oxo, the condensation is carried out in the presence of a reducing agent and with a temporary protection of the oxo group which may be present as the substituent X, or (d) in a compound of the formula

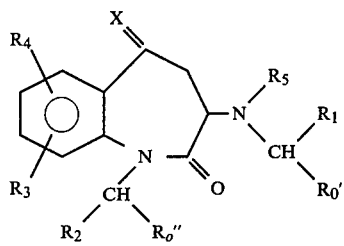

(VIII)

in which the carbocyclic ring may also be hexahydro or 6,7,8,9-tetrahydro, and wherein X and R$_1$, to R$_5$ have the meanings given hereinabove, one of the symbols R$_o'$ and R$_o''$ is cyano and the other one is cyano or R$_o$ as defined hereinabove, the cyano group(s) is (are) subject to solvolysis, or (e) compound of the formula

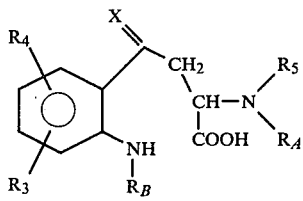

(IX)

in which the carbocyclic ring may also be hexahydro or 6,7,8,9-tetrahydro and wherein X, R$_A$, R$_B$, R$_3$, R$_4$ and R$_5$ have the meanings given hereinabove, or an ester thereof, is cyclised, or (f) a compound which is structurally identical with a compound of formula I specified above, except for having an additional double bond located at C-3, or between the nitrogen atom and the adjacent carbon atom within the group $R_A$, is treated with a reducing agent in order to saturate this double bond, or (g) in order to produce a compound of formula I as specified hereinabove, in which X is oxo, condensing a compound of the formula

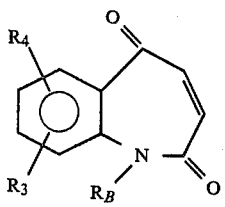
(X)

in which the carbocyclic ring may also be hexahydro or 6,7,8,9-tetrahydro, and wherein $R_B$, $R_3$ and $R_4$ have the meanings given hereinabove, with an amine of the formula

(VII)

wherein $R_A$ and $R_5$ have the meaning given hereinabove, and (h) if desired, a resulting compound of formula I as specified above is converted into another compound of formula I within its above-specified scope, and/or (i) if desired, a resulting compound of formula I as specified above and having salt-forming properties is converted into a salt thereof or a free compound is liberated from such a salt, and/or (j) if desired, a resulting compound of formula I as specified above and having complex-forming properties is converted into a complex thereof, and/or (k) if so required, an optical isomer which has a specific configuration with respect to at least one center of chirality is enriched from a mixture of stereoisomeric forms of a resulting compound of formula I.

The alkylation according to processes (a) and (b), which serves for introduction of residues $R_A$ and $R_B$, respectively, is carried out in a conventional manner, advantageously by treating a corresponding starting material of formula II or V, respectively, with an alkylating agent of the formula $R_A$—Z (IIIA) or $R_B$—Z (IIIB), respectively, wherein $R_A$ or $R_B$ have the meanings given hereinabove and Z is a reactive esterified hydroxyl group, such as a hydroxyl group esterified with a strong organic acid, e.g. an aliphatic or aromatic sulfonic acid (such as a lower alkanesulfonic acid, especially methanesulfonic, trifluoromethanesulfonic acid, especially benzenesulfonic, p-toluenesulfonic, p-bromobenzenesulfonic and p-nitrobenzenesulfonic acid) or with a strong inorganic acid, such as, especially, sulfuric acid, or a hydrohalic acid, such as hydrochloric or, most preferably, hydriodic or hydrobromic acid. The alkylation is carried out under conventional general conditions at temperatures ranging between about 0° C. up to the boiling temperature of the reaction mixture, preferably at temperatures between room temperature to about 100° C. The reaction takes place advantageously in the presence of a solvent which is inert with respect to the reactants, such as a chlorinated lower alkane (e.g. chloroform or methylene chloride), an acyclic or cyclic ether (e.g. diethyl ether, 1,2-dimethoxyethane, dioxane or tetrahydrofuran) and, in particular, a low molecular weight tertiary amide (e.g. N,N-dimethylformamide, N,N-dimethylacetamide, N-methylpyrrolidone, N-ethylpiperidone and hexamethylphosphoric acid triamide). Advantageously, the strong acid HZ liberated during the reaction is bound by the addition of an acid-binding agent, such as, preferably, an inorganic acid-scavenger such as an alkali metal bicarbonate, carbonate or hydroxide, an organic quaternary ammonium salt (e.g. a tetrabutylammonium salt) or an organic tertiary base, such as triethylamine, N-ethylpiperidine, pyridine or quinoline.

In process (a), the alkylation can also be carried out under the conditions of reductive alkylation in the manner generally known and used in the art. In carrying out the alkylation, a compound of the general formula

(IV)

in which $R_1$ and $R_o$ have the meanings given hereinabove, is reacted with the starting bicyclic compound II and, simultaneously or in a subsequent step, with a reducing agent. Among reducing agents which are used simultaneously with the alkylating agent, mention should be made of formic acid and complex metal hydrides such as sodium cyanoborohydride; among reducing agents used predominantly in a separate subsequent operation i.e. reduction of a preformed imine (Schiff's base), mention should be made of diborane and complex metal hydrides, such as, sodium borohydride, sodium cyanoborohydride which are added advantageously to the primary reaction mixture without isolating an intermediate, e.g. the imine. In this case, the alkylation is carried out advantageously in an organic solvent inert to the reducing agent, such as in an aliphatic or cyclic ether (such as diethyl ether, diisopropyl ether, 1,2-dimethoxyethane, dioxane or tetrahydrofuran) or an aliphatic alcohol (such as methanol, ethanol, isopropyl alcohol, glycol, glycol monomethyl ether or diethyleneglycol), preferably at about 0°–80° C. A principal reducing agent, however, which can be used both simultaneously and subsequently, is hydrogen, especially catalytically activated hydrogen. The catalysts are those conventionally used as hydrogenation catalysts, i.e. preferably those of the class of precious metals (such as palladium, platinum and rhodium) on a carrier (such as calcium carbonate, aluminum oxide or barium sulfate), in a finely dispersed suspension without carrier or, in form of complexes, in a homogeneous phase. Also, finely dispersed transition metals such as Raney metals, especially Raney nickel, are very suitable catalysts for the reductive alkylation. The specific reaction conditions depend, to a large extent, on the particular hydrogenation catalyst and its precise activity, and do not differ from those generally known for hydrogenation. Temperatures ranging from room temperature to about 150° C., and pressures of hydrogen ranging from atmospheric pressure to about 300 atmospheres are applicable according to the standard procedures of the art. In addition to the inert solvents which were mentioned above in connection with the hydride reduction, low molecular weight amides, especially tertiary amides (such as N,N-dimethylformamide, N,N-dimethylacetamide, N-methylpyrrolidone, N-ethylpiperidone, hexamethylphosphoric acid triamide), and also formamide and acetamide can be used as suitable solvents. Special measures have to be taken with starting materials of formula II which have an easily reducible functional group, such as the 5-oxo group; in order to preserve these groups, selective reduction conditions, as known in the prior art, have to be applied, or, if a simultaneous reduction of these groups is desired or required, vigorous reagents and/or conditions are employed accordingly.

The preformed imines referred to above are preferably prepared by condensing an amine of formula II with a compound of formula IV in an inert solvent, e.g. toluene or methylene chloride, advantageously in the presence of a dehydrating catalyst, e.g. boron trifluoride etherate, p-toluenesulfonic acid or molecular sieves.

Process (b) is preferably carried out in the presence of very strong bases, such as alkali metal hydrides (e.g. sodium or potassium hydride), alkoxides (e.g. sodium methoxide or ethoxide, potassium tert-butoxide) or amides (e.g. lithium diisopropylamide), whereby ethers and amides mentioned above are preferred as solvents. In a special modification of process (b), starting materials are used in which $R_A'$ is hydrogen, and at least two equivalents of the reactant IIIB is employed. In the resulting product, both $R_A$ and $R_B$ are identical and within the scope of the meanings of $R_B$.

In any of the alkylation processes, primary and secondary amino groups in starting materials, except for the secondary amino group to be alkylated, must be in a temporarily protected form during the alkylation. Suitable protecting groups, as well as procedures for their introduction and removal are well known in the art, being elaborated in great detail in particular as general methods for the synthesis of peptides, cf. Houben-Weyl: Methoden der organischen Chemie; 4th edition, vol. 15/I and II, E. Wunsch (editor): Synthese von Peptiden (Georg Thieme Verlag, Stuttgart; 1974). The narrower selection of the protecting groups depends on the specific purpose, it being necessary to take into account in particular the specific properties of the particular starting materials and the reaction conditions of the specific process. In the case of several functional groups to be protected, advantageous combinations can be selected. Preferably, for example, similar or, even better, identical amino protecting groups, are used both in the radicals $R_o$ and in the radical $R_1$ and are simultaneously removed following alkylation.

Suitable as amino-protecting groups are especially amino-protecting groups that can be removed by reduction, for example especially those of the benzyloxycarbonyl type in which the benzyloxycarbonyl group may be substituted in the aromatic moiety by halogen atoms, lower alkoxy groups and/or lower alkyl radicals and, especially, by nitro groups, such as the p-chloro- and p-bromobenzyloxycarbonyl, p-methoxybenzyloxycarbonyl, p-methylbenzyloxycarbonyl and, especially, p-nitrobenzyloxycarbonyl group, or alternatively the isonicotinyloxycarbonyl group. An advantageous amino-protecting group is an ethoxycarbonyl group which carries in the $\beta$-position a silyl group substituted by these hydrocarbon radicals, such as triphenylsilyl, dimethyl-tert.-butylsilyl or, especially, trimethylsilyl. A $\beta$-(trihydrocarbylsilyl)-ethoxycarbonyl group of this type, such as a $\beta$-(tri-lower alkylsilyl)-ethoxycarbonyl group, for example, especially $\beta$-(trimethylsilyl)-ethoxycarbonyl, forms with the amino group to be protected a corresponding $\beta$-trihydrocarbylsilylethoxycarbonylamino group (for example the $\beta$-trimethylsilylethoxycarbonylamino group), which may be removed under very specific, very mild conditions by the action of fluoride ions.

It is also possible to use groups that can be removed by acidolysis, such as the tert-butoxycarbonyl groups and analogous groups, as well as those of the aralkyl type, such as benzhydryl, di-(4-methoxy)-benzhydryl and triphenylmethyl (trityl), or certain aralkoxycarbonyl groups of the 2-(p-biphenylyl)-2-propoxycarbonyl type, which are described in Swiss Patent Specification No. 509 266. It should be noted that protecting groups derived from esters of carbonic acids are in most cases also removable by basic hydrolysis.

For the optional temporary protection of hydroxy groups, protecting groups may be used advantageously that can be removed by reduction, cf. the above-cited text (Houben-Weyl), and also groups that can be removed by acidolysis, such as 2-tetrahydropyranyl, tert-butoxycarbonyl and tert-butyl. Preferred hydroxy-protecting groups that can be removed by reduction are, for example, benzyl groups that may be substituted in the aromatic moiety by halogen, lower alkyl, lower alkoxy and/or, especially, nitro, especially the 4-nitrobenzyl group. It is also possible to use acyl groups that can be removed under weakly basic conditions, such as formyl or trifluoroacetyl.

For the optional protection of oxo groups, these are preferably protected as ketals, especially as ketals derived from lower alkanols, such as methanol or ethanol, or advantageously of ethylene glycol, or as corresponding thioketals preferably those of 1,2-ethanedithiol. All these groups can liberate oxo groups under the conditions indicated further below.

The subsequent removal of protecting groups in accordance with the invention depends on their nature and is carried out in each case in a conventional manner known per se taking into consideration the general properties of the derived product. If the protecting groups for amino, hydroxy and oxo have been so selected that they can be removed under similar conditions (especially preferred here are the groups removable by acidolysis or, for amino and hydroxy, by reduction, that have already been given special mention), then all of these protecting groups are advantageously removed in a single operation; in special cases, however, it is possible to use different types of groups and remove each of them individually.

The groups that can be removed by reduction, especially those that contain halogenated lower alkyl radicals (for example 2,2,2-trichloroethyl radicals), isonicotinyl radicals (for example isonicotinyloxycarbonyl) and, especially, substituted benzyl radicals, especially 4-nitrobenzyl radicals of any kind, are preferably removed by zinc reduction, usually in the presence of an acid, preferably acetic acid, and with or without the addition of an inert organic solvent, usually at room temperature. The removal of a protecting group by acid hydrolysis (acidolysis) is carried out in the case of groups of the tert-butyl type by means of hydrogen chloride, hydrogen fluoride or trifluoroacetic acid, and in the case of acid-sensitive protecting groups chiefly by means of a lower aliphatic carboxylic acid, such as formic acid and/or acetic acid, in the presence of water and, optionally, a polyhalogenated lower alkanol or lower alkanone, such as 1,1,1,3,3,3-hexafluoropropan-2-ol or hexafluoroacetone. In this manner it is possible, for example, for an N-trityl group to be removed by an organic acid, such as formic acid, acetic acid, chloroacetic acid or trifluoroacetic acid, in aqueous or absolute trifluoroethanol as solvent (cf. German Offenlegungsschrift DT 2 346 147) or by aqueous acetic acid;

for the tert-butoxycarbonyl group to be removed by trifluoroacetic acid or hydrochloric acid; and for the 2-(p-biphenylyl)-isopropoxycarbonyl group to be removed by aqueous acetic acid or, for example, by a mixture of glacial acetic acid, formic acid (82.8% strength) and water (7:1:2) or in accordance with the process in DT No. 2 346 147. The β-silylethyl ester groups are preferably removed by fluoride ion-yielding reagents, for example fluorides of quaternary organic bases, such as tetraethylammonium fluoride.

Ketalized and thioketalized oxo groups are converted into free oxo groups by acidolysis with usual strong inorganic acids, or with oxalic acid, in the presence of water, the latter ones advantageously by treatment with a sulfur-binding agent, e.g. a mercury II-salt and/or cadmium carbonate. Protecting groups that are unstable to basic conditions, for example formyl, trifluoroacetyl and carbonic acid ester groups, can be carefully removed by the action of an aqueous sodium or potassium bicarbonate or carbonate solution or, also, aqueous ammonia, in an organic solvent, usually at room temperature. The protecting groups are preferably removed under the reaction conditions of the examples, or under analogous conditions.

Those of the end products according to the invention that contain basic groups are obtained, depending on the manner of isolation, in the form of bases or acid addition salts; analogously, end products having acidic groups may also be obtained in the form of salts. Each form can be converted into the other in known manner. The bases can be obtained from the acid addition salts in a manner known per se. From the bases it is in turn possible to obtain acid addition salts, especially therapeutically useful acid addition salts, by reaction with acids, for example with acids of the type that form the above-mentioned salts. Acids and their salts also stand in a similar relationship to one another. Compounds that have both a free carboxy group and a basic group may be in the form of inner salts and these are obtained, for example, by establishing the isoelectric point.

The starting materials of formula IIIA, IIIB and IV, that is to say the alkylating agents, are known or, if they are unknown, can be simply obtained by conventional synthetic processes.

The starting materials of formula II and V can be obtained by conventional synthetic processes, and advantageously in the manner which is described in more detail and exemplified for specific intermediates hereinafter.

Process (c), also being an alkylation reaction is performed according to the same general considerations and under the same experimental conditions as the above processes (a) and (b) as described in detail above for the treatment with an alkylating agent of formula IIIA, IIIB or IV (i.e. substitutive alkylation or reductive alkylation). Starting materials of formula VI can be obtained by conventional processes known per se, e.g. in the manner described more specifically hereinafter. The amines of formula VII are known, or if unknown, they are easily accessible by conventional synthetic methods.

Process (d) is also carried out in a conventional manner under the general conditions of solvolysis, which are known to convert cyanides (nitriles) into free carboxylic acids or their salts, esters or amides. For conversion into a free acid, hydrolysis with water is carried out advantageously in an inert organic solvent which is at least partially miscible with water, such as an ether (e.g. diethyl or diisopropyl ether, 1,2-dimethoxyethane or, especially dioxane or tetrahydrofuran) or a lower alkanol (e.g. methanol, ethanol, isopropyl alcohol, a butyl alcohol, especially tert-butyl alcohol), a larger amount of water being required in the latter cases in order to prevent alcoholysis. The hydrolysis can be catalysed both by strong acids, especially inorganic acids such as sulfuric acid or, preferably hydrohalic acids (e.g. hydrobromic or, as a first choice, hydrochloric acid), or by bases, especially inorganic bases such as hydroxides and carbonates of alkali metals, e.g. sodium and potassium hydroxide. The bases are usually employed in at least stoichiometric quantities giving rise to carboxylic acid salts as primary products. The acidic catalysts are advantageously applied as dilute aqueous solution for the best result. Final products of formula I, in which $R_0$ represents an esterified carboxyl group, can be obtained by carrying out the solvolysis of the nitrile with the corresponding alcohol (alcoholysis) in the presence of a catalytic amount of an anhydrous strong acid, advantageously gaseous hydrogen chloride. Usually, excess alcohol is used as solvent; however, inert organic solvents can be added, such as acyclic and cyclic ethers (especially these mentioned above), and/or halogenated lower alkanes (especially chloroform and dichloromethane). If the alcoholysis is carried out under strictly anhydrous conditions, the primary product (imido ester) is to be hydrolyzed, advantageously by adding water to the reaction mixture; otherwise, by carrying out the alcoholysis in the presence of an approximately stoichiometric equivalent of water, the desired ester is obtained directly. In order to obtain a corresponding amide (i.e. a compound of formula I, wherein $R_0$ is carbamoyl), a corresponding nitrile of formula VIII can preferably be subjected to alkaline hydrolysis in the presence of hydrogen peroxide.

The starting materials of formula VIII can be obtained by conventional methods known per se, e.g. by a condensation analogous to that of process (c), in which a starting material of the above-defined formula VI is treated with an amine of the formula

(VII')

wherein $R_1$ and $R_5$ have the meanings given hereinabove, and which corresponds to the above-defined amine of formula VII. Also, processes (a) and (b) can analogously be used for the preparation of the nitriles of formula VIII.

The cyclization according to process variant (e) can also be carried out in the manner known per se, e.g. by dehydration. Especially useful general methods for this purpose are those developed in connection with the formation of the amide bond in peptides, as reviewed in compilative works, e.g. Houben-Weyl, Volumes 15/1 and 15/2 as cited hereinabove. According to one preferred modification, the amino group to be cyclized is rendered inactive by protonation (i.e. in the form of an acid addition salt), and the carboxyl group is converted into an activated ester, such as that with 2,4,5-trichlorophenol, pentachlorophenol, pentafluorophenol, 2-nitrophenol or, especially, 4-nitrophenol, or with an N-hydroxy compound, such as N-hydroxysuccinimide, 1-hydroxybenztriazole or N-hydroxypiperidine, or alternatively with an N,N'-disubstituted isourea, such as, especially, N,N'-dicyclohexylisourea, or a similar generally known activating agent. The cyclization is effected by basification preferably by the addition of an organic base, for example a quaternary ammonium salt, or especially a tertiary amine, such as triethylamine, N-ethylmorpholine or N-methylpiperidine, in order to reactivate the amino group to be cyclized by converting it into the unprotonated form. The reaction temperature is usually from $-20°$ to $+50°$ C., preferably approximately at room temperature, and customary solvents are used, for example, dioxan, tetrahydrofuran, acetonitrile, pyridine, dimethylformamide, dimethylacetamide, dimethylsulfoxide, N-methylpyrrolidone, hexamethylphosphoric acid triamide, as well as chloroform and methylene chloride, and expedient mixtures thereof. In a special variant of the process, the carboxy group can be directly activated in situ by the action of the free acid with a carbodiimide, such as N,N'-dicyclohexylcarbodiimide (optionally with the addition of N-hydroxysuccinimide, an unsubstituted or, for example, halogen-, methyl- or methoxy-substituted 1-hydroxybenztriazole or 4-hydroxybenzo-1,2,3-triazine-3-oxide or N-hydroxy-5-norbornene-2,3-dicarboxiimide), or with N,N'-carbonyldiimidazole.

Starting materials of formula IX can be obtained according to general methods known per se, e.g. as discussed in more specific examples hereinafter.

Also, reduction according to process (f) can be carried out in a manner generally known per se for saturation of such double bonds. More specifically, the double bond in the unsaturated starting materials corresponding to formula I can be located between C-3 and C-4 or between C-3 and the adjacent nitrogen atom, or between the nitrogen atom and the adjacent carbon atom within the group $R_4$. The saturation of the double bond is advantageously carried out by catalytic hydrogenation, e.g. under the preferred conditions discussed in detail hereinbefore, and also by metal reduction, such as zinc reduction in neutral or acidic medium, or, especially in the case of the C-N double bond, by diborane or complex hydrides such as sodium borohydride, as mentioned hereinbefore. The unsaturated starting materials for this process are obtained according to known general methods, e.g. those discussed in processes (a) and (c) and/or, in a more specific form hereinafter.

The condensation according to process (g) is carried out under conventional general conditions at temperatures ranging between about 0° C. and 100° C. in a solvent which is inert to the reactants, e.g. methylene chloride, 1,2-dimethoxyethane, N,N-dimethylformamide, optionally in the presence of a base, e.g. a tertiary amine such as triethylamine or an alkali metal hydride such as sodium hydride.

In performing the optional interconversions of a resulting final product of formula I, into another compound within the above-specified scope of formula I, transformations such as the following are carried out: an amino group is alkylated, and/or an oxo group, especially that of the symbol X, is converted into hydroxyl (plus hydrogen) or into two hydrogens by reduction and/or hydroxyl is converted into oxo by oxidation or into hydrogen by reduction, and/or a free hydroxyl or carboxyl group is liberated from its esterified form by hydrolysis or hydrogenolysis and/or a hydroxyl or amino group is acylated and/or a free carboxyl is esterified, and/or the aromatic carboxylic ring in formula I is hydrogenated to the hexahydro or the 6,7,8,9-tetrahydro form, and/or the hexahydrocarbocyclic ring is dehydrogenated to the 6,7,8,9-tetrahydro or aromatic carbocyclic ring.

All these optional interconversions are carried out by well-known conventional methods. A lower alkyl group as represented by $R_5$ can be introduced into the final product of formula I, wherein $R_5$ is hydrogen, by an alkylation reaction, using any of the modifications discussed in detail in connection with process (a). Both substitutive and reductive alkylation can be employed, the former with alkyl halides, the latter with lower aliphatic aldehydes and ketones and e.g. catalytically activated hydrogen or, in the case of formaldehyde, advantageously with formic acid as the reducing agent. By the substitutive alkylation, lower alkyl groups can also be introduced into a carbamoyl group represented by symbol $R_0$. Also, the reduction of the 5-oxo group to hydroxy is carried out in the usual manner, e.g. by using a complex metal hydride, especially a mild reagent such as an alkali metal borohydride (e.g. sodium borohydride), or according to the method of Meerwein-Ponndorf, or a modification thereof using an alkanol, especially isopropyl alcohol, as both solvent and reducing agent and a metal alkoxide, preferably one corresponding to the reducing alcohol, such as aluminum isopropoxide, as a catalyst. The reduction of the oxo group to two hydrogens can advantageously be accomplished e.g. by treatment with amalgamated zinc and hydrochloric acid, or by Raney nickel desulfurization of a corresponding dithioketal. The oxidation of hydroxyl to oxo can be preferably carried out with a derivative of hexavalent chromium such as chromic acid or its salts, with a permanganate salt (especially potassium permanganate) or under the conditions of the Oppenauer oxidation, with acetone or cyclohexanone as oxidant and aluminum isopropoxide as catalyst. Esterified hydroxyl groups are liberated in particular by methods discussed in detail hereinabove in connection with removing hydroxyl-protecting groups; the acylation of both hydroxyl and amino groups is carried out in the usual way, preferably using a corresponding acid anhydride or halide. For esterification, a carboxyl group can be reacted directly with a diazoalkane, especially diazomethane, or with a corresponding alcohol in the presence of a strong acid catalyst (e.g. sulfuric acid or an organic sulfonic acid) and/or a dehydrating agent (e.g. dicyclohexylcarbodiimide). Alternatively, the carboxyl group can be converted into a reactive derivative thereof, such as an active ester mentioned in connection with process (e), or into a mixed anhydride, e.g. with an acid halide (i.e., especially an acid chloride), and this activated intermediate reacted with the desired alcohol.

The free carboxyl group can be liberated from an esterified carboxyl in a manner generally known, especially by base-catalyzed hydrolysis. Of special interest, however, are methods capable of selectively liberating one particular carboxyl group represented by the symbols $-COR_6$ and $-COR_7$. In such a case, use can be made of a proper combination of ester groups known in the art especially as carboxyl-protecting groups and developed in a great variety in particular for the synthesis of peptides, cf. Houben-Weyl, Volumes 15/1 and 15/2 as cited hereinabove. Radicals suitable for selective removal with liberation of the carboxyl are esters derived, for example, from alcohols that yield radicals that can be removed by acidolysis, such as cyanomethyl alcohol, benzoylmethyl alcohol or tert-butyl alcohol, but especially alcohols that yield radicals which can be removed by reduction, such as 2,2,2-trichloroethanol, benzyl alcohol, and especially 4-nitrobenzyl alcohol, or alternatively isonicotinyl alcohol. An especially advantageous class of substituted alkanols are ethyl alcohols which carry in the β-position a tri-substituted silyl group, such as triphenylsilyl, dimethyltert-butylsilyl or, especially, trimethylsilyl. As is described, for example, in Belgian Pat. No. 851,576, these alcohols are particularly suitable for selective removal because the corresponding β-silylethyl esters, for example β-(trimethylsilyl)-ethyl esters, have the stability of customary alkyl esters but can be selectively removed under mild conditions by the action of fluoride ions while retaining other esterified carboxyl groups, for example alkoxycarbonyl groups.

The removal of esterifying groups depends on their nature and is carried out in each case in a conventional manner known per se taking into consideration the properties of the other radicals involved. The groups that can be removed by reduction, especially those that contain halogenated lower alkyl radicals (for example 2,2,2-trichloroethyl radicals), isonicotinyl radicals (for example isonicotinyloxycarbonyl) and, optionally substituted benzyl radicals, especially 4-nitrobenzyl radicals of any kind, are preferably removed by zinc reduction, usually in the presence of an acid, preferably acetic acid, and with or without the addition of an inert organic solvent, usually at room temperature, those of the benzyl type, especially unsubstituted benzyl esters, also by hydrogenolysis techniques conventionally used for benzyl groups.

The removal of an ester group by acid hydrolysis (acidolysis) can be carried out especially in the case of groups of the tert-butyl type, by means of hydrogen chloride, hydrogen fluoride or trifluoroacetic acid. The β-silylethyl ester groups are preferably removed by fluoride-ion-yielding reagents, for example fluorides of quaternary organic bases, such as tetraethylammonium fluoride. Ester groups that are base-unstable can be carefully removed by the rapid action of an aqueous sodium or potassium bicarbonate solution or, preferably, aqueous ammonia in an organic solvent, usually at room temperature. The ester groups are preferably removed under the reaction conditions of the examples, or under analogous conditions.

A proper combination of the ester groups can be chosen in the earlier stages of the synthesis, or by a proper choice of starting materials and reactants, e.g. in process (a), a selectively removable ester group being introduced with a carboxyl which is to be liberated in the last stage.

The compounds of formula I in general, and IA in particular, are prepared advantageously according to reaction sequence 1, which involves an advantageous selection of starting materials and intermediates, and comprises the following steps:

(a) condensing under conditions of basic catalysis, a compound of the formula

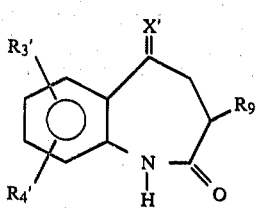

(XI)

wherein $R_3'$ and $R_4'$ represent hydrogen, lower alkyl, lower alkoxy, lower alkanoyloxy, halogen, trifluoromethyl or $R_3'$ and $R_4'$ taken together represent lower alkylenedioxy; X' presents 2 hydrogens, one hydrogen and one etherified or esterified hydroxy, oxo or oxo protected in form of a ketal or thioketal and $R_9$ is amino, lower alkylamino, azido or acylamino, e.g. lower alkanoylamino or alkyloxycarbonylamino with a compound of the formula

(III'B)

wherein
$R_2'$ represents hydrogen or lower alkyl;
Z represents reactively esterified hydroxy and
$R_7'$ represents hydroxy, di(lower)alkylamino, lower alkoxy, aryl(lower)alkoxy, lower alkanoyloxymethoxy or lower alkoxycarbonyl(lower)alkoxy;

(b) optionally reducing, hydrogenolyzing, hydrolyzing or alkylating the resulting intermediate to obtain a compound of the formula II'

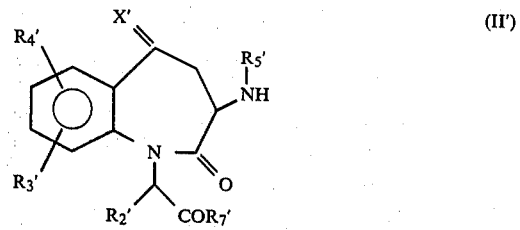

(II')

wherein $R_3'$, $R_4'$, X' are as defined for formula XI; $R_2'$ and $R_5'$ represent hydrogen or lower alkyl, $R_7'$ represents hydroxy, amino, mono- or di(lower)alkylamino, lower alkoxy, aryl(lower)alkoxy, lower alkanoyloxymethoxy, di(lower alkylamino)lower alkoxy or lower alkoxycarbonyl(lower)alkoxy;

(c) condensing a compound of formula II' above under conditions of reductive alkylation with a compound of the formula IV'

(IV')

wherein $R_1'$ is hydrogen, lower alkyl, acylated amino(-lower)alkyl, aryl, aryl(lower)alkyl, cycloalkyl(lower)alkyl and $R_6'$ represents hydroxy, di(lower)alkylamino, lower alkoxy, aryl(lower)alkoxy, lower alkanoyloxymethoxy or lower alkoxycarbonyl(lower)alkoxy; or condensing under alkylation conditions a compound of formula II' above with a compound of the formula III'A

(III'A)

wherein $R_1'$ and $R_6'$ have meanings given above in formula IV and Z represents reactively esterified hydroxy;

(d) optionally hydrolyzing or derivatizing the resulting product;

(e) converting any resulting compound of formula IA into another compound of the invention.

Compounds of formula XI are obtained from the corresponding optionally substituted and/or derivatized 2,3,4,5-tetrahydro-1H-[1]benzazepin-2-ones (J. Chem. Soc. 1937, 456; British Pat. No. 1,359,285; Liebig's Annalen Chemie 574, 171 (1951). Novel appropriately derivatized starting [1]benzazepin-2-ones are advantageously prepared by Beckmann rearrangement of the correspondingly derivatized naphthalene-1-ones using procedures known to the art and exemplified herein.

Said tetrahydro-[1]benzazepin-2-ones are converted to the 3-halo-, e.g. 3-chloro-2,3,4,5-tetrahydro-1H[1]benzazepin-2-one under conditions exemplified herein, e.g. by treatment with phosphorus pentachloride followed by hydrogenation. Substitution of said halo derivative with a metal azide, e.g. sodium azide and optional reduction, or substitution with ammonia or a lower alkylamine and optional acylation, yields compounds of formula XI.

Alternatively, compounds of formula XI wherein $R_9$ represents amino, alkylamino or acylamino are obtained by reduction and cyclization of the appropriately substituted and/or derivatized 4-(o-nitrophenyl)-2-aminobutyric acid and optional subsequent N-alkylation or N-acylation.

An alternate synthesis for the optically active compounds of this invention starts with the natural amino acid tryptophane. Specifically L-4-(o-aminophenyl)-4-oxo-2-aminobutyric acid (L-kynurenine, J. Am. Chem. Soc. 76, 1708 (1954), derived from L-tryptophane) is converted to an optically active starting material of formula XI wherein $R_9$ is acylamino, e.g. 3-(S)-t-butyloxycarbonylamino-2,3,4,5-tetrahydro-1H-[1]-benzazepine-2,5-dione as described in the Australian Journal of Chemistry 33, 633–40 (1980). The lactam alkylation of a compound of formula XI with a reactant of formula III′B, well known in the art, is preferably carried out in the presence of bases such as alkali metal hydrides, e.g. sodium or potassium hydride, alkali metal alkoxides, e.g. potassium t-butoxide or sodium methoxide, organo-metallic reagents, e.g. lithium diisopropylamide or under conditions of phase transfer catalysis e.g. in the presence of a tetrabutylammonium salt, preferably in a solvent e.g. tetrahydrofuran, dimethylformamide, at a temperature preferably between about 0° and 75° C.

Condensation of intermediates of formula II′ with the known α-ketoacid derivatives of formula IV′ (e.g. Chem. Ber. 31, 551, 3133) by reductive N-alkylation is carried out under conditions known to the art, e.g. by catalytic hydrogenation with hydrogen in the presence of platinum, palladium or nickel catalysts or with chemical reducing agents such as simple or complex light metal hydrides, advantageously an alkali metal cyanoborohydride such as sodium cyanoborohydride. The reductive amination with an alkali metal cyanoborohydride is preferably carried out in an inert solvent, e.g. methanol or acetonitrile, advantageously in the presence of an acid, e.g. hydrochloric acid or acetic acid at a temperature between about 0° and 50°, preferably room temperature.

Alkylation of intermediate amines of formula II′ with a reactant of formula III′A, well known to the art, is carried out with or without basic catalysts such as triethylamine or potassium carbonate in an inert solvent.

The compounds of formula I in general, and IA in particular, can also be prepared by sequences 2 and 3.

Sequence 2 comprises the following steps:

(a) Condensing under conditions of reductive alkylation a compound of the formula

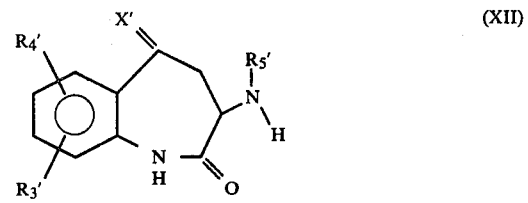

(XII)

wherein $R_3'$, $R_4'$ and $X'$ have meanings as defined for formula XI; and $R_5'$ is hydrogen or lower alkyl with a compound of the formula IV′

(IV′)

wherein $R_1'$ and $R_6'$ have meanings as previously defined, or under alkylation conditions with a compound of formula III′A

(III′A)

wherein $R_1'$, $R_6'$ and Z have meanings as previously defined to obtain a compound of the formula V′

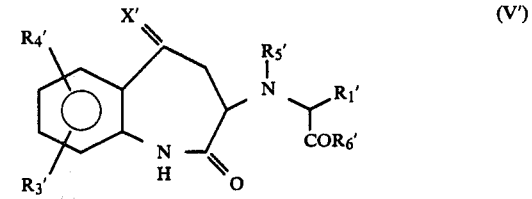

(V′)

wherein $R_1'$, $R_3'$, $R_4'$, $R_5'$, $R_6'$ and $X'$ have meanings as previously defined.

(b) Condensing under conditions of basic catalysis a resulting compound of the formula V′ with a compound of the formula III′B

(III′B)

wherein $R_2'$ and $R_7'$ and Z have meanings as previously defined;

(c) optionally hydrolyzing or derivatizing the resulting product;

(d) optionally converting any resulting compound of formula I into another compound of the invention.

Sequence 3 comprises the following steps:

(a) condensing a compound of the formula VII′

(VII′)

wherein

R$_1''$ is hydrogen, lower alkyl, acylated amino(lower-)alkyl, aryl, aryl(lower)alkyl, cycloalkyl(lower)alkyl; R$_5''$ represents hydrogen or lower alkyl; and R$_6''$ represents hydroxy, di(lower)alkylamino, lower alkoxy, aryl(lower)alkoxy, lower alkanoyloxymethoxy or lower alkoxycarbonyl(lower)alkoxy- with a compound of the formula VI′

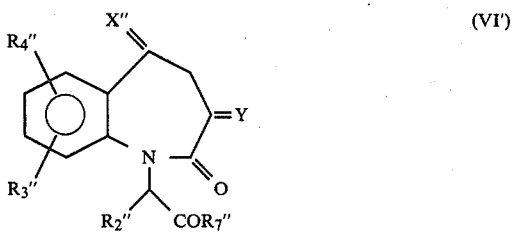

wherein

R$_2''$ represents hydrogen or lower alkyl;

R$_3''$ and R$_4''$ represent hydrogen, lower alkyl, lower alkoxy, lower alkanoyloxy, halogen, trifluoromethyl or R$_3''$ and R$_4''$ taken together represent lower alkylenedioxy; X″ represents 2 hydrogens, one hydrogen and one etherified or esterified hydroxy, oxo or oxo protected in the form of a ketal or thioketal; R$_7''$ represents hydroxy, di(lower)alkylamino, lower alkoxy, aryl(lower)alkoxy, lower alkanoyloxymethoxy or lower alkoxycarbonyl(lower)alkoxy; and Y represents oxo or dichloro- under conditions of reductive N-alkylation, or condensing a compound of formula VII′ with a compound of the above formula VI′ wherein X″ represents oxo, Y represents hydrogen and one reactively esterified or etherified hydroxy, or with a 3,4-dehydro elimination product of said compound or with a 3,4-dehydro derivative of said compound;

(b) optionally reducing hydrolyzing or derivatizing the resulting product;

(c) optionally converting any resulting compound into another compound of the invention.

In the preceding sequences 2 and 3 the steps of lactam alkylation, reductive N-alkylation and alkylation of amines are advantageously carried out under the conditions described for process 1.

In sequences 1, 2 and 3 described herein, reactants of e.g. formulae III′A, III′B and VII′ may be replaced with the corresponding nitriles, e.g. R$_2$′CH(Z)CN, R$_1$′CH(Z)CN and R$_5$NHCH(R$_1$′)CN respectively. The nitriles thus obtained may be converted to the carboxylic acids, esters and amides of formula I using methods well known to the art.

The starting materials of formula VII or VII′ represent amino acids and derivatives well known to the art or synthesized by methods well-known to the art. It is noteworthy that the optically active compounds of this invention may be synthesized starting with an optically active compound of formula VII or VII′, e.g. L-α-aminophenylbutyric acid, L-phenylalanine, L-tryptophane, L-methionine, L-aspartic acid, L-threonine, L-glutamic acid, L-lysine, L-ornithine or derivatives thereof.

In the case of reactants of e.g. formulae III′A, III′B, IV′ and VII′ wherein R$_7$′, R$_6$′ or R$_6''$ represent hydroxy, an appropriate carboxylate salt is prepared, preferably in situ, before condensation with the desired intermediates cited above.

Certain terms used in the foregoing processes have the meanings as defined below.

A reactively esterified hydroxy represents such esterified by a strong inorganic or organic acid, above all a hydrohalic acid, e.g. hydrochloric, hydrobromic or hydriodic acid, an aliphatic or aromatic sulfonic acid, e.g. methanesulfonic acid or p-toluenesulfonic acid.

Etherified hydroxy represents preferably lower alkoxy, e.g. methoxy, ethoxy or t-butoxy.

The optional steps of reducing, hydrogenolyzing hydrolyzing or derivatizing the initial products of the aforesaid processes and the conversion of a resulting product into another compound of this invention are performed by chemical methodology known to the art and exemplified herein.

Compounds of formula I or IA wherein R$_6$ and/or R$_7$ is lower alkoxy may be amidized with ammonia, mono- or di-(lower)alkylamines to yield compounds of formula I or IA wherein R$_6$ and/or R$_7$ represents unsubstituted, mono- or di-(lower)alkylamino.

Conversion of compounds of formula I or IA wherein R$_6$ and/or R$_7$ is lower alkoxy, aryl(lower)alkoxy, amino, mono- or di-(lower alkyl)amino to compounds of formula I or IA wherein R$_6$ and/or R$_7$ represents hydroxy is advantageously carried out by hydrolysis with inorganic acids such as hydrohalic or sulfuric acid or with aqueous alkalies preferably alkali metal hydroxides such as lithium or sodium hydroxide.

The selective conversion of compounds of formula I or IA wherein R$_6$ and/or R$_7$ represents α-aryl(lower)alkoxy, e.g. benzyloxy to compounds of formula I or IA wherein R$_6$ and/or R$_7$ represents hydroxy is advantageously carried out by hydrogenolysis using hydrogen in the presence of a catalyst, e.g. palladium.

Compounds of formula I or IA wherein neither R$_6$ nor R$_7$ represents hydroxy may be converted to monocarboxylic acids of formula I or IA wherein one of R$_6$ and R$_7$ is hydroxy. Such conversion is carried out by selective hydrolytic or hydrogenolytic procedures well known to the art and based on the chemical character of the R$_6$ and R$_7$ substituents.

Free carboxylic acids of formula I or IA wherein R$_6$ and/or R$_7$ represent hydroxy or salts thereof may be esterified with the appropriate alcohols or reactive derivatives thereof well known to the art to give the corresponding mono- or bis-ester, namely compounds of formula I or IA wherein R$_6$ and/or R$_7$ is lower alkoxy, aryl(lower)alkoxy, lower alkanoyloxymethoxy, or lower alkoxycarbonyl)lower alkoxy. Furthermore the free carboxylic acids may be converted via reactive intermediates to mono- or bis-amides of formula I wherein R$_6$ and/or R$_7$ represents amino, mono- or di-(lower)alkylamino.

Compounds of formula I or IA, and intermediates therefor, e.g. of formulae V and V′, wherein X and X′ represents oxo may be converted to the corresponding compounds wherein X or X′ represents one hydrogen and one hydroxy or reduction, e.g. by catalytic hydrogenation, e.g. with hydrogen in the presence of a platinum catalyst, or with a metal hydride reducing agent such as sodium borohydride. Resulting compounds wherein X or X′ represents one hydrogen and one hydroxy may be converted to compounds wherein X or X′ represents two hydrogens, e.g. by catalytic hydrogenation of the adduct of a carbodiimide, e.g. the adduct formed by condensation of a compound wherein X or X' represents one hydrogen and one hydroxy with dicyclohexylcarbodiimide in the presence of cuprous chloride according to the general method described in Chem. Ber., 107, 1353 (1974).

Alternatively, the compounds wherein X or X' represents one hydrogen and one hydroxy may be first converted to the corresponding compounds wherein X or X' represents one hydrogen and one acylated hydroxy (or acyloxy e.g. acetoxy) and subsequently reduced, e.g. by catalytic hydrogenation in the presence of a palladium catalyst, to compounds wherein X or X' represents two hydrogens.

Compounds of formula I or IA wherein $R_1$ represents amino(lower)alkyl may be converted to compounds wherein $R_1$ represents acylamino(lower)alkyl, or vice versa, by methods well-known in the art and described hereinabove in connection with protecting groups.

The above-mentioned reactions are carried out according to standard methods, in the presence or absence of diluents, preferably such as are inert to the reagents and are solvents thereof, of catalysts, condensing or said other agents respectively and/or inert atmospheres, at low temperatures, room temperature or elevated temperatures, preferably at the boiling point of the solvents used, at atmospheric or superatmospheric pressure.

The invention further includes any variant of the present processes, in which an intermediate product obtainable at any stage thereof is used as starting material and the remaining steps are carried out, or the process is discontinued at any stage thereof, or in which the starting materials are formed under the reaction conditions, or in which the reaction components are used in the form of their salts or optically pure antipodes. Mainly those starting materials should be used in said reactions, that lead to the formation of those compounds indicated above as being especially useful.

The invention also relates to novel starting materials and processes for their manufacture.

Depending on the choice of starting materials and methods, the new compounds may be in the form of one of the possible isomers or mixtures thereof, for example, depending on the number of asymmetric carbon atoms, as pure optical isomers, such as antipodes, or as mixtures of optical isomers such as racemates or mixtures of diastereoisomers.

Resulting mixtures of diastereoisomers and mixtures of racemates can be separated on the basis of the physicochemical differences of the constituents, in known manner, into the pure isomers, diastereoisomers or racemates, for example by chromatography and/or fractional crystallisation.

Resulting racemates can furthermore be resolved into the optical antipodes by known methods, for example by recrystallisation from an optically active solvent, by means of microorganisms or by reacting an acidic end product with an optically active base that forms salts with the racemic acid, and separating the salts obtained in this manner, for example on the basis of their different solubilities, into the diastereoisomers, from which the antipodes can be liberated by the action of suitable agents. Basic racemic products can likewise be resolved into the antipodes, for example, by separation of diastereomeric salts thereof, e.g. by the fractional crystallization of d- or l-tartrates. Any racemic intermediates or starting materials can likewise be resolved.

Advantageously, the more active of the two antipodes is isolated.

Finally, the compounds of the invention are either obtained in the free form, or as a salt thereof. Any resulting base can be converted into a corresponding acid addition salt, preferably with the use of a pharmaceutically acceptable acid or anion exchange preparation, or resulting salts can be converted into the corresponding free bases, for example, with the use of a stronger base, such as a metal or ammonium hydroxide or a basic salt, e.g. an alkali metal hydroxide or carbonate, or a cation exchange preparation. A compound of formula I wherein $R_o$ represents carboxy or of formula IA wherein $COR_6$ and/or $COR_7$ represent carboxy can thus also be converted into the corresponding metal or ammonium salts. These or other salts, for example, the picrates, can also be used for purification of the bases obtained; the bases are converted into salts, the salts are separated and the bases are liberated from the salts. In view of the close relationship between the free compounds and the compounds in the form of their salts, whenever a compound is referred to in this context, a corresponding salt is also intended, provided such is possible or appropriate under the circumstances.

The compounds, including their salts, can also be obtained in the form of their hydrates, or include other solvents used for the crystallization.

The pharmaceutical compositions according to the invention are those suitable for enteral, such as oral or rectal, and parenteral administration to mammals, including man, for the treatment or prevention of diseases responsive to inhibition of angiotensin-converting enzyme, e.g. cardiovascular diseases such as hypertension and congestive heart failure comprising an effective amount of a pharmacologically active compound of formula I, or pharmaceutically acceptable salts thereof, alone or in combination with one or more pharmaceutically acceptable carriers.

The pharmacologically active compounds of the invention are useful in the manufacture of pharmaceutical compositions comprising an effective amount thereof in conjunction or admixture with excipients or carriers suitable for either enteral or parenteral application. Preferred are tablets and gelatin capsules comprising the active ingredient together with (a) diluents, e.g. lactose, dextrose, sucrose, mannitol, sorbitol, cellulose and/or glycine, (b) lubricants, e.g. silica, talcum, stearic acid, its magnesium or calcium salt and/or polyethylene-glycol, for tablets also (c) binders, e.g. magnesium aluminum silicate, starch paste, gelatin, tragacanth, methylcellulose, sodium carboxymethylcellulose and/or polyvinylpyrrolidone, if desired, (d) disintegrants, e.g. starches, agar, alginic acid or its sodium salt, or effervescent mixtures and/or (e) absorbents, colorants, flavors and sweeteners. Injectable compositions are preferably aqueous isotonic solutions or suspensions, and suppositories are advantageously prepared from fatty emulsions or suspensions. Said compositions may be sterilized and/or contain adjuvants, such as preserving, stabilizing, wetting or emulsifying agents, solution promoters, salts for regulating the osmotic pressure and/or buffers. In addition, they may also contain other therapeutically valuable substances. Said compositions are prepared according to conventional mixing, granulating or coating methods, respectively, and contain about 0.1 to 75%, preferably about 1 to 50%, of the active ingredient. A unit dosage for a mammal of about 50 to 70 kg may contain between about 10 to 200 mg of the active ingredient.

The following examples are intended to illustrate the invention and are not to be construed as being limitations thereon. Temperatures are given in degrees Centrigrade, and all parts wherever given are parts by weight. If not mentioned otherwise, all evaporations are performed under reduced pressure, preferably between about 15 and 100 mmHg.

In the case of compounds of formula I or IA wherein more than one asymmetric center exists the resulting diastereoisomeric compounds are denoted as A, B, etc., in the said examples. The respective diastereoisomeric compounds are characterized by physical properties, e.g. melting point, relative migration on chromatography, infrared, or nuclear magnetic resonance spectral properties.

In the case of compounds of formula I or IA wherein X is $H_2$ and an asymmetric center exists in the side chain at the carbon atom bearing the nitrogen atom, the symbols A and B have been assigned as follows to the respective isomers on the basis of their relative migration on chromatography. On the basis of migration on thin-layer chromatography and normal phase high pressure liquid chromatography employing silica gel as the stationary phase, the fast moving isomer is called isomer A and the slow moving isomer is called isomer B. On the basis of migration on reverse phase high pressure liquid chromatography the slow moving isomer is called isomer A and the fast moving isomer is called isomer B.

EXAMPLE 1

1-Carboxymethyl-3-(1-ethoxycarbonyl-3-phenyl-propylamino)-2,3,4,5-tetrahydro-1H-[1]benzazepin-2-one (Higher melting isomer)

A solution of 3-amino-1-carboxymethyl-2,3,4,5-tetrahydro-1H-[1]benzazepin-2-one (10.0 g) and ethyl benzylpyruvate (26.4 g) in acetic acid (75 ml) and methanol (75 ml) was stirred at room temperature under nitrogen for 1 hour. Sodium cyanoborohydride (3.4 g) in methanol (25 ml) was added dropwise over 4 hours. The reaction mixture was stirred at room temperature for 24 hours. Concentrated hydrochloric acid (4 ml) was added dropwise, and the mixture stirred at room temperature for 1 hour. The reaction mixture was evaporated to dryness. The residue was partitioned between 150 ml of water and 50 ml of ether and adjusted to pH 9 with 40% sodium hydroxide. The layers were separated and the ether layer was discarded. The aqueous layer was adjusted to pH 4.3 with concentrated hydrochloric acid and extracted with 3×75 ml of ethyl acetate. The organic portions were dried (magnesium sulfate) and concentrated to dryness. Hydrogen chloride gas was bubbled into a solution of the crude product in 310 ml of methylene chloride for 5 minutes. The solution was evaporated and the residue was stirred in 225 ml of ether. The product was collected by filtration to give a 70:30 diastereomeric mixture as determined by high pressure liquid chromatography. The product was recrystallized from ethanol/ethyl acetate (1:3) to give 1-carboxymethyl-3-(1-ethoxycarbonyl-3-phenyl-propylamino)-2,3,4,5-tetrahydro-1H-[1]benzazepin-2-one hydrochloride melting at 246°–8° (dec.) and corresponding to the racemic isomer B.

A solution of the above hydrochloride salt (0.9 g) and propylene oxide (10 ml) in ethanol (150 ml) was stirred under nitrogen for 18 hours. The solution was evaporated to dryness, and the residue was dissolved in 3 ml of ethanol. Ether (75 ml) was added, precipitating a small quantity of the starting hydrochloride. The filtrate was evaporated to dryness and stirred with ether/petroleum ether (1:9). The solid was filtered off to give 1-carboxymethyl-3-(1-ethoxycarbonyl-3-phenyl-propylamino)-2,3,4,5-tetrahydro-1H-[1]benzazepin-2-one melting at 139°–141°, and being the higher melting racemic isomer B of the compound of formula IB wherein $C_nH_{2n}$ is ethylene, $R_6$ is ethoxy, $R_7$ is hydroxy and $R_8$ is phenyl.

Resolution under standard conditions with an optically active amine and separation of the diastereoisomeric salts will yield a pure enantiomer, e.g. 1-carboxymethyl-3S-(1S-ethoxycarbonyl-3-phenyl-propylamino)-2,3,4,5-tetrahydro-1H-[1]benzazepin-2-one of example 12.

Using high pressure liquid chromatography on a reverse phase column (solvent system: methanol, water (3:1) containing 0.025% acetic acid) isomer B was faster moving than lower melting racemic isomer A of example 5.

The starting material, 3-amino-1-carboxymethyl-2,3,4,5-tetrahydro-1H-[1]benzazepin-2-one, was prepared as shown:

A mixture of 2,3,4,5-tetrahydro-1H-[1]benzazepin-2-one (48.3 g, see Briggs et al., J. Chem. Soc. 1937, 456), phosphorus pentachloride (188 g), and xylene (1300 ml) was heated with stirring under an atmosphere of nitrogen to 90° (oil bath temperature) during 30 min with pauses at 30° (to allow the phosphorus pentachloride to dissolve) and at 50°. There was a copious evolution of hydrogen chloride. The temperature was maintained at 90° for 30 minutes. The reaction mixture was filtered while hot to remove a small amount of suspended solid, and the filtrate was evaporated under reduced pressure until all the solvent was removed. The residue was added with stirring to saturated aqueous sodium carbonate (100 ml). The product was filtered after the solidification process was complete, then slurried in ethanol (150 ml), filtered, washed with ethanol (50 ml) and ether (50 ml) and dried to give 3,3-dichloro-2,3,4,5-tetrahydro-1H-[1]benzazepin-2-one, m.p. 185°–187°:

A solution of 3,3-dichloro-2,3,4,5-tetrahydro-1H-[1]benzazepin-2-one (20 g, 0.174 mol) and anhydrous sodium acetate (15.4 g, 0.188 mol) in glacial acetic acid (920 ml) was hydrogenated at atmospheric pressure using 5% Pd-C (1.72 g) as catalyst until the uptake of hydrogen ceased. The catalyst was filtered off and the acetic acid evaporated under reduced pressure. The residue was equilibrated between 10% $NaHCO_3$ (900 ml) and dichloromethane (300 ml). The aqueous layer (pH 8) was further extracted with dichloromethane (3×300 ml) and the combined organic solutions were dried over anhydrous sodium sulfate and evaporated to give 3-chloro-2,3,4,5-tetrahydro-1H-[1]benzazepin-2-one, m.p. 163°–167°.

A solution of 3-chloro-2,3,4,5-tetrahydro-1H-[1]benzazepin-2-one (15.9 g, 0.08 mol) and sodium azide (6.36 g, 0.10 mol) in dimethylsulfoxide (320 ml) was maintained at 80° C. under an atmosphere of nitrogen for 3 hours. At this time, the IR spectrum of an aliquot showed a strong peak at 2150 $cm^{-1}$ characteristic of the azide group. The reaction mixture was poured into 1000 ml of ice/water and the suspension was stirred for 30 min. The solid was filtered off, washed with water (250 ml) and dried to give 3-azido-2,3,4,5-tetrahydro-1H-[1]benzazepin-2-one, m.p. 142°–5°.

A solution of 3-azido-2,3,4,5-tetrahydro-1H-[1]benzazepin-2-one (8.7 g, 0.043 mol), in dry dimethylformamide (75 ml) was added during 30 min to a stirred suspension of sodium hydride [from a 60% mineral oil dispersion (1.9 g) washed with petroleum ether (3×150 ml)] in dry dimethylformamide (250 ml) maintained at 0° C. under a nitrogen atmosphere. Stirring was continued for an additional 1.5 hours, then benzyl bromoacetate (10.8 g; 0.047 mol) in dry dimethylformamide (75 ml) was added during 45 minutes, the temperature being maintained at 0°. The reaction mixture is then allowed to warm to room temperature while stirring for an additional 18 hours. The dimethylformamide was removed under reduced pressure and the residue partitioned between water (500 ml) and dichloromethane (500 ml). The aqueous phase was extracted with additional dichloromethane (3×500 ml). The combined extracts were dried over sodium sulfate and the solvent was removed under reduced pressure to give the crude ester-azide as an oil. This material was dissolved in toluene (500 ml) and silica gel (48 g) was added. Filtration and removal of the solvent under reduced pressure gave 3-azido-1-benzyloxycarbonylmethyl-2,3,4,5-tetrahydro-1H-[1]benzazepin-2-one, as an oil, used without further purification in the next synthetic step.

A suspension of Raney nickel active catalyst in water (15 ml) was washed with ethanol (5×100 ml) and added to a mechanically stirred solution of 3-azido-1-benzyloxycarbonylmethyl-2,3,4,5-tetrahydro-1H-[1]benzazepin-2-one (5.0 g) in ethanol (300 ml), and the suspension was stirred for 18 hours at room temperature under nitrogen. The catalyst was filtered off and the solvent removed under reduced pressure. The residue was dissolved in 2N hydrochloric acid (200 ml) and the solution extracted with ether (2×250 ml). The aqueous solution was made basic (pH 9) with concentrated aqueous ammonia, and the solution extracted with ether (3×200 ml). The combined ether solutions were dried over sodium sulfate and evaporated under reduced pressure to give 3-amino-1-benzyloxycarbonylmethyl-2,3,4,5-tetrahydro-1H-[1]benzazepin-2-one as an oil, used without further purification for the next synthetic step.

3-Amino-1-benzyloxycarbonylmethyl-2,3,4,5-tetrahydro-1H-[1]benzazepine-2-one was also prepared as follows: a solution of 3-amino-2,3,4,5-tetrahydro-1H-[1]benzazepin-2-one (5.0 g, 0.028 mol), in dimethylformamide (100 ml) was added under a nitrogen atmosphere to a stirred suspension of sodium hydride [prepared from the 60% mineral oil dispersion (1.2 g) by washing with petroleum ether (3×150 ml)] in dimethylformamide (400 ml) to which tetrabutylammonium bromide (10.0 g, 0.031 mol) had been added. The reaction mixture was maintained at 50° for 15 minutes, then a solution of benzyl bromoacetate (7.2 g, 0.031 mol) in dimethylformamide (25 ml) was added. The reaction mixture was stirred for an additional 18 hours at 50°, then cooled to room temperature, and the dimethylformamide removed under high vacuum. The residue was stirred with toluene/dichloromethane (1:1, 500 ml) to precipitate inorganic salts. After filtration, the solution was evaporated under reduced pressure, and the residue chromatographed on silica gel (200 g). Elution with 0–15% ethyl acetate in toluene gave 3-amino-1-benzyloxycarbonylmethyl-2,3,4,5-tetrahydro-1H-[1]benzazepin-2-one as a major product.

A solution of 3-amino-1-benzyloxycarbonylmethyl-2,3,4,5-tetrahydro-1H-[1]-benzazepin-2-one (1.3 g) in ethanol (250 ml) was hydrogenated at room temperature and atmospheric pressure, using 10% Pd-C (0.20 g) as catalyst, until uptake of hydrogen ceased. The catalyst was filtered off and the solvent removed under reduced pressure to give a white foam (0.90 g). This material was triturated with ether to give 3-amino-1-carboxymethyl-2,3,4,5-tetrahydro-1H-[1]benzazepin-2-one, m.p. 147°–150°.

A solution of 3-azido-1-benzyloxycarbonylmethyl-2,3,4,5-tetrahydro-1H-[1]benzazepin-2-one (14.0 g, 0.04 mol) in ethanol (300 ml) was hydrogenated for 25 hours on a Parr shaker at 45 psi at room temperature using 5% Pd-C (2.0 g) as catalyst. The catalyst was filtered off and the solvent removed under reduced pressure. The residue was dissolved in water (500 ml) and the solution extracted with dichloromethane (2×400 ml). The aqueous solution was filtered, and evaporated under reduced pressure. Ethanol (50 mol) was added and the solution evaporated under reduced pressure. More ethanol (50 ml) was added, and the evaporation repeated. The residue was recrystallized from ethanol/ethyl acetate to give 3-amino-1-carboxymethyl-2,3,4,5-tetrahydro-1H-[1]benzazepin-2-one, m.p. 147°–50°.

EXAMPLE 2

1-Benzyloxycarbonylmethyl-3-(1-carboxy-3-phenylpropylamino)-2,3,4,5-tetrahydro-1H-[1]benzazepin-2-one Sodium cyanoborohydride (0.152 g, 0.0014 mol) was added to a solution of 1-benzyloxycarbonylmethyl-3-amino-2,3,4,5-tetrahydro-1H-[1]benzazepin-2-one (0.45 g, 0.0014 mol) and benzylpyruvic acid (0.48 g, 0.0028 ml) in methanol (35 ml). The reaction mixture was stirred at room temperature under nitrogen for 2 hours. Additional benzylpyruvic acid (0.48 g, 0.0028 mol) was added, and the reaction mixture stirred for an additional 18 hours. Concentrated hydrochloric acid (0.5 ml) was added and the resulting solution stirred for 1 hour. The solvents were removed under reduced pressure and the residue treated with dichloromethane (100 ml) to precipitate sodium chloride. After filtration, the solvent was removed under reduced pressure and the residue chromatographed on silica gel (30 g). Elution with ethyl acetate/methanol/acetic acid (90:10:0.2) gave 1-benzyloxycarbonylmethyl-3-(1-carboxy-3-phenylpropylamino)-2,3,4,5-tetrahydro-1H-[1]benzazepin-2-one as an oil; NMR(CDCl$_3$) 7.35(m,14H), 5.10(s, 2H), 4.60(m,2H), 3.00(m, 12H).

EXAMPLE 3

1-Benzyloxycarbonylmethyl-3-(1-ethoxycarbonyl-3-phenylpropylamino)-2,3,4,5-tetrahydro-1H-[1]benzazepin-2-one A solution of 1-benzyloxycarbonylmethyl-3-(1-carboxy-3-phenylpropylamino)-2,3,4,5-tetrahydro-1H-[1]benzazepin-2-one (0.364 g, 0.00075 mol), sodium bicarbonate (0.190 g, 0.0022 mol), and ethyl iodide (0.315 g, 0.002 mol) in dimethylacetamide (15 ml) was stirred at room temperature under nitrogen for 72 hours. The reaction mixture was filtered and evaporated under reduced pressure. Water (100 ml) was added, and the resulting solution extracted with dichloromethane (4×50 ml). The combined extracts were dried over sodium sulfate and the solvent removed under reduced pressure to give the diester (0.324 g, 84% yield) as an oil. This material was separated by high pressure liquid chromatography into three fractions, using ethyl acetate/toluene (30:70) as solvent. The first fraction yielded isomer A of the title compound as an oil; the second fraction contained a mixture of isomers A and B and the third fraction yielded isomer B of the title compound. Using high pressure liquid chromatography on a reverse phase column (solvent system: methanol, water (3:1) containing 0.025% acetic acid) isomer A moved more slowly than isomer B.

EXAMPLE 4

1-Carboxymethyl-3-(1-ethoxycarbonyl-3-phenyl-propylamino)-2,3,4,5-tetrahydro-1H-[1]benzazepin-2-one (Higher melting isomer)

A solution of 1-benzyloxycarbonylmethyl-3-(1-ethoxycarbonyl-3-phenylpropylamino)-2,3,4,5-tetrahydro-1H-[1]benzazepin-2-one (isomer B of example 3, 0.9 g) in ethanol (150 ml) was hydrogenated at room temperature and atmospheric pressure, using 10% palladium on charcoal (0.5 g) as catalyst. After uptake of hydrogen had ceased, the catalyst was filtered off, and the solvent removed under reduced pressure to give a solid. This material was triturated with ether (8 ml) to give the title compound melting at 138°-140° and identical to the compound obtained in Example 1.

EXAMPLE 5

1-Carboxymethyl-3-(1-ethoxycarbonyl-3-phenyl-propylamino)-2,3,4,5-tetrahydro-1H-[1]benzazepin-2-one (Lower melting isomer)

A solution of 1-benzyloxycarbonylmethyl-3-(1-ethoxycarbonyl-3-phenylpropylamino)-2,3,4,5-tetrahydro-1H-[1]benzazepin-2-one (isomer A of example 3; 1.2 g) in ethanol (125 ml) was hydrogenated at room temperature and atmospheric pressure, using 10% palladium on charcoal (0.5 g) as catalyst. After uptake of hydrogen had ceased, the catalyst was filtered off, and the solvent removed under reduced pressure to give a solid. This material was triturated with ether (8 ml) to give 1-carboxymethyl-3-(1-ethoxycarbonyl-3-phenyl-propylamino)-2,3,4,5-tetrahydro-1H-[1]benzazepin-2-one melting at 126°-129°, and being the lower melting racemic isomer A.

Using high pressure liquid chromatography on a reverse phase column (solvent system: methanol, water (3:1) containing 0.025% acetic acid) isomer A moved more slowly than higher melting racemic isomer B of example 1.

EXAMPLE 6

1-Benzyloxycarbonylmethyl-3-(1-ethoxycarbonyl-3-phenylpropylamino)-2,3,4,5-tetrahydro-1H-[1]benzazepin-2-one A solution of 3-(1-ethoxycarbonyl-3-phenyl-propylamino)-2,3,4,5-tetrahydro-1H-[1]benzazepin-2-one (5.0 g), in dry dimethylformamide (20 ml) was added under a nitrogen atmosphere to a stirred suspension of sodium hydride [prepared from the 60% mineral oil dispersion (0.6 g) by washing with petroleum ether (3×75 ml)] in dry dimethylformamide (85 ml) to which tetrabutylammonium bromide (4.4 g) had been added. The reaction mixture was stirred at room temperature for 30 minutes, then a solution of benzyl bromoacetate (3.2 g) in dry dimethylformamide (10 ml) was added. The reaction mixture was stirred for an additional 30 minutes at room temperature, heated to 60°, and maintained at that temperature for 18 hours. The reaction mixture was cooled to room temperature, and the solvent removed under high vacuum. Water (150 ml) was added, and the resulting solution extracted with ethyl acetate (2×250 ml). The combined ethyl acetate extracts were washed with water (100 ml), dried over magnesium sulfate, and the solvent removed under reduced pressure to give a brown oil. This material was chromatographed on silica gel (150 g). Elution with toluene/ethyl acetate (3:1) first gave isomer A of 1-benzyloxycarbonylmethyl-3-(1-ethoxycarbonyl-3-phenyl-propylamino)-2,3,4,5-tetrahydro-1H-[1]benzazepin-2-one followed by isomer B. Isomer A and B were identical to compounds of example 3 as determined by high pressure liquid chromatography on a reverse phase column (solvent system: methanol, water (3:1) containing 0.025% acetic acid).

The starting material was prepared as follows:

A solution of diethyl acetamidomalonate (33.2 g) in ethanol (150 ml) was added to a solution of sodium ethoxide in ethanol [prepared from sodium (3.8 g) and ethanol (200 ml)]. The reaction mixture was stirred at room temperature for 30 minutes and a solution of 2-nitrophenethyl bromide (J. Med. Chem. 20, 1020 (1977), 40.0 g) in ethanol (100 ml) was added dropwise during 20 minutes. After addition was complete, the reaction mixture was refluxed for 18 hours, then cooled to room temperature and evaporated under reduced pressure. The residue was dissolved in water (350 ml) and the solution extracted with ethyl acetate (2×350 ml). The combined ethyl acetate extracts were washed with water (200 ml) and dried over magnesium sulfate. Removal of the solvent under reduced pressure gave diethyl 2-acetamido-2-(o-nitrophenethyl)malonate as a low melting solid, used without further purification for the next synthetic step.

A solution of diethyl 2-acetamido-2-(o-nitrophene-thyl)malonate (80 g) in 3N hydrochloric acid (900 ml) was refluxed for 12 hours. The solution was cooled and extracted with ethyl acetate (200 ml). The aqueous solution was filtered, and evaporated to dryness under reduced pressure. The residue was recrystallized from ethanol/ether to give 2-amino-4-(2-nitrophenyl)butyric acid hydrochloride, m.p. 219°-221° (dec).

A solution of 2-amino-4-(2-nitrophenyl)butyric acid hydrochloride (38.0 g) in 10% ethanolic hydrogen chloride (1200 ml) was refluxed with stirring for 18 hours. The reaction mixture was evaporated to dryness under reduced pressure, water (250 ml) was added, and the aqueous solution made basic by the addition of 2N sodium hydroxide. The solution was extracted with dichloromethane (2×500 ml), and the combined dichloromethane solutions washed with water (2×150 ml), and dried over anhydrous magnesium sulfate. Evaporation gave ethyl 2-amino-4-(2-nitrophenyl)butyrate, used without further purification for the next synthetic step.

A solution of ethyl 2-amino-4-(2-nitrophenyl)buty-rate (27 g) in ethanol (600 ml) was hydrogenated at room temperature and atmospheric pressure, using 10% palladium on charcoal (2.5 g) as catalyst, until hydrogen uptake ceased. The catalyst was filtered off and evaporation to dryness gave ethyl 2-amino-4-(2-amino-phenyl)butyrate used without purification for the next synthetic step.

A solution of ethyl 2-amino-4-(2-aminophenyl)buty-rate (35.0 g) in methanol (100 ml) was added to a solution of sodium methoxide in methanol [prepared from sodium (1.0 g) and methanol (400 ml)] with stirring, under a nitrogen atmosphere. The reaction mixture was refluxed for 65 hours and evaporated under reduced pressure. The residue was distributed between water (100 ml) and dichloromethane (400 ml). The aqueous solution was extracted with dichloromethane (400 ml), and the combined organic solutions washed with water (100 ml) and dried over magnesium sulfate. Evaporation to dryness and trituration with ether (250 ml) gave 3-amino-2,3,4,5-tetrahydro-1H-[1]benzazepin-2-one, m.p. 161°–162° C.

Alternatively, a solution of 2-amino-4-(2-nitrophenyl)butyric acid hydrochloride (2.5 g) in water (200 ml) was hydrogenated at room temperature and atmospheric pressure, using 10% Pd-C (0.5 g) as catalyst. After uptake of hydrogen ceased, the catalyst was filtered off, and the filtrate evaporated to dryness. The residue was dissolved in water (50 ml) and the pH adjusted to 7 by the addition of 10% sodium hydroxide. The solid was filtered off, washed with water, and dried to give 2-amino-4-(2-aminophenyl)butyric acid. A solution of the 2-amino-4-(2-aminophenyl)butyric acid (1.0 g), hexamethyldisilazane (5.4 g), and chlorotrimethylsilane (0.1 g) in xylene (125 ml) was refluxed for 65 hours. The reaction mixture was cooled, poured into ethanol (200 ml) and evaporated under reduced pressure. Water (100 ml) was added, and the solution extracted with dichloromethane (2×125 ml). The combined dichloromethane solutions were washed with water (50 ml), dried over magnesium sulfate, and evaporated under reduced pressure to give 3-amino-2,3,4,5-tetrahydro-1H-[1]benzazepin-2-one as above.

3-Amino-2,3,4,5-tetrahydro-1H-[1]benzazepin-2-one is also prepared as follows:

To a solution of 3-azido-2,3,4,5-tetrahydro-1H-[1]benzazepin-2-one (see Example 1) (27 g) in 2B ethanol (3500 ml) stirring at room temperature under an atmosphere of nitrogen, a suspension of Raney nickel in water (50 ml, washed with 10 volumes of ethanol) was added. The mixture was stirred at room temperature for 2 hours when an additional 30 ml of Raney nickel suspension was added. After stirring for an additional 30 minutes, the catalyst was filtered off and the solvent removed under reduced pressure to give an oil which solidified on addition of ether to give 3-amino-2,3,4,5-tetrahydro-1H-[1]benzazepin-2-one, melting at 161°–2°.

A solution of 3-amino-2,3,4,5-tetrahydro-1H-[1]benzazepin-2-one (8.0 g) and benzylpyruvic acid (18.0 g) in methanol (450 ml) was stirred at room temperature under nitrogen for 30 minutes. Sodium cyanoborohydride (4.5 g) was added, and the resulting solution stirred at room temperature for 48 hours. Concentrated hydrochloric acid (7 ml) was added dropwise during 10 minutes and stirring was maintained for an additional 1 hour. The reaction mixture was evaporated to dryness, dichloromethane (150 ml) was added, and the mixture stirred for 30 minutes. The solid was filtered off, stirred with water (100 ml) for 15 minutes, then filtered, washed with water (50 ml), and dried to give 3-(1-carboxy-3-phenylpropylamino)-2,3,4,5-tetrahydro-1H-[1]benzazepin-2-one, m.p. 173°–175° as a mixture of isomers.

A solution of 3-(1-carboxy-3-phenylpropylamino)-2,3,4,5-tetrahydro-1H-[1]benzazepin-2-one (6.0 g), sodium bicarbonate (4.0 g), and ethyl iodide (11.6 g) in dimethylacetamide (200 ml) was stirred at room temperature under nitrogen for 72 hours. The reaction mixture was filtered and evaporated under high vacuum. Water (250 ml) was added, and the resulting solution extracted with dichloromethane (2×400 ml). The combined extracts were dried over magnesium sulfate and the solvent removed under reduced pressure to give 3-(1-ethoxycarbonyl-3-phenylpropylamino)-2,3,4,5-tetrahydro-1H-[1]benzazepin-2-one as a mixture of isomers. NMR(CDCl$_3$)δ9.22(s, 1H), 4.10(2 superimposed quartets, 2H), 1.13(2 superimposed triplets, 3H).

EXAMPLE 7

1-Benzyloxycarbonylmethyl-3-(1-benzyloxycarbonyl-3-phenylpropylamino)-2,3,4,5-tetrahydro-1H-[1]benzazepin-2-one A solution of 3-(1-benzyloxycarbonyl-3-phenylpropylamino)-2,3,4,5-tetrahydro-1H-[1]-benzazepin-2-one (4.0 g) in dry dimethylformamide was added under a nitrogen atmosphere to a stirred suspension of sodium hydride [from the 60% mineral oil dispersion (0.42 g) washed with petroleum ether (3×80 ml)] in dry dimethylformamide (100 ml) at room temperature to which tetrabutylammonium bromide (3.1 g) had been added. Stirring was continued for an additional 30 minutes at room temperature, when a solution of benzyl bromoacetate (2.2 g) in dry dimethylformamide (10 ml) was added. After an additional 30 minutes at room temperature, the reaction mixture was heated to 50°, and maintained at that temperature for 18 hours. The reaction mixture was cooled to room temperature, and the solvent removed under high vacuum. Water (150 ml) was added and the solution extracted with ethyl acetate (2×300 ml). The combined ethyl acetate solutions were washed with water (100 ml), dried over magnesium sulfate, and the solvent removed under reduced pressure to give a brown oil which was chromatographed on silica gel (250 g). Elution with toluene/ethyl acetate (1:1; 600 ml) gave an oil, characterized as isomer A of the title compound; NMR (CDCl$_3$) 5.12(s, 4H), 4.50 (q, 2H). Elution with an additional 2 liters of the solvent mixture gave an oil characterized as isomer B of the title compound; NMR(CDCl$_3$)δ5.17(s,2H), 5.03(d,2H), 4.60 (q, 2H).

The starting material was prepared as follows:

A solution of 3-(1-carboxy-3-phenylpropylamino)-2,3,4,5-tetrahydro-1H-[1]benzazepin-2-one (as described in example 6, 13.0 g), sodium bicarbonate (10.0 g), and benzyl bromide (19.0 g) in dimethylacetamide (750 ml) was stirred at room temperature under a nitrogen atmosphere for 72 hours. The reaction mixture was filtered and evaporated under high vacuum. Water (150 ml) was added, and the resulting solution extracted with dichloromethane (2×400 ml). The combined extracts were washed with water (100 ml), dried over magnesium sulfate and evaporated under reduced pressure to give the crude benzyl ester. Recrystallization from ethyl acetate gave 3-(1-benzyloxycarbonyl-3-phenylpropylamino)-2,3,4,5-tetrahydro-1H-[1]benzazepin-2-one, m.p. 139°–141°.

EXAMPLE 8

1-Carboxymethyl-3-(1-carboxy-3-phenylpropylamino)-2,3,4,5-tetrahydro-1H-[1]benzazepin-2-one (Lower melting isomer)

A solution of 1-benzyloxycarbonylmethyl-3-(1-benzyloxycarbonyl-3-phenylpropylamino)-2,3,4,5-tetrahydro-1H-[1]benzazepin-2-one (isomer A of example 7, 2.7 g) in ethanol (800 ml) was hydrogenated at room temperature and atmospheric pressure, using 10% palladium on charcoal (0.5 g) as catalyst. After uptake of hydrogen had terminated, the catalyst was filtered off, and the solvent removed under reduced pressure to give the title diacid, characterized as isomer A, m.p. 256°–259°.

The identical compound is obtained on hydrolysis of the compound of example 5.

EXAMPLE 9

1-Carboxymethyl-3-(1-carboxy-3-phenylpropylamino)-2,3,4,5-tetrahydro-1H-[1]benzazepin-2-one (Higher melting isomer)

A solution of 1-benzyloxycarbonylmethyl-3-(1-benzyloxycarbonyl-3-phenylpropylamino)-2,3,4,5-tetrahydro-1H-[1]benzazepin-2-one (isomer B of example 7, 5.0 g) in ethanol (950 ml) was hydrogenated at room temperature and atmospheric pressure, using palladium on charcoal (0.5 g) as catalyst. After uptake of hydrogen had terminated, the catalyst was filtered off, and the solvent removed under pressure to give the title diacid, characterized an isomer B, m.p. 280°–282°.

The identical compound is obtained on hydrolysis of the compound of example 1 (isomer B) or compound of example 10 (isomer B).

EXAMPLE 10

1-Ethoxycarbonylmethyl-3-(1-ethoxycarbonyl-3-phenylpropylamino)-2,3,4,5-tetrahydro-1H-[1]benzazepin-2-one A solution of 3-(1-ethoxycarbonyl-3-phenylpropylamino)-2,3,4,5-tetrahydro-1H-[1]-benzazepine-2-one (see example 6, 3.0 g) in dry dimethylformamide (10 ml) was added dropwise during 10 minutes to a stirred suspension of sodium hydride [from the 60% mineral oil dispersion (0.36 g) washed with petroleum ether (3×75 ml)] in dry dimethylformamide (100 ml) at room temperature under nitrogen. Stirring was maintained for an additional 30 minutes, a solution of ethyl bromoacetate (1.4 g) in dimethylformamide (15 ml) was added and the reaction mixture was maintained at 60° for 48 hours. After the reaction mixture was cooled to room temperature, the solvent was removed under high vacuum. Water (100 ml) was added, and the solution extracted with ethyl acetate (2×200 ml). The combined ethyl acetate solutions were washed with water (50 ml), dried over magnesium sulfate, and the solvent removed under reduced pressure to give a yellow oil (3.8 g). This material was chromatographed on silica gel (120 g). Elution with toluene/ethyl acetate (1:1; 250 ml) gave isomer A of the desired product. Elution with an additional 250 ml of solvent mixture gave an oil which contained mostly isomer B and some isomer A of the desired product as determined by analytical high pressure liquid chromatography (see Example 6). Elution with a further 250 ml of solvent mixture gave an oil which was essentially pure isomer B (slower moving). This material was dissolved in methanol (25 ml) and converted to the maleate salt by addition of an equimolar quantity of maleic acid in methanol. Evaporation of the solvent and recrystallization of the residue from methanol/ether yielded pure isomer B of 1-ethoxy-carbonylmethyl-3-(1-ethoxycarbonyl-3-phenylpropylamino)-2,3,4,5-tetrahydro-1H[1]benzazepin-2-one as the maleate salt melting at 114°–116°.

EXAMPLE 11

1-Carboxymethyl-3-carboxymethylamino-2,3,4,5-tetrahydro-1H-[1]benzazepin-2-one

A solution of 1-benzyloxycarbonylmethyl-3-benzyloxycarbonylmethylamino-2,3,4,5-tetrahydro-1H-[1]benzazepin-2-one (4.8 g; 0.01 mol) in ethanol (550 ml) was hydrogenated at room temperature and atmospheric pressure using 5% Pd-C (0.85 g) as catalyst until uptake of hydrogen ceased. Water (300 ml) was added, the catalyst filtered off, and the solvent removed under reduced pressure. The residue was triturated with ether to give the title diacid, m.p. 232°–236°.

The starting material was prepared as follows:

A solution of 3-amino-2,3,4,5-tetrahydro-1H-[1]benzazepin-2-one (5.0 g, 0.028 mol) in dimethylformamide (100 ml) was added under a nitrogen atmosphere to a stirred suspension of sodium hydride [prepared from the 60% mineral oil dispersion (1.2 g) by washing with petroleum ether (3×105)] in dimethylformamide (400 ml) to which tetrabutylammonium bromide (10.9 g, 0.031 mol) had been added. The reaction mixture was maintained at 50° for 15 minuites, then a solution of benzyl bromoacetate (7.2 g, 0.031 mol) in dimethylformamide (25 ml) was added. The reaction mixture was stirred for an additional 18 hours at 50°, then cooled to room temperature, and the dimethylformamide removed under high vacuum. The residue was stirred with toluene/dichloromethane (1:1, 500 ml) to precipitate inorganic salts. After filtration, the solution was evaporated under reduced pressure, and the residue chromatographed on silica gel (200 g). Elution with 0–15% ethyl acetate in toluene gave 1-benzyloxycarbonylmethyl-3-benzyloxycarbonylmethylamino-2,3,4,5-tetrahydro-1H-[1]benzazepin-2-one as the first fraction. Further elution gave 3-benzyloxycarbonylamino-2,3,4,5-tetrahydro-1H-[1]benzazepin-2-one, m.p. 124°–127° C. and 3-amino-1-benzyloxycarbonylmethyl-2,3,4,5-tetrahydro-1H-[1]benzazepin-2-one (see example 1).

EXAMPLE 12

1-Carboxymethyl-3S-(1S-ethoxycarbonyl-3-phenylpropylamino)2,3,4,5-tetrahydro-1H-[1]benzazepin-2-one 3(S)-Amino-1-carboxymethyl-2,3,4,5-tetrahydro-1H-[1]benzazepin-2-one when treated with ethyl benzylpyruvate in the presence of sodium cyanoborohydride by the procedure described in example 1 for the racemic compound gave after purification 1-carboxymethyl-3S-(1S-ethoxycarbonyl-3-phenylpropylamino)-2,3,4,5-tetrahydro-1H-[1]benzazepin-2-one, as described below.

A solution of sodium hydroxide (2.1 g) in water (5 ml) was added to a solution of 3-(S)-amino-1-ethoxycarbonylmethyl-2,3,4,5-tetrahydro-1H-[1]benzazepine-2-one (14.0 g) in methanol (150 ml) at room temperature, and the solution was stirred for two hours. The solvents were evaporated and the residue thoroughly dried, then slurried with ether, to give 3(S)-amino-1-carboxymethyl-2,3,4,5-tetrahydro-1H-[1]benzazepine-2-one sodium salt. This was used without further purification.

A solution of the above sodium salt (12.9 g) and ethyl benzylpyruvate (31 g) in acetic acid (100 ml) and methanol (75 ml) was stirred at room temperature under a dry nitrogen atmosphere for one hour. A solution of sodium cyanoborohydride (3.8 g) in methanol (30 ml) was then added dropwise over a 4 hour period. The combined solutions were stirred overnight at room temperature. Concentrated hydrochloric acid (10 ml) was added dropwise and the mixture stirred at room temperature for 1 hour followed by the evaporation of solvents. The residue was partitioned between water (400 ml) and ether (100 ml) and the pH adjusted to 9.3 with 40% sodium hydroxide. The layers were separated and the ether layer discarded. The aqueous layer was adjusted to pH 4.3 with concentrated hydrochloric acid and extracted with ethyl acetate (3×100 ml). The organic phases were combined, dried (magnesium sulfate), and evaporated. Hydrogen chloride gas was bubbled through a solution of the crude product in methylene chloride (150 ml) for 5 minutes. The solvent was evaporated and the resulting foam was dissolved in hot methyl ethyl ketone (100 ml). The solid which precipitated was collected by filtration to give a 95:5 diastereomeric mixture as determined by high pressure liquid chromatography. The product was recrystallized from 3-pentanone/methanol (10:1) to give 1-carboxymethyl-3S-(1S-ethoxycarbonyl-3-phenylpropylamino)-2,3,4,5-tetrahydro-1H-[1]benzazepin-2-one hydrochloride, m.p. 188°-190°, $[\alpha]_D = 141.0°$ (c=0.9 in ethanol), of formula Ic wherein $C_nH_{2n}$ is ethylene, $R_6$ is ethoxy, $R_7$ is hydroxy and $R_8$ is phenyl.

A solution of the above hydrochloride salt (0.035 g) and propylene oxide (0.5 ml) in ethanol (4 ml) was stirred under nitrogen overnight at room temperature. The solution was evaporated to dryness. Ether (2 ml) was added, and the solid was filtered off to give 1-carboxymethyl-3-S-(1S-ethoxycarbonyl-3-phenyl-propylamino)-2,3,4,5-tetrahydro-1H-[1]benzazepin-2-one, m.p. 148°-9°, $[\alpha]_D = -159°$ (c=1.2 in ethanol).

The optically active starting material was prepared as indicated below.

(a) A solution of 0.4 g of 3-(S)-t-butyloxycarbonylamino-2,3,4,5-tetrahydro-1H-[1]benzazepin-2,5-dione, prepared from L-kynurenine as described in Australian J. Chemistry Vol. 33, 633-40 (1980), and ethyl bromoacetate (0.23 g) in dry tetrahydrofuran (30 ml) was stirred at 0° under a dry nitrogen atmosphere. Potassium t-butoxide (0.254 g) was added in one portion. After 1 hour at 0°, an additional quantity of ethyl bromoacetate (0.23 g) was added and the reaction mixture was stirred at 0° for a further 1 hour. Water (100 ml) was added and the mixture was extracted with ethyl acetate (2×50 ml). The combined ethyl acetate solutions were washed with water (100 ml) and dried over magnesium sulfate. Removal of the solvent under reduced pressure gave a yellow gum which on trituration with ether/petroleum ether (bp 30°-60°) gave 3-(S)-t-butyloxycarbonylamino-1-ethoxycarbonylmethyl-2,3,4,5-tetrahydro-1H-[1]benzazepin-2,5-dione, mp 86°-88°, $[\alpha]_D = -203°$ (c=1 in DMF).

A solution of 3-(S)-t-butyloxycarbonylamino-1-ethoxycarbonylmethyl-2,3,4,5-tetrahydro-1H-[1]benzazepin-2,5-dione (0.14 g) and sodium borohydride (7 mg) in ethanol (10 ml) was stirred at room temperature for 18 hours. The ethanol was removed under reduced pressure, and the residue dissolved in dichloromethane (25 ml). The solution was extracted with 2N HCl (2×20 ml) and saturated brine (20 ml), and dried over sodium sulfate. The solvent was removed under reduced pressure, and the residue triturated with ether to give 3-(S)-t-butyloxycarbonylamino-1-ethoxycarbonylmethyl-5-hydroxy-2,3,4,5-tetrahydro-1H-[1]benzazepin-2-one, mp 167°-169.5° C., $[\alpha]_D = -193°$ (c=0.52 in DMF). The substance was also obtained by hydrogenation of the benzazepin-2,5-dione derivative with $H_2$/Pt in ethanol.

A mixture of 3-(S)-t-butyloxycarbonylamino-1-ethoxycarbonylmethyl-5-hydroxy-2,3,4,5-tetrahydro-1H-[1]benzazepin-2-one (0.076 g), dicyclohexylcarbodiimide (0.064 g) and cuprous chloride (7 mg) was heated at 60° C. under nitrogen for 32 hours. The reaction was allowed to cool to room temperature. The residue was dissolved in methylene chloride (50 ml) and washed with dilute $NH_4OH$ (2×15 ml) followed by $H_2O$ (20 ml). The organic phase was dried over sodium sulfate and evaporated to give a mixture of the desired adduct and excess dicyclohexylcarbodiimide.

The mixture (0.100 g) was dissolved in ethyl acetate (40 ml) and placed in a pressure bottle. 10% Pd/C (0.010 g) was added and the mixture was hydrogenated at 3 atmospheres pressure and at 40° for 16 hours. The catalyst was filtered off and the filtrate evaporated. The residue was triturated with ether, and the ether solution evaporated to give 3-(S)-t-butyloxycarbonylamino-1-ethoxycarbonylmethyl-2,3,4,5-tetrahydro-1H-[1]benzazepin-2-one, mp 115°-116.5° C., $[\alpha]_D = -182°$ (c=2.6 in DMF).

(b) Tartaric acid (12.6 g) and racemic 3-amino-1-ethoxycarbonylmethyl-2,3,4,5-tetrahydro-1H-[1]benzazepin-2-one (22 g) were dissolved in hot ethanol (200 ml). This solution was cooled and allowed to stand overnight at room temperature. The solid which precepitated was collected by filtration and recrystallized twice from ethanol (200 ml) to give 3-(S)-amino-1-ethoxycarbonylmethyl-2,3,4,5-tetrahydro-1H-[1]benzazepin-2-one tartrate salt. This was dissolved in $H_2O$ (100 ml) and the pH adjusted to 9 with dilute ammonium hydroxide and extracted with methylene chloride (2×50 ml). The combined extracts were washed with water (75 ml), dried (magnesium sulfate) and evaporated to give 3-(S)-amino-1-ethoxycarbonylmethyl-2,3,4,5-tetrahydro-1H -[1]benzazepin-2-one, m.p. 104°-106°, $[\alpha]_D = -285.5°$ (c=0.99 in ethanol).

(c) Hydrogen chloride gas was bubbled through a solution of 3-(S)-t-butyloxycarbonylamino-1-ethoxycarbonylmethyl-2,3,4,5-tetrahydro-1H-[1]benzazepin-2-one (under a) above, 0.225 g) in ethyl acetate (25 ml) for 45 minutes. Nitrogen was then bubbled through this solution for 30 minutes. The ethyl acetate was washed with water (30 ml) and 1N HCl (30 ml). The ethyl acetate layer was discarded and the aqueous phases combined. The aqueous solution was adjusted to pH 9 with dilute ammonium hydroxide, extracted with ethyl acetate, (3×50 ml); the organic phases were combined, dried (sodium sulfate) and evaporated to give 3-(S)-amino-1-ethoxy-carbonylmethyl-2,3,4,5-tetrahydro-1H-[1]benzazepin-2-one, m.p. 101°-102° C., $[\alpha]_D = -298°$ (c=0.46 in ethanol).

Treatment with ethanedithiol/boron trifluoride etherate or trifluoroacetic acid/anisole to remove the protecting group also yields 3-(S)-amino-1-ethoxycarbonylmethyl-2,3,4,5-tetrahydro-1H-[1]benzazepin-2-one.

Alternately 3-(S)-amino-1-ethoxycarbonylmethyl-2,3,4,5-tetrahydro-1H-[1]-benzazepin-2-one was also prepared as follows:

(d) A solution of 3-(S)-t-butyloxycarbonylamino-1-ethoxycarbonylmethyl-5-hydroxy-2,3,4,5-tetrahydro-1H-[1]benzazepine-2-one (previously described, 1.0 g) in acetic anhydride (20 ml) was maintained at 80° for 3 hours. The reaction mixture was cooled to room temperature and the solvents removed under reduced pressure. Ether (100 ml) was added, and the resulting solution washed with water (50 ml) and dried over magnesium sulfate. The solvent was removed under reduced pressure to give 5-acetoxy-3-(S)-t-butyloxycarbonylamino-1-ethoxycarbonylmethyl-2,3,4,5-tetrahydro-1H-[1]benzazepin-2-one as a pale yellow oil which was used without further purification.

A solution of 5-acetoxy-3-(S)-t-butyloxycarbonylamino-1-ethoxycarbonylmethyl-2,3,4,5-tetrahydro-1H-[1]benzazepin-2-one (0.7 g) in ethanol (50 ml) was hydrogenated at 42 psi for 24 hours at 70° using 10% palladium on charcoal (0.5 g) as catalyst. The catalyst was filtered off and the solvent removed under reduced pressure to give 3-(S)-t-butyloxycarbonylamino-1-ethoxycarbonylmethyl-2,3,4,5 tetrahydro-1H-[1]benzazepin-2-one which, without further purification was converted to 3-(S)-amino-1-ethoxycarbonylmethyl-2,3,4,5-tetrahydro-1H-[1]benzazepin-2-one by the procedure described above; m.p. 99°–101°, $[\alpha]_D = -297°$ (c=1 in ethanol).

(e) A solution of 3-(S)-t-butyloxycarbonylamino-2,3,4,5-tetrahydro-1H-[1]benzazepin-2,5-dione (12.5 g) prepared from L-kynurenine as described in Australian J. Chemistry Vol. 33, 633–40 (1980), and t-butyl bromoacetate (10.1 g) in acetone (700 ml) was stirred at room temperature under a dry nitrogen atmosphere. Potassium carbonate (12.5 g) was added in one portion and the resulting suspension was stirred at room temperature for 16 hours. The potassium salts were filtered off and the filtrate evaporated to dryness. The residue was partitioned between ethyl acetate (250 ml) and $H_2O$ (250 ml). The layers were separated and the organic phase dried (sodium sulfate). The residue was triturated wth petroleum ether (350 ml; bp 30°–60°) to give 3-(S)-t-butyloxycarbonylamino-1-t-butyloxycarbonylmethyl-2,3,4,5-tetrahydro-1H-[1]benzazepin-2,5-dione, m.p. 75°–77° C., $[alpha]_D = -172°$ (c=0.96 in DMF).

A solution of 3-(S)-t-butyloxycarbonylamino-1-t-butyloxycarbonylmethyl-2,3,4,5-tetrahydro-1H-[1]benzazepin-2,5-dione (8.0 g) in ethanol (500 ml) containing platinum oxide (800 mg) was hydrogenated at atmospheric pressure and at room temperature for two hours. The catalyst was filtered off and the filtrate evaporated to give 3-(S)-t-butyloxycarbonylamino-1-t-butyloxycarbonylmethyl-5-hydroxy-2,3,4,5-tetrahydro-1H-[1]benzazepin-2-one, $[\alpha]_D = -173°$ (c=1.8 in DMF).

A suspension of 3-(S)-t-butyloxycarbonylamino-1-t-butyloxycarbonylmethyl-5-hydroxy-2,3,4,5-tetrahydro-1H-[1]benzazepin-2-one (3.0 g), dicyclohexylcarbodiimide (5.0 g), and cuprous chloride (500 mg) was mechanically stirred and heated at 80° for 16 hours under a dry nitrogen atmosphere. The mixture was cooled, diluted with methylene chloride (100 ml), and filtered. The solids were discarded. The filtrate was washed with 7% NH4OH (4×75 ml), followed by 1×100 ml with water, and saturated sodium chloride (100 ml). The organic phase was dried (sodium sulfate) and evaporated to give a mixture of the desired adduct and excess dicyclohexylcarbodiimide.

This mixture (5.5 g) was dissolved in ethyl acetate (200 ml) and placed in a pressure bottle. 10% Pd/C (3.0 g) was added and the mixture was hydrogenated at 3 atmospheres pressure and at 40° C. for 16 hours. The catalyst was filtered off and the filtrate evaporated. The residue was triturated with ether (75 ml) to give a white solid, 3-(S)-t-butyloxycarbonylamino-1-t-butyloxycarbonylmethyl-2,3,4,5-tetrahydro-1H-[1]benzazepin-2-one, m.p. 145°–147°, $[\alpha]_D = -194°$ (c=0.46 in DMF).

A solution of 3-(S)-t-butyloxycarbonylamino-1-t-butyloxycarbonylmethyl-5-hydroxy-2,3,4,5-tetrahydro-1H-[1]benzazepin-2-one (described above, 3.0 g) in acetic anhydride (50 ml) was heated at 80° under a dry nitrogen atmosphere for 2 hours. The acetic anhydride was evaporated. The residue was dissolved in ethyl acetate (75 ml) and washed with saturated sodium bicarbonate (50 ml), water (50 ml), and saturated sodium chloride (50 ml). The organic phase was dried (sodium sulfate), evaporated, and the residue triturated with ether (50 ml) to give 3-(S)-t-butyloxycarbonylamino-1-t-butyloxycarbonylmethyl-5-acetoxy-2,3,4,5-tetrahydro-1H-[1]benzazepin-2-one, m.p. 164°–166.5° C., $[\alpha]_D = -169°$ (c=0.36 in DMF).

A solution of 3-(S)-t-butyloxycarbonylamino-1-t-butyloxycarbonylmethyl-5-acetoxy-2,3,4,5-tetrahydro-1H-[1]benzazepin-2-one (2.2 g) in ethanol (300 ml) containing 10% Pd/C (2.0 g) was placed in a pressure bottle and hydrogenated at 3 atmospheres pressure and 70° for 3 days. The catalyst was filtered off and the filtrate evaporated to give 3-(S)-t-butyloxycarbonylamino-1-t-butyloxycarbonylmethyl-2,3,4,5-tetrahydro-1H-[1]benzazepin-2-one, m.p. 164°–165° $[\alpha]_D = -200.6°$ (c=0.64 in DMF).

Hydrogen chloride gas was bubbled through a solution of 3-(S)-t-butyloxycarbonylamino-1-t-butyloxycarbonylmethyl-2,3,4,5-tetrahydro-1H-[1]benzazepin-2-one (0.85 g) in ethyl acetate (40 ml) for 2 hours. Nitrogen was then bubbled through the solution for 0.5 hour. The ethyl acetate was evaporated and the white solid residue immediately dissolved in ethanol (40 ml). Propylene oxide (5 ml) was added and the mixture was stirred at room temperature for 16 hours. The white solid which had precipitated was collected by filtration to give 3-(S)-amino-1-carboxymethyl-2,3,4,5-tetrahydro-1H-[1]benzazepin-2-one, m.p. 275°–276° C., $[\alpha]_D = -287°$ (c=0.71, 1N HCl) which was condensed with ethyl benzylpyrurate in the presence of sodium cyanoborohydride as described above.

EXAMPLE 13

1-Carboxymethyl-3-(1-carboxy-3-phenyl)propylamino-5-hydroxy-2,3-4,5-tetrahydro-1H-[1]benzazepin-2-one To a solution of 1-benzyloxycarbonylmethyl-3-(1-carboxy-3-phenyl)propylamino-2,5-dihydro-1H-[1]benzazepin-2,5-dione (1.00 g) in glacial acetic acid (50 ml) was added platinum oxide (0.10 g). The resulting mixture contained in a pressure bottle was hydrogenated at 43 psi. for 5 hours. The catalyst was removed by filtration, the filtrate concentrated, and the resulting oil triturated with anhydrous ethanol. The resulting solid was collected, dried, and suspended in water (10 ml). The suspension was stirred for 1.5 hours. The solid was collected and dried to give impure 1-carboxymethyl-3-(1-carboxy-3-phenylpropylamino-5-hydroxy-2,3,4,5-tetrahydro-1H-[1]benzazepin-2-one melting with decomposition at 179°.

The starting material was prepared as follows:

Benzyl bromoacetate (9.16 g, 0.04 mole) was added dropwise to a mixture of 3-methoxy-2,5-dihydro-1H-[1]benzazepine-2,5-dione [8.13 g, 0.04 mole, prepared as described in the Canadian J. Chem., 52, 610 (1974)] powdered potassium hydroxide (2.24 g, 0.04 mole) and tetrabutylammonium bromide (1.29 g, 0.004 mol) in 1 L of acetonitrile with stirring at room temperature. Upon complete addition, the suspension was stirred at room temperature for 64 hours, filtered, and the filtrate concentrated under reduced pressure to give a partially crystalline oil. This oil was triturated with ether to give a solid which was suspended and stirred in ethyl acetate (100 ml) for 1.5 hours. The insoluble material was filtered off and the filtrate concentrated to give the crude 1-benzyloxycarbonylmethyl-3-methoxy-2,5-dihydro-1H-[1]benzazepin-2,5-dione which was used directly in the next step.

To a 1.0M solution of potassium t-butoxide (0.64 g, 0.0057 mol) in t-butanol (5.7 ml) stirring under nitrogen at room temperature was added (+)-homophenylalanine (1.02 g; 0.0057 mol) in one portion. The resulting suspension and t-butanol (4.3 ml) was heated until most of the suspended solid was dissolved. Upon cooling, a suspension was obtained. This suspension was added, in portions, via pipette to a refluxing solution of 1-benzyloxycarbonylmethyl-3-methoxy-2,5-dihydro-1H-[1]benzazapin-2,5-dione (2.00 g) in t-butanol (40 ml) stirring under nitrogen over a period of 10 minutes. During the addition, a yellow precipitate formed. Upon complete addition, the resulting suspension was refluxed for 3 hours. The suspension was filtered, the resulting gummy solid was washed with petroleum ether and dissolved in water (20 ml). The solution was filtered, acidified to pH 5 with 3N hydrochloric acid, the resulting crude 1-benzyloxycarbonylmethyl-3-(1-carboxy-3-phenylpropylamino)-2,5-dihydro-1H-[1]benzazepin-2,5-dione was collected and used directly for the preparation of the title compound.

EXAMPLE 14

Analogous to the methods disclosed herein, the following compounds of formula IA wherein $X = H_2$, $R_2$ and $R_5 = H$, $R_6 = OC_2H_5$ and $R_7 = OH$ can be prepared:

| No. | $R_1$ | $R_3$ | $R_4$ |
|---|---|---|---|
| 1 | $C_6H_5CH_2$ | H | H |
| 2 | $C_6H_5CH_2$ | 7-OCH$_3$ | 8-OCH$_3$ |
| 3 | $C_6H_5CH_2CH_2$ | 7-Cl | H |
| 4 | $C_6H_5CH_2CH_2$ | 8-CH$_3$ | H |
| 5 | $C_6H_5CH_2CH_2$ | 8-OCH$_3$ | H |
| 6 | p-ClC$_6$H$_4$CH$_2$CH$_2$ | H | H |
| 7 | CH$_3$ | H | H |

The starting substituted 2,3,4,5-tetrahydro-1H-[1]benzazepin-2-ones for compounds 2–5 are prepared as follows:

The 7-chloro-2,3,4,5-tetrahydro-1H-[1]benzazepin-2-one, mp 164°–5°, is prepared as described in British Pat. No. 1,359,285.

The 8-methyl-2,3,4,5-tetrahydro-1H-[1]-benzazepin-2-one is prepared by the method of Huisgen, Liebigs Ann. Chem. 574, 171 (1951), mp 153°–154°.

The 7,8-dimethoxy-2,3,4,5-tetrahydro-1H-[1]-benzazepin-2-one was prepared as follows:

A solution of 24 g of 6,7-dimethoxy- -tetralone (Snider, T. et al, Org. Prep. Proced. Int., 5, 291 (1973) in ethanol (300 ml) and water (60 ml) was treated at reflux for two hours with hydroxylamine hydrochloride (16 g) and sodium hydroxide (25 g) to form the oxime. The reaction mixture was poured into 500 ml of an ice/water mixture and extracted with 3×300 ml portions of dichloromethane. The combined extracts were washed with 200 ml water, dried over anhydrous magnesium sulfate and evaporated to yield 25 g of the oxime, mp 154°–156°.

The oxime was redissolved in 170 ml of dichloromethane and 170 ml of polyphosphate ester (Fieser and Fieser: Reagents for Organic Synthesis, Wiley N.Y. 1967, P.892) was added. The reaction mixture was refluxed for 18 hours. The dichloromethane layer was separated, treated with charcoal and dried over magnesium sulfate to yield 11.0 g of 7,8-dimethoxy-2,3,4,5-tetrahydro-[1H]-1-benzazepin-2-one, m.p. 153°–156°.

The 8-methoxy-2,3,4,5-tetrahydro-1H-[1]benzazepin-2-one, m.p. 132°–4° was similarly prepared from 7-methoxy-α-tetralone.

3-Amino-7-chloro-2,3,4,5-tetrahydro-1H[1]benzazepin-2-one was synthesized as follows:

A solution of 3-amino-2,3,4,5-tetrahydro-1H[1]benzazepin-2-one (4.0 g), 2-t-butyloxycarbonyloxyimino-2-phenylacetonitrile (6.1 g) and triethylamine (5 ml) in water (20 ml) and dioxane (25 ml) was stirred at room temperature for 18 hours. The resulting solid was filtered off and washed with water. Recrystallization from ethyl acetate gave 3-t-butyloxycarbonylamino-2,3,4,5-tetrahydro-1H-[1]benzazepin-2-one, m.p. 199°–201°.

Chlorine gas was bubbled through a solution of 3-t-butyloxycarbonylamino-2,3,4,5-tetrahydro-1H[1]benzazepin-2-one (1.5 g) in acetic acid (20 ml) for 10 minutes. The reaction mixture was stirred for an additional 10 minutes. The solid which had precipitated was collected, suspended in water (30 ml) and aqueous ammonia was added until basic. Filtration gave 3-amino-7-chloro-2,3,4,5-tetrahydro-1H-[1]benzazepin-2-one, m.p. 170°–1°.

EXAMPLE 15

Preparation of 10,000 tablets each containing 10 mg of the active ingredient of Example 1:

| Formula: | |
|---|---|
| 1-Carboxymethyl-3-(1-ethoxycarbonyl-3-phenylpropylamino)-2,3,4,5-tetrahydro-1H—[1]benzazepin-2-one. | 100.00 g |
| Lactose | 1,157.00 g |
| Corn starch | 75.00 g |
| Polyethylene glycol 6,000 | 75.00 g |
| Talcum powder | 75.00 g |
| Magnesium stearate | 18.00 g |
| Purified water | q.s. |

Procedure

All the powders are passed through a screen with openings of 0.6 mm. Then the drug substance, lactose, talcum, magnesium stearate and half of the starch are mixed in a suitable mixer. The other half of the starch is suspended in 40 ml of water and the suspension added to the boiling solution of the polyethylene glycol in 150 ml of water. The paste formed is added to the powders which are granulated, if necessary, with an additional amount of water. The granulate is dried overnight at 35°, broken on a screen with 1.2 mm openings and compressed into tablets using concave punches with 6.4 mm diameter, uppers bisected.

EXAMPLE 16

Preparation of an injectable formulation containing 25 mg of the active ingredient of Example 1 per 5 ml of solution:

| Formula: | |
|---|---|
| 1-Carboxymethyl-3-(1-ethoxycarbonyl-3-phenylpropylamino)-2,3,4,5-tetrahydro-1H—[1]benzazepin-2-one hydrochloride | 25.0 g |
| Propylparaben | 1.0 g |
| Water for injection q.s. | 5000.0 ml |

The active ingredient and preservative are dissolved in 3500 ml of water for injection and the solution is diluted to 5000 ml. The solution is filtered through a sterile filter and filled into injection vials under sterile conditions each vial containing 5 ml of the solution.

EXAMPLE 17

Preparation of 10,000 capsules each containing 20 mg of the active ingredient of Example 9.

| Formula: | |
| --- | --- |
| 1-Carboxymethyl-3-(1-carboxy-3-phenyl-propylamino)-2,3,4,5-tetrahydro-1H—[1]-benzazepin-2-one | 200.00 g |
| Lactose | 1,700.0 g |
| Talcum powder | 100.0 g |

Procedure

All the powders are passed through a screen with openings of 0.6 mm. Then the drug substance is placed in a suitable mixer and mixed first with the talcum, then with the lactose until homogenous. No. 3 capsules are filled with 200 mg; using a capsule filling machine.

Analogously, tablets, injectable formulations or capsules are prepared from the remaining compounds of the invention, e.g., those illustrated by the examples herein.

EXAMPLE 18

1-Carboxymethyl-3S-(1R-ethoxycarbonyl-3-phenylpropylamino) 2,3,4,5-tetrahydro-1H-[1]benzazepin-2-one The methyl ethyl ketone filtrate from the crystallization of 1-carboxymethyl-3S-(1S-ethoxycarbonyl-3-phenylpropylamino)-2,3,4,5-tetrahydro-1H-[1]benzazepin-2-one hydrochloride in Example 12 was evaporated, and the residue triturated with ethyl acetate (50 ml). The resulting solid was distributed between ethyl acetate (100 ml) and water (100 ml) adjusted to pH 4.3 with concentrated hydrochloric acid. The layers were separated and the aqueous phase extracted with ethyl acetate (2×100 ml). The combined ethyl acetate solutions were dried over sodium sulfate and the solvent removed under reduced pressure. The residue was separated into its components by high pressure liquid chromatography with a $C_{18}$ reverse phase preparative column and using water/methanol (3:7) containing 0.05% acetic acid as the solvent. An additional quantity of the S,S isomer of example 12 was thus obtained, as well as the S,R isomer. The material corresponding to the S,R isomer was dissolved in dichloromethane (75 ml), and hydrogen chloride gas bubbled in for five minutes. The solvent was evaporated under reduced pressure and the residue recrystallized from methyl ethyl ketone to give 1-carboxymethyl-3S-(1R-ethoxycarbonyl-3-phenylpropylamino-2,3,4,5-tetrahydro-1H-[1]benzazepine-2-one hydrochloride, m.p. 181°–183°, $[\alpha]_D = -188°$ (C=0.8 in ethanol).

EXAMPLE 19

1-Carboxymethyl-3S-(1S-carboxy-3-phenylpropylamino)-2,3,4,5-tetrahydro-1H-[1]benzazepin-2-one A solution of sodium hydroxide (0.27 g) in water (2 ml) was added to a solution of 1-carboxymethyl-3S-(1S-ethoxycarbonyl-3-phenylpropylamino)-2,3,4,5-tetrahydro-1H-[1]benzazepin-2-one hydrochloride (1 g) in methanol (10 ml). The reaction mixture was stirred for 18 hours at room temperature and the solvents removed under reduced pressure. The residue was dissolved in water (25 ml), and the pH adjusted to 3 by the addition of 4N hydrochloric acid. The resulting solid was filtered off, washed with water, and dried to give 1-carboxymethyl-3S-(1S-carboxy-3-phenylpropylamino)-2,3,4,5-tetrahydro-1H-[1]benzazepin-2-one, m.p. 270°–272°, $[\alpha]_D = -200.5°$ (c=1, 3% aqueous ammonia).

EXAMPLE 20

1-Ethoxycarbonylmethyl-3-(1-benzyloxycarbonyl-3-phenylpropylamino)-2,3,4,5-tetrahydro-1H-[1]benzazepin-2-one A solution of 3-(1-benzyloxycarbonyl-3-phenylpropylamino)-2,3,4,5-tetrahydro-1H-[1]-benzazepin-2-one (5.0 g) in dry dimethylformamide was added under a nitrogen atmosphere to a stirred suspension of sodium hydride [from the 60% mineral oil dispersion (0.5 g) washed with petroleum ether (3×80 ml)] in dry dimethylformamide (100 ml) at room temperature. Stirring was continued for an additional 30 minutes at room temperature, when a solution of ethyl bromoacetate (2.0 g) in dry dimethylformamide (10 ml) was added. After an additional 30 minutes at room temperature the reaction mixture was heated to 50°, and maintained at that temperature for 18 hours. The reaction mixture was cooled to room temperature and the solvent removed under high vacuum. Water (150 ml) was added and the solution extracted with ethyl acetate (2×300 ml). The combined ethyl acetate solutions were washed with water (100 ml), dried over $MgSO_4$, and the solvent removed under reduced pressure to give a brown oil which was chromatographed on silica gel (250 g). Elution with toluene/ethyl acetate (9:1; 600 ml) gave an oil, characterized as isomer A of the title compound. Elution with an additional 1000 ml of the solvent mixture gave an oil characterized as isomer B of the title compound.

EXAMPLE 21

1-Ethoxycarbonylmethyl-3-(1-carboxy-3-phenylpropylamino)-2,3,4,5-tetrahydro-1H-[1]benzazepin-2-one 1-Ethoxycarbonylmethyl-3-(1-benzyloxycarbonyl-3-phenylpropylamino)-2,3,4,5-tetrahydro-1H-[1]-benzazepine-2-one (isomer B of Example 20, 1.1 g) in ethanol (150 ml) was hydrogenated at room temperature and atmospheric pressure using palladium on charcoal (0.5 g) as catalyst. After uptake of hydrogen had terminated, the catalyst was filtered off, and the solvent removed under reduced pressure to give a semi-solid. Trituration with ether (30 ml) yielded isomer B of the title compound, m.p. 175°–177° C.

EXAMPLE 22

1-Carboxymethyl-3-(1-ethoxycarbonyl-3-phenylpropylamino)-8-methoxy-2,3,4,5-tetrahydro-1H-[1]benzazepine-2-one (isomer B)

A solution of 3-amino-1-carboxymethyl-8-methoxy-2,3,4,5-tetrahydro-1H-[1]-benzazepin-2-one (4.0 g) and ethyl benzylpyruvate (9.4 g) in a mixture of acetic acid (35 ml) and methanol (35 ml) was stirred for 1 hour. A solution of sodium cyanoborohydride (1.1 g) in methanol (50 ml was then added slowly over the course of 5 hours. After stirring an additional 16 hours, concentrated hydrochloric acid (4 ml) was added and stirring was continued for 1 hour. The solvents were removed at reduced pressure and the residue was partitioned between water (75 ml) and ether (35 ml). The pH was adjusted to 9.4 and the ether layer was separated and discarded. The aqueous layer was acidified to pH 4.3 and extracted with ethyl acetate (3×50 ml). The combined ethyl acetate solutions were dried over magnesium sulfate and the solvent was removed at reduced pressure. Hydrogen chloride gas was bubbled into a solution of the crude product in methylene chloride (100 ml) for 5 minutes. The solution was evaporated and the residue was stirred in ether (75 ml). The product was collected by filtration to give an approximately 70:30 diastereomeric mixture as determined by high pressure liquid chromatography.

The product was recrystallized from 3-pentanone to give 1-carboxymethyl-8-methoxy-3-(1-ethoxycarbonyl-3-phenylpropylamino)-2,3,4,5-tetrahydro-1H-[1]-benzazepin-2-one hydrochloride (isomer B) melting at 240°–245° (dec.).

The starting material was prepared as follows:

A solution of 8-methoxy-2,3,4,5-tetrahydro-1H[1]benzazepin-2-one (7.0 g, described in Example 14) and phosphorus pentachloride (30.0 g) in xylene (200 ml) was heated with stirring under an atmosphere of nitrogen to 90° (oil bath temperature) during 30 minutes with pauses at 30° and at 50°. There was a copious evolution of hydrogen chloride gas. The temperature was maintained at 90° for 30 minutes. The reaction mixture was filtered while hot to remove a small amount of suspended solid, and the filtrate was evaporated under reduced pressure until all the solvent was removed. The residue was added with stirring to saturated aqueous sodium carbonate (20 ml). The product was filtered after the solidification process was complete, slurried in ethanol (30 ml), washed with ethanol (10 ml) and ether (10 ml) and dried to give 3,3-dichloro-8-methoxy-2,3,4,5-tetrahydro-1H-[1]benzazepin-2-one, m.p. 148°–150°.

A solution of 3,3-dichloro-8-methoxy-2,3,4,5-tetrahydro-1H-[1]-benzazepin-2-one (20 g) and anhydrous sodium acetate (13.2 g) in glacial acetic acid (250 ml) was hydrogenated at atmospheric pressure using 10% Pd/C (1 g) as catalyst, until the uptake of hydrogen ceased. The catalyst was filtered off and the acetic acid was evaporated under reduced pressure. Water (100 ml) was added to the residue and the suspension stirred for 1 hour. The solid was filtered, washed with water (50 ml), and dried to give 3-chloro-8-methoxy-2,3,4,5-tetrahydro-1H-[1]-benzazepin-2-one, m.p. 162°–163°.

A solution of 3-chloro-8-methoxy-2,3,4,5-tetrahydro-1H-[1]-benzazepin-2-one (12.5 g) and sodium azide (4.3 g) in dimethylsulfoxide (150 ml) was maintained at 80° under an atmosphere of nitrogen for 3 hours. The reaction mixture was poured into ice/water (300 ml) and the suspension was stirred for 30 minutes. The solid was filtered off, washed with water (50 ml) and dried to give 3-azido-8-methoxy-2,3,4,5-tetrahydro-1H-[1]-benzazepin-2-one, m.p. 136°–138°.

3-Azido-8-methoxy-2,3,4,5-tetrahydro-1H-[1]-benzazepin-2-one (5 g) was added in one portion to a stirred suspension of potassium hydroxide (1.3 g) and tetrabutylammonium bromide (0.7 g) in tetrahydrofuran (50 ml) maintained at 0° under a nitrogen atmosphere. Stirring was continued for 5 minutes, then a solution of ethyl bromoacetate (3.6 g) in tetrahydrofuran (15 ml) was added during 5 minutes. The reaction mixture was allowed to warm to room temperature while stirring for an additional 2 hours. The reaction mixture was filtered and the tetrahydrofuran was removed at reduced pressure. The residue was partitioned between water (50 ml) and ether (100 ml). The organic phase was washed with 2N hydrochloric acid (10 ml), dried over magnesium sulfate and the solvent removed under reduced pressure to give 3-azido-1-ethoxycarbonylmethyl-8-methoxy-2,3,4,5-tetrahydro-1H-[1]-benzazepin-2-one, m.p. 90°–91°.

A suspension of 3-azido-1-ethoxycarbonylmethyl-8-methoxy-2,3,4,5-tetrahydro-1H-[1]-benzazepin-2-one (13.8 g) in methanol (75 ml) was treated with a solution of sodium hydroxide (1.9 g) in water (75 ml). The reaction mixture was stirred at 40°–45° for 2 hours. Water (100 ml) was added and the mixture was acidified with concentrated hydrochloric acid (10 ml) and extracted with methylene chloride (3×75 ml). The combined methylene chloride solutions were dried over magnesium sulfate and evaporated at reduced pressure to give 3-azido-1-carboxymethyl-8-methoxy-2,3,4,5-tetrahydro-1H-[1]-benzazepin-2-one, m.p. 145°–147°.

A solution of 3-azido-1-carboxymethyl-8-methoxy-2,3,4,5-tetrahydro-1H-[1]-benzazepin-2-one (11 g) in a mixture of ethanol (250 ml) and water (50 ml) was hydrogenated for 3 hours on a Parr shaker at 3 atmospheres pressure and room temperature using 10% Pd-C (0.5 g) as catalyst. 2N Hydrochloric acid (50 ml) was added, and the catalyst was filtered off. The solvent was removed at reduced pressure, and the residue dissolved in a mixture of water (50 ml) and ethanol (50 ml). Propylene oxide (25 ml) was added and the mixture was stirred for 1 hour. The solvents were removed under reduced pressure to give 3-amino-1-carboxymethyl-8-methoxy-2,3,4,5-tetrahydro-1H-[1]-benzazepin-2-one, m.p. >300°.

EXAMPLE 23

1-(1-Carboxyethyl)-3-(1-ethoxycarbonyl-3-phenylpropylamino)-2,3,4,5-tetrahydro-1H-[1]-benzazepin-2-one Hydrochloride A solution of 3-amino-1-(1-carboxyethyl)-2,3,4,5-tetrahydro-1H-[1]-benzazepin-2-one hydrochloride (3 g) and ethyl benzylpyruvate (6.5 g) in acetic acid (30 ml) and methanol (30 ml) was stirred at room temperature for 1 hour. Sodium cyanoborohydride (0.8 g) in methanol (10 ml) was added over 4 hours. The reaction mixture was stirred at room temperature for 24 hours. Concentrated hydrochloric acid (2 ml) was added and the mixture was stirred for 1 hour. The solvents were removed at reduced pressure and the residue was partitioned between water (50 ml) and ether (30 ml). The pH was adjusted to 9.4, the ether layer was separated and discarded. The aqueous solution was adjusted to pH 4.3 and extracted with ethyl acetate (3×50 ml). The combined ethyl acetate solutions were dried over magnesium sulfate and the solvent removed under reduced pressure. Hydrogen chloride was bubbled into a solution of the crude product in methylene chloride (10 ml) for 2 minutes. The solution was evaporated to give 1-(1-carboxyethyl)-3-(1-ethoxycarbonyl-3-phenylpropylamino)-2,3,4,5-tetrahydro-1H-[1]-benzazepin-2-one hydrochloride, as a mixture of diastereomers, m.p. 87°–94°.

The starting material was prepared as follows:

3-Azido-2,3,4,5-tetrahydro-1H-[1]benzazepin-2-one (as prepared in example 1,5 g) was added in one portion to a stirred suspension of potassium hydroxide (1.8 g) and tetrabutylammonium bromide (0.8 g) in tetrahydrofuran (50 ml) maintained at 0° under a nitrogen atmosphere. Stirring was continued for 5 minutes, then (R)-t-butyl 2-bromopropionate [J. P. Greenstein et al., J. Am. Chem. Soc. 76, 6054 (1954), H. Niedrich and G. Koller, J. Prakt. Chem. 316, 729 (1974)] (5.2 g) in tetrahydrofuran (15 ml) was added during 5 minutes. The reaction mixture was allowed to warm to room temperature while stirring for an additional 2 hours. The reaction mixture was filtered and the tetrahydrofuran removed at reduced pressure. The residue was partitioned between water (50 ml) and ether (100 ml). The organic phase was washed with 2N hydrochloric acid (10 ml), dried over magnesium sulfate, and the solvent evaporated under reduced pressure to give 3-azido-1-(1-t-butyloxycarbonylethyl)-2,3,4,5-tetrahydro-1H[1]-benzazepin-2-one as an oil that was used without further purification.

A solution of 3-azido-1-(1-t-butyloxycarbonylethyl)-2,3,4,5-tetrahydro-1H-[1]-benzazepin-2-one (7 g) in ethanol (70 ml) was hydrogenated on a Parr shaker at 3 atmospheres pressure for 3 hours using 10% Pd-C (0.5 g) as catalyst. The catalyst was removed by filtration and the ethanol removed under reduced pressure to give 3-amino-1-(1-t-butyloxycarbonylethyl)-2,3,4,5-tetrahydro-1H-[1]-benzazepin-2-one as an oil. High pressure liquid chromatography (HPLC) indicated that the product was an approximately 1:1 mixture of diastereomers. This material was used without further purification.

A solution of the above 3-amino-1-(1-t-butyloxycarbonylethyl)-2,3,4,5,-tetrahydro-1H-[1]-benzazepin-2-one (4.7 g) in trifluoroacetic acid (25 ml) was stirred at room temperature for 1 hour. The trifluoroacetic acid was removed under reduced pressure and the residue dissolved in ether (100 ml). Hydrogen chloride was bubbled into the solution until precipitation ceased. The solid was collected by filtration to give 3-amino-1-(1-carboxyethyl)-2,3,4,5-tetrahydro-1H-[1]-benzazepin-2-one hydrochloride, m.p. 165°–176°. HPLC indicated that the product was an approximately 1:1 mixture of diastereomers.

EXAMPLE 24

1-Ethoxycarbonylmethyl-3S-(1S-ethoxycarbonyl-3-phenylpropylamino)-2,3,4,5-tetrahydro-1H-[1]benzazepin-2-one A solution of 3S-amino-1-ethoxycarbonylmethyl-2,3,4,5-tetrahydro-1H-[1]-benzazepin-2-one (1.5 g), ethyl 2-bromo-4-phenylbutyrate (1.6 g), and triethylamine (0.8 ml) in dimethylformamide (37 ml) was stirred under nitrogen for 18 hours at 70°. The dimethylformamide was then removed under reduced pressure. The residue was taken up in ethyl acetate (70 ml), washed with water (5×25 ml), dried over magnesium sulfate, and evaporated. The product mixture was then separated on a silica gel flash chromatography system with ethyl acetate/hexanes (40:60) as solvent to yield about equal quantities of 1-ethoxycarbonylmethyl-3S-(1S-ethoxycarbonyl-3-phenylpropylamino)-2,3,4,5-tetrahydro-1H-[1]benzazepin-2-one [NMR (CDCl$_3$) δ4.52 (q,2H)] the S,S enantiomer of the compound of example 10, and its diastereomer, 1-ethoxycarbonylmethyl-3S-(1R-ethoxycarbonyl-3-phenylpropylamino)-2,3,4,5-tetrahydro-1H-[1]benzazepin-2-one; NMR (CDCl$_3$): δ4.50 (q, 2H).

TLC: (silica gel, ethyl acetate/hexane 40:60): the (S,S) isomer had R$_f$=0.24 and the (S,R) isomer R$_f$=0.33.

EXAMPLE 25

1-Carboxymethyl-3S-(1S-ethoxycarbonyl-3-phenylpropylamino)-2,3,4,5-tetrahydro-1H-[1]benzazepin-2-one 2N Potassium hydroxide (0.26 ml) was added dropwise to a solution of 1-ethoxycarbonylmethyl-3S-(1S-ethoxycarbonyl-3-phenylpropylamino)-2,3,4,5-tetrahydro-1H-[1]benzazepin-2-one (0.25 g) in ethanol (5 ml), stirring at room temperature under a nitrogen atmosphere. After stirring for one hour the ethanol was evaporated and the residue was dissolved in water (5 ml), acidified with 2N hydrochloric acid to pH2 and extracted with ethyl acetate (2×30 ml). The combined ethyl acetate solutions were washed with saturated sodium chloride solution (5 ml), dried over magnesium sulfate and evaporaed to dryness to yield 1-carboxymethyl-3S-(1S-ethoxycarbonyl-3-phenylpropylamino)-2,3,4,5-tetrahydro-1H-[1]benzazepin-2-one, the compound of example 12.

EXAMPLE 26

1-Carboxymethyl-7-chloro-3-(1-ethoxycarbonyl-3-phenylpropylamino)-2,3,4,5-tetrahydro-1H-[1]benzazepin-2-one, isomer B Chlorine was bubbled through a solution of 1-carboxymethyl-3-(1-ethoxycarbonyl-3-phenylpropylamino)-2,3,4,5-tetrahydro-1H-[1]benzazepine-2-one (isomer B, 1.5 g) in acetic acid (25 ml), stirring at room temperature. A white solid precipitated out; chlorine was bubbled through the reaction mixture until the reaction was complete. The solid was filtered off and separated by reverse phase HPLC using a C$_{18}$ column and methanol/0.1% aqueous ammonium carbonate (1:1) as solvent. The appropriate fraction was dissolved in methanol/ethyl acetate (1:1, 50 ml) and hydrogen chloride bubbled through the solution. The solution was evaporated, the residue was suspended in ether (100 ml) and the suspension was filtered to give 1-carboxymethyl-7-chloro-3-(1-ethoxycarbonyl-3-phenylpropylamino)-2,3,4,5-tetrahydro-1H-[1]benzazepin-2-one hydrochloride, m.p. 149°–151° (isomer B).

EXAMPLE 27

1-Carboxymethyl-3S-(1S-ethoxycarbonyl-3-phenylpropylamino)2,3,4,5-tetrahydro-1H-[1]benzazepin-2-one Hydrochloride 3(S)-Amino-1-carboxymethyl-2,3,4,5-tetrahydro-1H-[1]benzazepine-2-one sodium salt (619 g) having [α]$_D^{25}$= −304.4° (c=1.08 in water), ethyl benzylpyruvate (1.96 Kg), anhydrous ethyl alcohol (5.88 L) and glacial acetic acid (5.88 L) were combined and stirred at 20°–25° for 1.5 hours. A solution of sodium cyanobrohydride (0.179 Kg) in anhydrous ethyl alcohol (2.2 L) was added at a constant slow rate over 24 hours. After addition was complete, the reaction was stirred for 24 hours. 12N Hydrochloric acid (500 ml) was added to the reaction and the solvent was evaporated at 35°–40°/3 mm Hg. The oil which remained was combined with ice (3 kg), water (3 L) and diethyl ether (3 L), and the pH of the mixture was adjusted to 9–9.5 with 10N sodium hydroxide solution (1.735 L). The aqueous portion was removed and an additional 8 L of diethyl ether was added to the ether portion to oil out additional product. The ether immiscible portion was removed and combined with the aqueous portion. The ether extract was then washed with water (2×1 L), the washes were incorporated with the aqueous/oil portions from above and the mixture was adjusted to pH 4.25-4.35 with 12N hydrochloric acid (550-650 ml). The mixture was extracted with ethyl acetate (3×2 L), the combined ethyl acetate portions were washed with water (2 L) and dried with anhydrous magnesium sulfate (500 g). The drying agent was removed by filtration and the solvent was thoroughly removed by evaporation at 40°/3 mm Hg. The resulting oil was dissolved in ethyl acetate (4.5 L) and 28% ethereal hydrogen chloride (309 g) was added with vigorous stirring. Diethyl ether (1.5 L) was added and the mixture was stirred for 1 hour. The solid was collected and was washed with ethyl acetate (2×500 ml) and diethyl ether (3×1 L). Drying at 50°/3 mm Hg afforded crude product consisting of approximately 65% of the desired 1-carboxymethyl-3S-(1S-ethoxycarbonyl)-3-phenylpropylamino)-2,3,4,5-tetrahydro-1H[1]-benzazepin-2-one, identical to the material example 12, as determined by reverse phase HPLC on a $C_{18}$ column with a mixture of methanol, water, and acetic acid (75:25:0.02) as eluent.

Hydrogen chloride gas was added in a steady stream to a suspension of the above crude product in dichloromethane (26.9 L). A solution was obtained after 40 minutes when the addition of the gas was stopped. The solution was filtered to remove trace insolubles and diethyl ether (10.75 L) was added.

The suspension was stirred overnight at ambient temperature and the solid was collected by filtration and washed with dichloromethane (4×500 ml) and diethyl ether (3×1 L). Drying afforded purer product as the hydrochloride salt, mp 175°-178°.

1.88 Kg of above hydrochloride salt was combined with dichloromethane (18 L). The suspension was again treated with hydrogen chloride gas to complete solution. Diethyl ether (7.2 L) was added. The suspension was stirred for 3 hours and filtered. The collected solid was washed with dichloromethane (2×1 L) and diethyl ether (2×1 L) and was dried to give product m.p. 183°-185° (HPLC indicated that the product was approximately 96% pure).

1.28 Kg of the above salt was combined with chloroform (4 L) and the mixture was heated at reflux temperature for 10 minutes. Heating was discontinued and the mixture was stirred for 4 hours and filtered. The solid was washed with chloroform (2×200 ml) and diethyl ether (3×500 ml), dried and sieved to give 1-carboxymethyl-3S-(1S-ethoxycarbonyl)-3-phenylpropylamino)-2,3,4,5-tetrahydro-1H-[1]benzazepin-2-one hydrochloride, m.p. 184°-186°, $[\alpha]_D^{25} = -139.26°$ (c=0.92, absolute EtOH), and identical to the hydrochloride salt of example 12.

EXAMPLE 28

3-(1-benzyloxycarbonyl-3-phenylpropylamino)-1-carboxymethyl-2,3,4,5-tetrahydro-1H-[1]benzazepin-2-one hydrochloride (Isomer B)

Dry hydrogen chloride gas was bubbled through a solution of 3-(1-benzyloxycarbonyl-3-phenylpropylamino)-1-t-butyloxycarbonylmethyl-2,3,4,5-tetrahydro-1H-[1]benzazepin-2-one (4.0 g, see Example 7) in ethyl acetate (100 ml) for 20 minutes while stirring at 0°. The reaction mixture was evaporated under reduced pressure and the resulting solid triturated with ether (50 ml). The solid was filtered off, washed with ether (15 ml) and ethyl acetate (15 ml), and then boiled with ethyl acetate (50 ml). The product was recrystallized from methanol/ethyl acetate to give 3-(1-benzyloxycarbonyl)-3-phenylpropylamino)-1-carboxymethyl-2,3,4,5-tetrahydro-1H-[1]benzazepin-2-one hydrochloride, m.p. 197°-199° (isomer B).

The starting material was prepared as follows:

Potassium t-butoxide (1.2 g) was added to a solution of 3-(1-benzyloxycarbonyl-3-phenylpropylamino)-2,3,4,5-tetrahydro-1H-[1]benzazepin-2-one (3.0 g) and t-butyl bromoacetate (2.2 g) in tetrahydrofuran (100 ml) stirring at room temperature under an atmosphere of dry nitrogen. The reaction mixture was stirred for 20 hours at room temperature, then poured into water (250 ml) and extracted with dichloromethane (2×150 ml). The combined dichloromethane solutions were washed with water (100 ml) and dried over magnesium sulfate. Evaporation of the solvent gave 3-(1-benzyloxycarbonyl-3-phenylpropylamino)-1-t-butyloxycarbonylmethyl-2,3,4,5-tetrahydro-1H-[1]benzazepin-2-one.

EXAMPLE 29

1-Ethoxycarbonylmethyl-3-(1-ethoxycarbonyl-3-phenylpropylamino)-2,3,4,5-tetrahydro-1H-[1]benzazepin-2-one A solution of ethyl 2-(1-ethoxycarbonyl-3-phenylpropylamino)-4-[o-(ethoxycarbonylmethylamino)-phenyl]butyrate (5.6 g) in methanol (100 ml) is added to a solution of sodium methoxide in methanol [prepared from sodium (0.25 g) and methanol (50 ml)] with stirring under a nitrogen atmosphere. The reaction mixture is refluxed for 65 hours, then evaporated under reduced pressure. The residue is distributed between water (50 ml) and dichloromethane (200 ml). The aqueous solution is extracted with dichloromethane (200 ml) and the combined organic solutions washed with water (50 ml) and dried over potassium carbonate. Evaporation of the solvent gives as a mixture of isomers A and B of 1-ethoxycarbonylmethyl-3-(1-ethoxycarbonyl-3-phenylpropylamino)-2,3,4,5-tetrahydro-1H-[1]benzazepin-2-one, which is separated by chromatography on silica gel and converted to the individual maleate salts as described in example 10.

The starting material is obtained as follows:

To a solution of ethyl 2-amino-4-(o-nitrophenyl)butyrate (17.4 g) in 50% aqueous dioxane (130 ml) is added triethylamine (10.5 g) and 2-(tert-butyloxycarbonyloxyimino-2-phenylacetonitrile (18.7 g.). The reaction mixture is stirred at room temperature for 4 hours and then diluted with water (300 ml). The mixture is extracted with ether (2×150 ml) and the aqueous phase acidified with ice-cold 2N hydrochloric acid and extracted with ethyl acetate (2×250 ml). The ethyl acetate layers are combined, washed with water (150 ml) and dried over sodium sulfate. The solvent is removed under reduced pressure to give ethyl 2-t-butyloxycarbonylamino-4-(o-nitrophenyl)butyrate, used without further purification.

A solution of ethyl 2-t-butyloxycarbonylamino-4-(o-nitrophenyl)butyrate (13.0 g) in ethanol (300 ml) is hydrogenated at room temperature and atmospheric pressure, using 10% palladium on charcoal (1 g) as catalyst, until uptake ceases. The catalyst is filtered off. Evaporation of the solvent gives ethyl t-butyloxycarbonylamino-4-(o-aminophenyl)butyrate which is used without further purification for the next step.

A solution of ethyl 2-t-butyloxycarbonylamino-4-(2-aminophenyl)butyrate (10.0 g) and ethyl glyoxylate (4.2 g) in ethanol (120 ml) is hydrogenated at 80° and 3 atmospheres pressure for 72 hours using 10% palladium on charcoal (3 g) as catalyst. The reaction mixture is cooled to room temperature and the catalyst filtered off. The solvent is removed under reduced pressure and the residue distributed between ethyl acetate (150 ml) and water (75 ml). The organic phase is dried over sodium sulfate and the solvent removed under reduced pressure to give ethyl 2-t-butyloxycarbonylamino-4-[o-(ethoxycarbonylmethylamino)phenyl]butyrate which is used without further purification for the next step.

Hydrogen chloride gas is bubbled through a solution of ethyl 2-t-butyloxycarbonylamino-4-[o-(ethoxycarbonylmethylamino)phenyl]butyrate (8.5 g) in ethyl acetate (150 ml) for 30 minutes at room temperature. The solution is evaporated under reduced pressure and the residue dissolved in ethyl acetate (100 ml). The solution is washed with water (3×100 ml) and dried over sodium sulfate. The solvent is removed under reduced pressure to give ethyl 2-amino-4-[o-(ethoxycarbonylmethylamino)phenyl]butyrate used without further purification for the next step.

A solution of ethyl 2-amino-4-[o-(ethoxycarbonylmethylamino)phenyl]butyrate (4.7 g) and ethyl benzylpyruvate (12.4 g) in acetic acid (35 ml) and methanol (35 ml) is stirred at room temperature under nitrogen for 1 hour. Sodium cyanoborohydride (1.6 g) in methanol (15 ml) is added dropwise over 4 hours. The reaction mixture is stirred at room temperature for 24 hours. Concentrated hydrochloric acid (2 ml) is added dropwise, and the mixture stirred at room temperature for 1 hour. The reaction mixture is evaporated to dryness, and the residue partitioned between water (75 ml) and ether (75 ml) and adjusted to pH 2 with 6N HCl. The layers are separated, and the aqueous phase extracted with ether (2×75 ml). The ether extracts are discarded and the aqueous layer adjusted to pH 9 with 40% sodium hydroxide, and extracted with ethyl acetate (3×50 ml). The ethyl acetate extracts are dried over sodium sulfate and the solvent removed under reduced pressure to give ethyl 2-(1-ethoxycarbonyl-3-phenylpropylamino)-4-[(o-ethoxycarbonylmethylamino)phenyl]butyrate which is used directly for preparing the final product above.

EXAMPLE 30

Ethyl 2-amino-4-phenylbutyrate is treated under conditions of reductive alkylation as described in the previous examples with 1-ethoxycarbonylmethyl-2,3,4,5-tetrahydro-1H-[1]benzazepine-2,3-dione to give 1-ethoxycarbonylmethyl-3-(1-ethoxycarbonyl-3-phenylpropylamino)-2,3,4,5-tetrahydro-1H-[1]benzazepine-2-one of example 10.

The starting material was prepared as follows:

A solution of 3,3-dichloro-2,3,4,5-tetrahydro-1H-[1]benzazepin-2-one (1.0 g, 4.32 mmol) and ethyl bromoacetate (0.51 ml) in of tetrahydrofuran (30 ml) was added dropwise with stirring during 15 minutes to a solution of sodium hydride (4.76 mmol) in tetrahydrofuran (20 ml) at room temperature under a nitrogen atmosphere. Stirring was continued for an additional 2 hours. The solution was quenched by addition of saturated aqueous ammonium chloride and the solvents were removed under reduced pressure. The residue was extracted with ether (3×20 ml), and the combined ether solutions washed with saturated brine (20 ml) and dried over magnesium sulfate. Removal of the solvent under reduced pressure gave 3,3-dichloro-1-ethoxycarbonylmethyl-2,3,4,5-tetrahydro-1H-[1]benzazepin-2-one. NMR(CDCl$_3$): δ1.27 (t, 3H); 3.22 (m, 4H); 4.25 (q, 2H); 4.65 (s, 2H), 7.3 (m, 4H).

A mixture of morpholine (0.315 ml, 3.6 mmol) and 3,3-dichloro-1-ethoxycarbonylmethyl-2,3,4,5-tetrahydro-1H-[1]benzazepin-2-one (0.5 g) was stirred under nitrogen at 110° for 18 hours. The solution was diluted to 10 ml with chloroform and cooled to 0°. 20% H$_2$SO$_4$ (1 ml) was added and the solution stirred for 2 hours at 0°. The solution was extracted with chloroform (2×20 ml) and the extracts washed with 2N HCl (2×10 ml) and saturated brine (5 ml). The solution was dried over magnesium sulfate and evaporated under reduced pressure to yield 1-ethoxycarbonylmethyl-2,3,4,5-tetrahydro-1H-[1]benzazepin-2,3-dione. NMR (CDCl$_3$): δ1.25 (t,3H); 2.6 (m,2H); 3.6 (m, 2H); 4.2 (q, 2H); 7.3 (m, 4H).

EXAMPLE 31

Ethyl 2-amino-4-phenylbutyrate is treated in the presence of potassium carbonate in methylene chloride with 3-bromo-1-ethoxycarbonylmethyl-2,3,4,5-tetrahydro-1H-[1]benzazepin-2-one to give 1-ethoxycarbonylmethyl-3-(1-ethoxycarbonyl-3-phenylpropylamino)-2,3,4,5-tetrahydro-1H[1]benzazepin-2-one of example 10.

The starting material is prepared as follows:

To a solution of 2,3,4,5-tetrahydro-1H-[1]benzazepin-2-one (2.5 g) in chloroform (30 ml), phosphorus pentachloride (3.2 g) was added in portions, while maintaining the temperature at 0°-5°. When the addition was complete, iodine (30 mg) was added followed by bromine (2.5 g), which was added dropwise over 5 minutes. The mixture was then refluxed for 4 hours. The chloroform solution was evaporated and the residue was partitioned between ice-water (30 ml) and dichloromethane (75 ml). The organic phase was dried over magnesium sulfate and evaporated under reduced pressure. The crude residue was purified by chromatography over silica gel, eluting with ether and hexane (7:3). Concentration of the appropriate fractions yielded 3-bromo-2,3,4,5-tetrahydro-1H-[1]-benzazepin-2-one, m.p. 146°-148°.

3-Bromo-2,3,4,5-tetrahydro-1H-[1]-benzazepin-2-one (300 mg) was added in one portion to a stirred suspension of potassium hydroxide (90 mg) and tetrabutylammonium bromide (40 mg) in tetrahydrofuran (10 ml) maintained at 0° under a nitrogen atmosphere. Stirring was continued for 5 minutes, then ethyl bromoacetate (200 mg) was added in one portion. The reaction mixture was allowed to warm to room temperature while stirring for an additional 3 hours. The tetrahydrofuran was removed under reduced pressure and the residue partitioned between water (5 ml) and ether (25 ml). The organic phase was washed with 2N hydrochloric acid (5ml), dried over magnesium sulfate, and the solvent removed under reduced pressure to give 3-bromo-1-ethoxycarbonylmethyl-2,3,4,5-tetrahydro-1H-[1]-benzazepin-2-one, m.p. 114°-116°.

3-Chloro-1-ethoxycarbonylmethyl-2,3,4,5-tetrahydro-1H-[1]-benzazepin-2-one was similarly prepared.

A solution of 3-chloro-2,3,4,5-tetrahydro-1H-[1]benzazepine-2-one (1.95 g) in dimethylformamide (10 ml) was added dropwise with stirring to a solution of potassium t-butoxide (1.12 g) in dimethylformamide (10 ml) at 5°. The solution was stirred for an additional 15 minutes at 5°, then ethyl bromoacetate (1.78 g) in dimethylformamide (5 ml) was added dropwise. Stirring was continued for an additional 30 minutes at 5° and then for 3 hours at room temperature. The reaction mixture was cooled to 10° and water (100 ml) was added. The solution was extracted with chloroform (100 ml) and the chloroform solution washed with water (2×10 ml) and dried over sodium sulfate. The solvent was removed under reduced pressure to yield 3-chloro-1-ethoxycarbonylmethyl-2,3,4,5-tetrahydro-1H-[1]benzazepin-2-one; NMR(DMSO-d$_6$): δ1.2(t,3H); 2.65(m,4H); 4.15(q,2H); 2.6(d,2H); 7.3(m).

EXAMPLE 32

1-carboxymethyl-3S-(1S-pivaloyloxymethoxycarbonyl-3-phenylpropylamino)-2,3,4,5-tetrahydro-1H-[1]benzazepin-2-one 1-Benzyloxycarbonylmethyl-3S-(1S-pivaloyloxymethoxycarbonyl-3-phenylpropylamino)-2,3,4,5-tetrahydro-1H-[1]benzazepin-2-one (3 g) is dissolved in ethanol (50 ml) and 10% Pd-C (0.3 g) is added and the solution hydrogenated at 1 atmosphere pressure and room temperature for 2 hours. The reaction mixture is filtered and evaporated to yield 1-carboxymethyl-3S-(1S-pivaloyloxymethoxycarbonyl-3-phenylpropylamino)-2,3,4,5-tetrahydro-1H-[1]benzazepin-2-one.

The starting material is prepared as follows:

1-benzyloxycarbonylmethyl-3S-(1S-carboxy-3-phenylpropylamino)-2,3,4,5-tetrahydro-1H-[1]benzazepin-2-one (5 g, Example 2) is dissolved in 2N KOH (5.15 ml) and the solution evaporated to dryness. Iodomethyl pivalate (2.3 g) and dimethylformamide (50 ml) are added, and the reaction mixture is stirred at room temperature for 18 hours under a nitrogen atmosphere. The dimethylformamide is evaporated and the residue is taken up in ethyl acetate (100 ml) and washed with saturated sodium bicarbonate (3×25 ml), water (3×25 ml), and saturated sodium chloride (25 ml), and dried over magnesium sulfate. Evaporation gives 1-benzyloxycarbonylmethyl-3S-(1S-pivaloyloxymethoxycarbonyl-3-phenylpropylamino)-2,3,4,5-tetrahydro-1H-[1]benzazepin-2-one.

Similarly prepared are:

(a) 1-carboxymethyl-3S-(1S-l-bornyloxycarbonylmethoxycarbonyl-3-phenylpropylamino)-2,3,4,5-tetrahydro-1H-[1]benzazepin-2-one using l-bornyl iodoacetate as starting material.

(b) 1-carboxymethyl-3S-(1S-β-methoxyethoxymethoxycarbonyl-3-phenylpropylamino)-2,3,4,5-tetrahydro-1H-[1]benzazepin-2-one using β-methoxyethoxymethyl chloride as starting material.

(c) 1-carboxymethyl-3S-[1S-(3-phthalidoxycarbonyl)-3-phenylpropylamino]-2,3,4,5-tetrahydro-1H[1]benzazepin-2-one using 3-bromophthalide as starting material.

(d) 1-carboxymethyl-3S-[1S-(3-pyridylmethoxycarbonyl)-3-phenylpropylamino]-2,3,4,5-tetrahydro-1H[1]benzazepin-2-one using 3-pyridylmethyl chloride as starting material.

EXAMPLE 33

1-Carboxymethyl-3S-(1-ethoxycarbonyl-3-phenylpropylamino)-2,3,4,5,5a,6,7,8,9,9a-decahydro-1H-[1]benzazepin-2-one A solution of 3-(S)-amino-1-carboxymethyl-2,3,4,5,5a,6,7,8,9,9a-decahydro-1H-[1]benzazepin-2-one sodium salt (0.6 g) and ethyl benzylpyruvate (1.5 g) in acetic acid (5 ml) and methanol (3 ml) is stirred at room temperature under an atmosphere of dry nitrogen for 1 hour. A solution of sodium cyanoborohydride (0.2 g) in methanol (2 ml) is then added over a 4 hour period. The reaction mixture is stirred at room temperature for 18 hours. Concentrated hydrochloric acid (0.5 ml) is added and the mixture stirred at room temperature for 1 hour. The solvents are removed under reduced pressure and the residue partitioned between water (20 ml) and ether (20 ml). The pH is adjusted to 9.3 with 40% sodium hydroxide. The layers are separated and the ether layer discarded. The aqueous phase is adjusted to pH 4.3 with concentrated hydrochloric acid and extracted with ethyl acetate (3×25 ml). The extracts are dried over magnesium sulfate and the solvent removed under reduced pressure. Hydrogen chloride is bubbled into a solution of the residue in dichloromethane (70 ml) for 5 minutes. The solution is evaporated and the residue recrystallized from ethanol/ether to give 1-carboxymethyl-3S-(1-ethoxycarbonyl-3-phenylpropylamino)-2,3,4,5,5a,6,7,8,9,9a-decahydro-1H-[1]benzazepin-2-one-hydrochloride as a mixture of isomers.

The starting material is prepared as follows:

A solution of 3-(S)-t-butyloxycarbonylamino-1-ethoxycarbonylmethyl-2,3,4,5-tetrahydro-1H[1]-benzazepin-2,5-dione (3.6 g) in acetic acid (50 ml) is hydrogenated for 120 hours at 3 atmospheres pressure using platinum oxide (1.2 g) as catalyst. The catalyst is filtered off and the filtrate evaporated under reduced pressure. The residue is distributed between dichloromethane (200 ml) and saturated aqueous sodium bicarbonate (100 ml). The dichloromethane solution is washed with water (50 ml), dried over sodium sulfate and the solvent removed under reduced pressure. The residue is chromatographed on silica gel eluting with 0–50% ethyl acetate in toluene. The fraction eluting with 50% ethyl acetate in toluene is collected to give 3-(S)-t-butyloxycarbonylamino-1-ethoxycarbonylmethyl-2,3,4,5,5a,6,7,8,9,9a-decahydro-1H-[1]benzazepin-2,5-dione used without further purification for the next synthetic step.

A solution of 3-(S)-t-butyloxycarbonylamino-1-ethoxycarbonylmethyl-2,3,4,5,5a,6,7,8,9,9a-decahydro-1H-[1]benzazepin-2,5-dione (2.7 g) and sodium borohydride (0.2 g) in ethanol (100 ml) is stirred at room temperature for 18 hours. The solvent is removed under reduced pressure, and the residue dissolved in dichloromethane (100 ml). The solution is extracted with ice-cold 2N HCl (2×50 ml) and saturated brine (50 ml) and dried over sodium sulfate. The solvent is removed under reduced pressure and the residue triturated with ether to give 3-(S)-t-butyloxycarbonylamino-1-ethoxycarbonylmethyl-5-hydroxy-2,3,4,5,5a,6,7,8,9,9a-decahydro-1H-[1]benzazepin-2-one.

A mixture of 3-(S)-t-butyloxycarbonylamino-1-ethoxycarbonylmethyl-5-hydroxy-2,3,4,5,5a,6,7,8,9,9a-decahydro-1H-[1]benzazepin-2-one (2.1 g), dicyclohexylcarbodiimide (1.8 g) and cuprous chloride (0.2 g) is heated at 80° under nitrogen for 32 hours. The reaction mixture is cooled to room temperature, the residue is dissolved in methylene chloride (200 ml), washed with dilute ammonium hydroxide (2×50 ml) and water (50 ml). The organic phase is dried over sodium sulfate and evaporated to give a mixture of the desired adduct and excess dicyclohexylcarbodiimide. This mixture is dissolved in ethyl acetate (100 ml) and placed in a pressure bottle. 10% Pd/C (0.4 g) is added and the mixture hydrogenated at 3 atmospheres pressure and 40° for 16 hours. The catalyst is filtered off and the filtrate is evaporated to give 3-(S)-t-butyloxycarbonylamino-1-ethoxycarbonylmethyl-2,3,4,5,5a,6,7,8,9,9a-decahydro-1H-[1]benzazepin-2-one, used without further purification for the next synthetic step.

Hydrogen chloride gas is bubbled through a solution of the above compound (1.1 g) in ethyl acetate (50 ml) for 45 minutes. The reaction mixture is evaporated under reduced pressure and the residue dissolved in ethyl acetate (50 ml) and washed with water (3×30 ml). The ethyl acetate solution is dried over sodium sulfate and the solvent removed under reduced pressure to give 3-(S)-amino-1-ethoxycarbonylmethyl-2,3,4,5,5a,6,7,8,9-,9a-decahydro-1H-[1]benzazepin-2-one, which is used without further purification for the next step.

A solution of sodium hydroxide (0.1 g) in water (0.25 ml) is added to a solution of the above amine (0.6 g) in methanol (7.5 ml) at room temperature, and the solution is stirred for 2 hours. The solvents are evaporated and the residue thoroughly dried, then slurried with ether, to give the sodium salt of 3-(S)-amino-1-carboxymethyl-2,3,4,5,5a,6,7,8,9,9a-decahydro-1H-[1]benzazepin-2-one.

EXAMPLE 34

N-[1-(1-carboxymethyl)-2,3,4,5-tetrahydro-2-oxo-1H-[1]benzazepin-3S-ylamino)-3-phenylpropyl-1-carbonyl]-L-phenylalanine L-Phenylalanine methyl ester hydrochloride is condensed with 1-benzyloxycarbonylmethyl-3S-(1S-carboxy-3-phenylpropylamino)-2,3,4,5-tetrahydro-1H-[1]benzazepine-2-one in methylene chloride in the presence of 1-(3-dimethylaminopropyl)-3-ethylcarbodiimide hydrochloride at room temperature to yield after workup the N-[1-(1-benzyloxycarbonylmethyl-2,3,4,5-tetrahydro-2-oxo-1H-[1]benzazepin-3S-ylamino)-3-phenylpropyl-1-carbonyl]-L-phenylalanine methyl ester.

Hydrogenation using 10% Pd/C catalyst in ethanol gives N-[1-(1-carboxymethyl-2,3,4,5-tetrahydro-2-oxo-1H-[1]benzazepin-3-S-ylamino)-3-phenylpropyl-1-carbonyl]-L-phenylalanine methyl ester.

Hydrolysis with dilute aqueous sodium hydroxide at room temperature for 18 hours yields the N-[1-(1-carboxymethyl-2,3,4,5-tetrahydro-2-oxo-1H-[1]benzazepin-3S-ylamino)-3-phenylpropyl-1-carbonyl]-L-phenylalanine.

EXAMPLE 35

1-Ethoxycarbonylmethyl-3-(1-ethoxycarbonyl-3-phenylpropylamino)-2,3,4,5-tetrahydro-1H-[1]-benzazepin-2-one Treatment of 3-(1-carboxy-3-phenylpropylamino)-1-cyanomethyl-2,3,4,5-tetrahydro-1H[1]benzazepin-2-one with ethanol-ether (1:1) saturated with hydrogen chloride at room temperature for 48 hours gives after workup 1-ethoxycarbonylmethyl-3-(1-ethoxycarbonyl-3-phenylpropylamino)-2,3,4,5-tetrahydro-1H-[1]benzazepin-2-one identical to the compound of example 10.

The starting material is prepared as follows:

3-(1-carboxy-3-phenylpropylamino)-2,3,4,5-tetrahydro-1H-1-benzazepin-2-one is alkylated with bromoacetonitrile in dimethylformamide solution in the presence of sodium hydride to yield after work-up, 3-(1-carboxy-3-phenylpropylamino)-1-cyanomethyl-2,3,4,5-tetrahydro-1H-1-benzazepin-2-one, used directly in the next step.

EXAMPLE 36

Preparation of 10,000 tablets each containing 10 mg of the active ingredient of Example 12:

| Formula: | |
|---|---|
| 1-Carboxymethyl-3S—(1S—ethoxycarbonyl-3-phenylpropylamino)-2,3,4,5-tetrahydro-1H—[1]benzazepin-2-one. | 100.00 g |
| Lactose | 1,157.00 g |
| Corn starch | 75.00 g |
| Polyethylene glycol 6,000 | 75.00 g |
| Talcum powder | 75.00 g |
| Magnesium stearate | 18.00 g |
| Purified water | q.s. |

Procedure

As described in Example 15.

EXAMPLE 37

Preparation of 10,000 capsules each containing 20 mg of the hydrochloride salt of the active ingredient of Example 12.

| Formula: | |
|---|---|
| 1-Carboxymethyl-3S—(1S—ethoxycarbonyl-3-phenyl-propylamino)-2,3,4,5-tetrahydro-1H—[1]-benzazepin-2-one hydrochloride | 200.00 g |
| Lactose | 1,700.0 g |
| Talcum powder | 100.0 g |

Procedure

As described in Example 17.

EXAMPLE 38

1-Carboxymethyl-3S-(1-ethoxycarbonyl-3-phenylpropylamino)-2,3,4,5,5a,6,7,8,9,9a-decahydro-1H-[1]benzazepin-2-one hydrochloride A solution of 3-(S)-amino-1-carboxymethyl-2,3,4,5,5a,6,7,8,9,9a-decahydro-1H-[1]benzazepin-2-one hydrochloride (4 g) and ethyl benzylpyruvate (8.9 g) in methanol (30 ml) and acetic acid (30 ml) was stirred at room temperature for 1 hour. A solution of sodium cyanoborohydride (1.09 g) in methanol (15 ml) was added dropwise during 5 hours, and the reaction mixture was stirred at room temperature for an additional 18 hours. Concentrated hydrochloric acid (6 ml) was added, and stirring continued for an additional 1 hour. The solvents were removed under reduced pressure and the residue partitioned between ice/water (250 ml) and ether (100 ml). The pH was adjusted to 9.3 with 40% aqueous sodium hydroxide, and the ether layer discarded. The pH of the aqueous solution was adjusted to 4.3 by the addition of concentrated hydrochloric acid, and the solution was extracted with ethyl acetate (3×75 ml). The combined ethyl acetate solutions were dried over sodium sulfate and evaporated under reduced pressure. The residue was recrystallized from 3-pentanone to give 1-carboxymethyl-3S-(1-ethoxycarbonyl-3-phenylpropylamino)-2,3,4,5,5a,6,7,8,9,9a-decahydro-1H-[1]benzazepin-2-one hydrochloride, mp 192°-193° C.

The starting material was prepared as follows:

To a solution of 3-(S)-amino-1-carboxymethyl-2,3,4,5-tetrahydro-1H-[1]benzazepin-2-one sodium salt (8 g) and triethylamine (6.5 ml) in water (50 ml) was added a solution of BOC-ON (8.5 g) in dioxane (50 ml). The reaction mixture was stirred for 18 hours at room temperature, when water (100 ml) was added. The reaction mixture was extracted with ether (2×50 ml), and then the aqueous phase was acidified with concentrated hydrochloric acid. The aqueous solution was extracted with ethyl acetate (2×100 ml) and the combined ethyl acetate solutions dried over sodium sulfate and evaporated under reduced pressure. Recrystallization from ethyl acetate/hexane gave the N-t-butyloxycarbonyl derivative, mp 144°–145° C.

A solution of 3-(S)-t-butyloxycarbonylamino-1-carboxymethyl-2,3,4,5-tetrahydro-1H-[1]benzazepin-2-one (5 g) in ethanol (100 ml) was hydrogenated at 45 psi using 5% rhodium on carbon (2 g) as catalyst, until uptake ceased. The catalyst was filtered off (celite) and the solvent removed under pressure to give 3-(S)-t-butyloxycarbonylamino-1-carboxymethyl-2,3,4,5,5a,6,7,8,9,9a-decahydro-1H-[1]benzazepin-2-one which was used without further purification for the next synthetic step.

Hydrogen chloride gas was bubbled into a solution of 3-(S)-t-butyloxycarbonylamino-1-carboxymethyl-2,3,4,5,5a,6,7,8,9,9a-decahydro-1H-[1]benzazepin-2-one (20 g) in ethyl acetate (200 ml) for 15 minutes. The reaction mixture was stirred for an additional 20 minutes at room temperature, the solvent removed under reduced pressure, and the residue recrystallized from ethyl acetate/ether to give the amine hydrochloride, used without further purification for the next synthetic step.

EXAMPLE 39

5-Acetoxy-1-carboxymethyl-3S-(1-ethoxycarbonyl-3-phenylpropylamino)-2,3,4,5-tetrahydro-1H-[1]benzazepin-2-one hydrochloride A solution of 5-acetoxy-3S-amino-1-carboxymethyl-2,3,4,5-tetrahydro-1H-[1]benzazepin-2-one trifluoroacetate (4 g) and ethyl benzylpyruvate (6.1 g) in methanol (30 ml) and acetic acid (30 ml) was stirred at room temperature for 1 hour. A solution of sodium cyanoborohydride (0.75 g) in methanol (10 ml) was then added dropwise during 7 hours. The reaction mixture was then stirred for an additional 18 hours at room temperature. Concentrated hydrochloric acid (4 ml) was added and stirring continued for an additional 1 hour. The solvents were removed under reduced pressure and the residue partitioned between ice/water (200 ml) and ether (50 ml). The pH was adjusted to 9.3 with 40% aqueous sodium hydroxide, and the ether layer discarded. The pH of the aqueous solution was adjusted to 4.3 with concentrated hydrochloric acid, and the solution was extracted with ethyl acetate (3×50 ml). The combined ethyl acetate solutions were dried over sodium sulfate and evaporated under reduced pressure. The residue was boiled with ethyl acetate (50 ml), cooled to room temperature, and filtered to give the title acetoxy compound, mp 215°–217° C.

The starting material was prepared as follows:

A solution of 3-(S)-t-butyloxycarbonylamino-1-t-butyloxycarbonylmethyl-5-acetoxy-2,3,4,5-tetrahydro-1H-[1]benzazepin-2-one (5 g) in trifluoroacetic acid (60 ml) was stirred at room temperature for 1 hour under a nitrogen atmosphere. The solvent was removed under reduced pressure and the residue washed with ether to give the acetoxy-amino acid trifluoroacetate, used without further purification in the next synthetic step.

EXAMPLE 40

To a solution of 1-ethoxycarbonylmethyl-2,3,4,5-tetrahydro-1H[1]-benzazepin-2,3-dione (11 g), ε-carbobenzyloxylysine methyl ester hydrochloride (14 g), triethylamine (6 ml), and dibutyltin dichloride (0.7 g) in methylene chloride (600 ml), 4 Å molecular sieves (50 g) were added. The reaction mixture was stirred and refluxed for 40 hours. After cooling to room temperature, the reaction mixture was filtered through celite and the solvent removed under reduced pressure. The residue was dissolved in methanol (750 ml) and acetic acid (28 ml). After 5 minutes, sodium cyanoborohydride (0.36 g) was added and the reaction mixture was stirred at room temperature for 72 hours, then acidified by the addition of concentrated hydrochloric acid (10 ml). The solution was evaporated to dryness to give an oil which was separated by flash chromatography using ethyl acetate/toluene (9:1) as the solvent system. Two discrete fractions (isomer A and isomer B of the carbobenzyloxydiester) were obtained, namely (a) 3-[(5-benzyloxycarbonylamino-1-methoxycarbonyl)pentylamino]-1-ethoxycarbonylmethyl-2,3,4,5-tetrahydro-1H-[1]benzazepin-2-one (Isomer A; $R_f$=0.7, NMR (CDCl$_3$) 1.47 (m,5H), 3.16 (m,4H).

(b) 3-[(5-benzyloxycarbonylamino-1-methoxycarbonyl)pentylamino]-1-ethoxycarbonylmethyl-2,3,4,5-tetrahydro-1H-[1]benzazepin-2-one (Isomer B); $R_f$=0.6 NMR (CDCl$_3$) 1.30 (m,5H), 3.06 (m,4H).

The starting material was prepared as follows:

A solution of 3-amino-1-ethoxycarbonylmethyl-2,3,4,5-tetrahydro-1H[1]benzazepin-2-one (8 g), acetic acid (0.4 ml), and t-butyl nitrite (4.5 ml) in chloroform (160 ml) was refluxed for 2 hours and cooled to room temperature. M-Chloroperbenzoic acid (6.0 g) was added in portions with stirring, and stirring was maintained for an additional 30 minutes. The solution was washed with saturated aqueous sodium bicarbonate (100 ml), 2N hydrochloric acid (50 ml), and water (50 ml), and dried over magnesium sulfate. The solvent was removed under reduced pressure and the residue triturated with ethyl acetate/petroleum ether (bp 60°–80° C.) to give the α-ketolactam as a yellow solid, mp 108°–110° C., used without further purification in the next step, namely 1-ethoxycarbonylmethyl-2,3,4,5-tetrahydro-1H[1]benzazepin-2,3-dione.

EXAMPLE 41

(a) To a solution of 3-[(5-benzyloxycarbonylamino-1-methoxycarbonyl)pentylamino]-1-ethoxycarbonylmethyl-2,3,4,5-tetrahydro-1H-[1]benzazepin-2-one (Isomer A: 1.5 g) in methanol (60 ml) at 0° C. was added 5% aqueous sodium hydroxide (5 ml), and the reaction mixture was stirred at room temperature for 18 hours. The solution was acidified with 2N hydrochloric acid and evaporated to dryness. Ethanol (25 ml) was added and the solution evaporated to dryness. The resulting white solid was stirred with methylene chloride (30 ml), and the remaining solid filtered off. This material was stirred with methylene chloride (30 ml), and filtered. The combined methylene chloride solutions were evaporated and the resulting solid triturated with ether and filtered to give 3-[(5-benzyloxycarbonylamino-1-carboxy)pentylamino]-1-carboxymethyl-2,3,4,5-tetrahydro-1H-[1]benzazepin-2-one hydrochloride (Isomer A), mp 123°-126° C., $[\alpha]_D=106°$ (c=1, MeOH).

(b) Similarly, 3-[(5-benzyloxycarbonylamino-1-methoxycarbonyl)pentylamino]-1-ethoxycarbonylmethyl-2,3,4,5-tetrahydro-1H-[1]benzazepin-2-one (Isomer B) yields 3-(5-benzyloxycarbonylamino-1-carboxy)pentylamino]-1-carboxymethyl-2,3,4,5-tetrahydro-1H[1]benzazepin-2-one hydrochloride (Isomer B), mp 107°-110° C., $[\alpha]_D=-88°$ (c=1.26, MeOH), assigned the S,S stereochemistry.

EXAMPLE 42

3-[(5-amino-1-carboxy)pentylamino]-1-carboxymethyl-2,3,4,5-tetrahydro-1H-[1]-benzazepin-2-one hydrochloride (Isomer A)

A solution of 3-[(5-benzyloxycarbonylamino-1-carboxy)pentylamino]-1-carboxymethyl-2,3,4,5-tetrahydro-1H-[1]benzazepin-2-one hydrochloride (Isomer A; 0.5 g) in ethanol (150 ml) was hydrogenated at atmospheric pressure and room temperature using 10% palladium on charcoal (0.5 g) as catalyst until uptake of hydrogen ceased. The catalyst was filtered off and washed with water. The combined filtrates were evaporated and the resulting solid recrystallized from methanol/ether to give the diamino-diacid hydrochloride, mp 192°-195° C., (dec.) $[\alpha]_D=145°$ (c=0.3, dimethylformamide), representing the title compound.

EXAMPLE 43

3-[(5-amino-1-carboxy)pentylamino]-1-carboxymethyl-2,3,4,5-tetrahydro-1H-[1]-benzazepin-2-one hydrochloride (Isomer B)

A solution of 3-[(5-benzyloxycarbonylamino-1-carboxy)pentylamino]-1-carboxymethyl-2,3,4,5-tetrahy-dro-1H[1]benzazepin-2-one hydrochloride (Isomer B; 0.5 g) in ethanol (200 ml) was hydrogenated at atmospheric pressure and room temperature using 10% palladium on charcoal (0.5 g) as catalyst until uptake of hydrogen ceased. The catalyst was filtered off and washed with water. The combined filtrates were evaporated and the resulting solid recrystallized from methanol/ether to give the diamino-diacid hydrochloride, mp 148°-150° C., (dec.) $[\alpha]_D=-112°$ (c=0.75, water), representing the title compound assigned the S,S stereochemistry.

EXAMPLE 44

The following compounds of formula IA, wherein X represents 2 hydrogens; $R_2$ to $R_5$ represent hydrogen; $R_6$ is hydroxy or ethoxy; and $R_7$ is hydroxy, may be prepared essentially according to the procedures illustrated in the previous examples, advantageously as the S,S isomers thereof.

| Compound | $R_1$ | Derivatives |
|---|---|---|
| 44a | 3-indolylethyl | |
| 44b | 3-indolylmethyl | |
| 44c | ethoxycarbonylmethyl | |
| 44d | methylthioethyl | |
| 44e | 3-aminopropyl | |
| 44f | 4-benzoylaminobutyl | |
| 44g | n-propyl | |
| 44h | 4-aminobutyl | hexahydro |
| 44i | 4-(benzyloxycarbonylamino)butyl | hexahydro |
| 44j | phenoxyethyl | |
| 44k | phenylthioethyl | |
| 44l | hydroxymethyl | |
| | Starting Materials for: | |

-continued

| | |
|---|---|
| 44a | ethyl 4-(3-indolyl)-2-oxobutyrate. |
| 44b | L-tryptophane ethyl ester |
| 44c | L-aspartic acid diethyl ester |
| 44e | L-N—benzyloxycarbonyl-L-ornithine ethyl ester |
| 44f | N—benzoyl-L-lysine ethyl ester |
| 44g | ethyl 2-oxopentanoate |
| 44h | L-N—benzyloxycarbonyl-L-lysine ethyl ester |
| 44i | L-N—benzyloxycarbonyl-L-lysine ethyl ester |
| 44j | ethyl 4-phenoxy-2-aminobutyrate |
| 44k | ethyl 4-phenylthio-2-aminobutyrate |
| 44l | L-Serine ethyl ester |

What is claimed is:

1. A compound having the formula

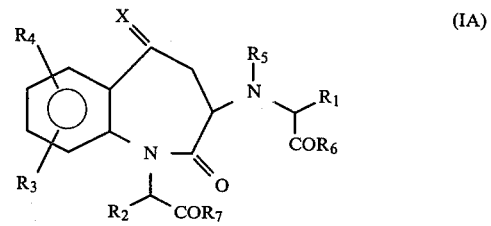

(IA)

wherein the carbocyclic ring may also be hexahydro;
$R_1$ is hydrogen, lower alkyl, amino(lower)alkyl, aryl, aryl(lower)alkyl, cycloalkyl or cycloalkyl(lower)alkyl;
$R_2$ and $R_5$ represent hydrogen or lower alkyl;
$R_3$ and $R_4$ represent hydrogen, lower alkyl, lower alkoxy, lower alkanoyloxy, hydroxy, halogen, trifluoromethyl; or $R_3$ and $R_4$ taken together represent lower alkylenedioxy;
X represents one acylated hydroxy group and one hydrogen;
$R_6$ and $R_7$ independently represent hydroxy, amino, mono- or di-(lower)alkylamino, lower alkoxy, aryl(lower)alkoxy, lower alkanoyloxymethoxy, (amino, mono- or di-lower alkylamino, carboxy, or lower alkoxycarbonyl)-lower alkoxy; and
wherein within the above definitions acylated hydroxy represents lower alkanoyloxy, nicotinoyloxy, benzoyloxy or benzoyloxy substituted on the phenyl ring by lower alkyl, halogen or lower alkoxy; and
wherein within the above definitions aryl represents phenyl unsubstituted or mono- or di-substituted by lower alkyl, lower alkoxy, lower alkylenedioxy, lower alkanoyloxy, hydroxy, halogen or trifluoromethyl; and cycloalkyl contains 3 to 8 carbons; or a pharmaceutically acceptable salt thereof.

2. A compound having the formula

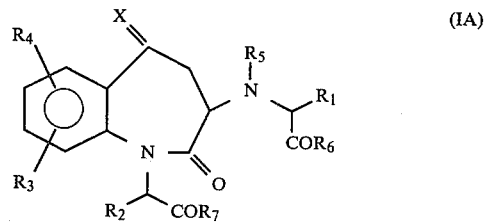

(IA)

wherein the carbocyclic ring may also be hexahydro;
$R_1$ is indolyl(lower)alkyl, mono- or di-(lower)alkylamino(lower)alkyl, lower alkylthio(lower)alkyl, hydroxy(lower)alkyl, aryloxy(lower)alkyl, arylthio(lower)alkyl, aryl-N-(lower)alkylamino(- lower)alkyl or arylamino(lower)alkyl; or $R_1$ is etherified hydroxy(lower)alkyl in which etherified hydroxy represents lower alkoxy or benzyloxy; or $R_1$ is acylated hydroxy(lower)alkyl; or $R_1$ represents carboxy(lower)alkyl, esterified carboxy(lower)alkyl, carbamoyl(lower)alkyl, N-substituted carbamoyl (lower)alkyl wherein carboxy, esterified carboxy, carbamoyl and N-substituted carbamoyl are as represented by $COR_6$ and $COR_7$; or $R_1$ is acylamino(lower)alkyl in which acylamino represents lower alkanoylamino; lower alkoxycarbonylamino; aryl(lower)alkanoylamino; aryl(lower)alkoxycarbonylamino; or aroylamino in which aroyl represents benzoyl or benzoyl substituted by lower alkyl, lower alkoxy or halogen, or nicotinoyl;

$R_2$ and $R_5$ represent hydrogen or lower alkyl;

$R_3$ and $R_4$ represent hydrogen, lower alkyl, lower alkoxy, lower alkanoyloxy, hydroxy, halogen, trifluoromethyl; or $R_3$ and $R_4$ taken together represent lower alkylenedioxy;

X represents oxo, two hydrogens, or one hydroxy or acylated hydroxy group and one hydrogen;

$R_6$ and $R_7$ independently represent hydroxy, amino, mono- or di-(lower)alkylamino, lower alkoxy, aryl(lower)alkoxy, lower alkanoyloxymethoxy, (amino, mono- or di-lower alkylamino, carboxy or lower alkoxycarbonyl)-lower alkoxy; and wherein within the above definitions aryl represents phenyl unsubstituted or mono- or di-substituted by lower alkyl, lower alkoxy, lower alkylenedioxy, lower alkanoyloxy, hydroxy, halogen or trifluoromethyl; and wherein within the above definitions acylated hydroxy represents lower alkanoyloxy, nicotinoyloxy, benzoyloxy or benzoyloxy substituted on the phenyl ring by lower alkyl, halogen or lower alkoxy;

or a pharmaceutically acceptable salt thereof.

3. A compound as claimed in claim 2 wherein $R_1$ is indolyl(lower)alkyl, carboxy(lower)alkyl, lower alkoxycarbonyl(lower)alkyl, hydroxy(lower)alkyl, lower alkylthio(lower)alkyl, acylamino(lower)alkyl, aryloxy(lower)alkyl or arylthio(lower)alkyl; and in which aryl, acylamino, X and $R_2$ to $R_7$ are as defined in said claim; or a pharmaceutically acceptable salt thereof; or any said compound wherein the carbocyclic ring is hexahydro.

4. A compound as claimed in claim 2 whrein $R_1$ is acylamino(lower)alkyl in which acylamino represents lower alkanoylamino, lower alkoxycarbonylamino, phenyl(lower)alkoxycarbonylamino or benzoylamino;

$R_2$ and $R_5$ are hydrogen or lower alkyl;

$R_3$ and $R_4$ are hydrogen, lower alkoxy, lower alkyl, halogen or trifluoromethyl; or $R_3$ and $R_4$ taken together represent alkylenedioxy;

X represents oxo, one hydroxy or lower alkanoyloxy and one hydrogen, or 2 hydrogens;

$R_6$ and $R_7$ independently represent hydroxy, amino, lower alkoxy, phenyl(lower)alkoxy, lower alkoxycarbonyl(lower)alkoxy; or a pharmaceutically acceptable salt thereof; or any said compound wherein the carbocyclic ring is hexahydro.

5. A compound as claimed in claim 2 wherein $R_1$ is aryl(lower)alkoxycarbonylamino-(lower)alkyl wherein aryl represents phenyl unsubstituted or mono-substituted by lower alkyl, hydroxy, lower alkoxy, lower alkanoyloxy, halogen or trifluoromethyl;

$R_2$ and $R_5$ are hydrogen or lower alkyl;

$R_3$ and $R_4$ are hydrogen, lower alkoxy, lower alkyl, halogen, or trifluoromethyl; or $R_3$ and $R_4$ taken together represent lower alkylenedioxy;

X represents oxo, one hydroxy or lower alkanoyloxy and one hydrogen, or 2 hydrogens;

$R_6$ and $R_7$ independently represent hydroxy, amino, lower alkoxy, phenyl(lower)alkoxy or lower alkoxycarbonyl(lower)alkoxy; or a pharmaceutically acceptable salt thereof.

6. A compound of claim 1 and formula IA wherein $R_1$ is ω-arylmethoxycarbonylamino-(lower) alkyl where aryl represents phenyl unsubstituted or monosubstituted by lower alkyl, hydroxy, lower alkoxy, lower alkanoyloxy, halogen or trifluoromethyl;

$R_2$ and $R_5$ are hydrogen or lower alkyl;

$R_3$ is hydrogen;

$R_4$ is hydrogen, lower alkoxy, lower alkyl, halogen, or trifluoromethyl; 7

X represents oxo, one hydroxy or lower alkanoyloxy and one hydrogen, or 2 hydrogens;

$R_6$ and $R_7$ independently represent hydroxy, amino, lower alkoxy, phenyl(lower)alkoxy, lower alkoxycarbonyl(lower)alkoxy;

or a pharmaceutically acceptable salt thereof; or any said compound wherein the carbocyclic ring is hexahydro.

7. A compound having the formula

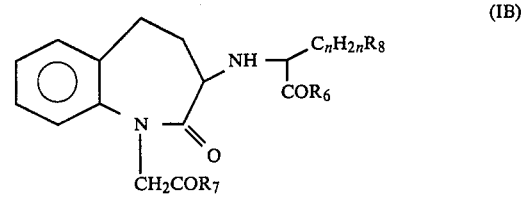

(IB)

wherein the carboxylic ring may also be hexahydro;

n represents an integer from 1 to 4;

$R_8$ is amino, benzyloxycarbonylamino;

$R_6$ and $R_7$ independently represent hydroxy, lower alkoxy of up to 4 carbon atoms, benzyloxy, amino; or a pharmaceutically acceptable salt thereof.

8. A compound as claimed in claim 7 wherein $C_nH_{2n}$ represents n-propylene or n-butylene; $R_8$ represents amino or benzyloxycarbonylamino; $R_6$ and $R_7$ independently represent hydroxy or lower alkoxy with up to 4 carbon atoms; or a pharmaceutically acceptable salt thereof; or any said compound wherein the carboxylic ring is hexahydro.

9. A compound of claim 7 being 3-[(5-benzyloxycarbonylamino-1-carboxy)pentylamino]-1-carboxymethyl-2,3,4,5-tetrahydro-1H-[1]benzazepin-2-one, a stereoisomer or a pharmaceutically acceptable salt thereof.

10. A compound of claim 1 being 5-acetoxy-1-carboxymethyl-3-(1-ethoxycarbonyl-3-phenylpropylamino)-2,3,4,5-tetrahydro-1H-[1]benzazepin-2-one, a stereoisomer or a pharmaceutically acceptable salt thereof.

11. A pharmaceutical composition suitable for oral or parenteral administration to mammals for the treatment or prevention of diseases responsive to inhibition of angiotensin-converting enzyme comprising an effective amount of a compound of claim 2 in combination with one or more pharmaceutically acceptable carriers.

12. A method of treating hypertensive or cardiac conditions in mammals which comprises administering to a mammal in need thereof an effective amount of a composition of claim 11.

13. A method of inhibiting angiotensin-converting enzyme which comprises administering to a mammal in need thereof an effective amount of a composition of claim 11.

14. A compound according to claim 7 being 3-(5-amino-1-carboxypentylamino)-1-carboxymethyl-2,3,4,5-tetrahydro-1H-[1]benzazepin-2-one, a stereoisomer or a pharmaceutically acceptable salt thereof.

15. A pharmaceutical composition suitable for oral or parenteral administration to mammals for the treatment or prevention of diseases responsive to inhibition of angiotensin-converting enzyme comprising an effective amount of a compound of claim 1 in combination with one or more pharmaceutically acceptable carriers.

16. A method of treating hypertensive or cardiac conditions in mammals which comprises administering to a mammal in need thereof an effective amount of a composition of claim 15.

17. A method of inhibiting angiotensin-converting enzyme which comprises administering to a mammal in need thereof an effective amount of a composition of claim 15.

18. A pharmaceutical composition suitable for oral or parenteral administration to mammals for the treatment or prevention of diseases responsive to inhibition of angiotensin-converting enzyme comprising an effective amount of a compound of claim 7 in combination with one or more pharmaceutically acceptable carriers.

19. A method of treating hypertensive or cardiac conditions in mammals which comprises administering to a mammal in need thereof an effective amount of a composition of claim 18.

20. A method of inhibiting angiotensin-converting enzyme which comprises administering to a mammal in need thereof an effective amount of a composition of claim 18.

21. A compound according to claim 7 having the formula

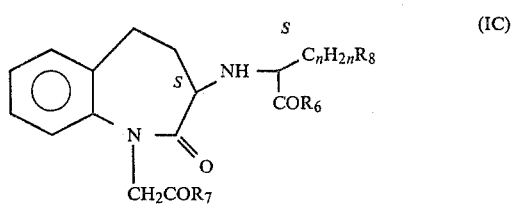

wherein S represents the chirality,
n represents an integer from 1 to 4;
$R_8$ is amino or benzyloxycarbonylamino;
$R_6$ and $R_7$ independently represent hydroxy, lower alkoxy of up to 4 carbon atoms, benzyloxy or amino; or a pharmaceutically acceptable salt thereof.

22. A compound according to claim 21 being the S,S-stereoisomer of 3-(5-amino-1-carboxypentylamino)-1-carboxymethyl-2,3,4,5-tetrahydro-1H-[1]-benzazepin-2-one or a pharmaceutically acceptable salt thereof.

* * * * *

UNITED STATES PATENT AND TRADEMARK OFFICE
CERTIFICATE OF CORRECTION

PATENT NO. : 4,473,575

DATED : September 25, 1984

INVENTOR(S) : Jeffrey W. H. Watthey

It is certified that error appears in the above-identified patent and that said Letters Patent is hereby corrected as shown below:

Example 40, Column 60, Line 16 should read-- ml). After 5 minutes, sodium cyanoborohydride (3.6g) --.

UNITED STATES PATENT AND TRADEMARK OFFICE
CERTIFICATE OF CORRECTION

PATENT NO. : 4,473,575

DATED : September 25, 1984

INVENTOR(S) : Jeffrey W. H. Watthey

It is certified that error appears in the above-identified patent and that said Letters Patent is hereby corrected as shown below:

Claim 6, Column 64, Line 13 should read--

A compound of claim 2 and formula IA wherein

Claim 6, Column 64, Line 21 should read-- or trifluoromethyl; --.

Signed and Sealed this

First Day of October 1985

[SEAL]

Attest:

Attesting Officer

DONALD J. QUIGG

Commissioner of Patents and Trademarks—Designate